US009745552B2

(12) United States Patent
Fricke et al.

(10) Patent No.: US 9,745,552 B2
(45) Date of Patent: Aug. 29, 2017

(54) ANTI CD4 ANTIBODIES TO PREVENT IN PARTICULAR GRAFT-VERSUS-HOST-DISEASE (GVHD)

(75) Inventors: Stephan Fricke, Leipzig (DE); Frank Emmrich, Leipzig (DE); Nadja Hilger, Leipzig (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 910 days.

(21) Appl. No.: 13/990,996

(22) PCT Filed: Dec. 2, 2011

(86) PCT No.: PCT/EP2011/006060
§ 371 (c)(1),
(2), (4) Date: Aug. 21, 2013

(87) PCT Pub. No.: WO2012/072268
PCT Pub. Date: Jun. 7, 2012

(65) Prior Publication Data
US 2013/0330334 A1 Dec. 12, 2013

(30) Foreign Application Priority Data
Dec. 2, 2010 (EP) .................................... 10015236

(51) Int. Cl.
| | |
|---|---|
| *C12N 5/0783* | (2010.01) |
| *C12N 5/077* | (2010.01) |
| *C12N 5/078* | (2010.01) |
| *A61K 35/28* | (2015.01) |
| *C07K 16/28* | (2006.01) |
| *C12N 5/00* | (2006.01) |
| *A61K 35/12* | (2015.01) |
| *A61K 39/00* | (2006.01) |

(52) U.S. Cl.
CPC ............ *C12N 5/0669* (2013.01); *A61K 35/28* (2013.01); *C07K 16/2812* (2013.01); *C12N 5/0087* (2013.01); *C12N 5/0648* (2013.01); *A61K 2035/124* (2013.01); *A61K 2039/505* (2013.01)

(58) Field of Classification Search
None
See application file for complete search history.

(56) References Cited

U.S. PATENT DOCUMENTS

| | | | | |
|---|---|---|---|---|
| 9,156,912 B2 * | 10/2015 | Matsushima | ........ | A61K 39/395 |
| 2003/0153043 A1 | 8/2003 | Carr et al. | | |
| 2004/0228848 A1 * | 11/2004 | Har-Noy | ............... | C12N 5/0636 424/93.71 |
| 2010/0074904 A1 * | 3/2010 | Schneider | ............ | G01N 33/505 424/152.1 |
| 2013/0004513 A1 * | 1/2013 | Osterroth | ........... | C07K 16/2812 424/172.1 |

FOREIGN PATENT DOCUMENTS

| | | |
|---|---|---|
| DE | 3919294 A1 | 1/1991 |
| EP | 0 403 935 A1 | 12/1990 |
| EP | 1 454 137 A2 | 9/2004 |
| WO | WO-91/06667 A1 | 5/1991 |
| WO | WO-96/36359 A1 | 11/1996 |
| WO | WO-98/59244 A1 | 12/1998 |
| WO | WO-00/34317 A2 | 6/2000 |
| WO | WO-01/68813 A1 | 9/2001 |
| WO | WO-03/050499 A2 | 6/2003 |
| WO | WO-2004/112835 A2 | 12/2004 |

OTHER PUBLICATIONS

Gallardo et al. (Bone Marrow Transplantation, (1997) 20, 945-952).*
Davis et al. (Cytometry 33:197-205 (1998)).*
Burmester et al., Clinical and Experimental Rheumatology 11 (Suppl. 8): S139-S145, 1993.*
Repke et al., J Immunol 1992; 149:1809-1816.*
Corbeau et al., J Immunol 1993; 150:290-301.*
Wang et al., PNAS, 2001, vol. 98, No. 19, 10799-10804.*
Rezvani et al., Blood. Aug. 15, 2006;108(4):1291-7.*
Wolf et al., Transplantation. Apr. 27, 2007;83(8):1107-13.*
Edinger et al., Nature Medicine, 2003, vol. 9, No. 9, 1144-50.*
Mischke et al. (Immunobiology; 2004; 209, 4-6, pp. 483 and 488).*
Mischke et al. (Biocity Leipzig, 5th Biotechnology Symposium, 2006, pp. 130-131).*
Seddiki et al., JEM, vol. 203, No. 7, Jul. 10, 2006 1693-1700.*
Booth et al., The Journal of Immunology, 2010, 184: 4317-4326.*
Becker et al., Eur J Nucl Med. 1990;17(3-4):156-9.*
Abufarang et al., "Selective activation of naturally occurring regulatory T cells (Tregs) by the monoclonal antibody BT-061 as a novel therapeutic opportunity in psoriasis: Early clinical results after single doses," Poster No. 379, one page, presented in 2010 at ESDR.*

(Continued)

*Primary Examiner* — Zachary Skelding
(74) *Attorney, Agent, or Firm* — Clark & Elbing LLP; Kristina Bieker-Brady

(57) ABSTRACT

The present invention relates to, among others, an in vitro method of modifying a cell graft containing immune cells comprising the steps of incubating a cell graft containing immune cells with an anti CD4 antibody wherein said incubating is carried out for from 1 minute to 7 days, b) removing unbound antibody from said graft; as well as to corresponding modified grafts and uses. The invention further relates to the modification of antibodies reactive to the CD4 human leukocyte antigen to provide anti-CD4 antibodies that have a reduced number of potential T-cell epitopes but retain the ability to bind to CD4, such as to an anti human CD4-antibody comprising a heavy chain immunoglobulin variable domain (VH) and a light chain immunoglobulin variable domain (VL), wherein at least one T cell epitope located outside the CDRs of said immunoglobulin variable domains is removed from said immunoglobulin variable domains. Preferably, the specificity and mode of action of the anti-CD4 antibodies are not affected by the modification(s).

8 Claims, 25 Drawing Sheets

(56) References Cited

OTHER PUBLICATIONS

Bandeira et al. (Nat Biotechnol. Dec. 2008;26(12):1336-8).*
IMGT Repertoire, Mus musculus, IGHJ, http://www.imgt.org/IMGTrepertoire/Proteins/proteinDisplays.php?species=house mouse&latin=Mus musculus&group=IGHJ, cited herewith p. 1 of 1, Nov. 14, 2012.*
IMGT Repertoire, Mus musculus, IGKJ, http://www.imgt.org/IMGTrepertoire/Proteins/proteinDisplays.php?species=house mouse&latin=Mus musculus&group=IGKJ, cited herewith p. 1 of 1, Nov. 14, 2012.*
IMGT M34749, createed Jul. 23, 1995, pp. 1-2.*
IMGT M97877, created Jul. 23, 1995, pp. 1-2.*
Clarke et al., J Immunol 1990; 144:2795-2801, clone H37-41 in Fig. 2.*
Nagler et al., Transplantation. Jul. 15, 1998;66(1):138-41.*
Antibody Engineering, R. Kontermann and S. Dubel (eds.), vol. 2, Chapter 37, Olafsen et al., pp. 491-506, 2010.*
Labrijn et al., Current Opinion in Immunology 2008, 20:479-485.*
Vidarsson et al., Front Immunol. Oct. 20, 2014;5:520.*
Kihara et al., "Studies on transient graft-versus-host disease in BALB/c nude mice injected with allogeneic C57BL/6 splenocytes," J Dermatol Sci. 11(1):76-83 (1996).
Maraninchi et al., "Impact of T-cell depletion on outcome of allogeneic bone-marrow transplantation for standard-risk leukaemias," Lancet 2(8552):175-8 (1987).
Aschan, "Allogeneic haematopoietic stem cell transplantation: current status and future outlook," Br Med Bull. 77-78:23-36 (2006).
Auletta et al., "Bone marrow transplantation: new approaches to immunosuppression and management of acute graft-versus-host disease," Curr Opin Pediatr. 21(1):30-8 (2009).
Bacigalupo et al., "Bone marrow or peripheral blood as a source of stem cells for allogeneic transplantation," Curr Opin Hematol. 7(6) 343-7 (2000).
Bates et al., "Clinical utility of rituximab in chronic graft-versus-host disease," Ann Pharmacother. 43(2):316-21 (2009).
Benekli et al., "Muromonab-CD3 (Orthoclone OKT3), methylprednisolone and cyclosporine for acute graft-versus-host disease prophylaxis in allogeneic bone marrow transplantation," Bone Marrow Transplant. 38(5):365-70 (2006).
Boon et al., "Development of anti-CD4 MAb hu5A8 for treatment of HIV-1 infection: preclinical assessment in non-human primates," Toxicology. 172(3):191-203 (2002).
Bowers et al., "CD4: a co-receptor in the immune response and HIV infection," Int J Biochem Cell Biol. 29(6):871-5 (1997).
Braun, "Anti-CD4 targeting", 3rd CELLAID Symposium Cell therapies for autoimmune diseases, retrieved from the internet <http://www.cellaid-eu.org/pdf/Cellaid_2007_program.pdf; p. 22> 1-48 (2007).
Bushell et al., "Donor-recipient microchimerism is not required for tolerance induction following recipient pretreatment with donor-specific transfusion and anti-CD4 antibody. Evidence of a clear role for short-term antigen persistence," Transplantation. 59(10):1367-71 (1995).
Chatenoud et al., "Tolerance induction in the adult: 'danger' at Le Bischenberg," Immunol Today. 16(3):121-3 (1995).
Chester et al., "Clinical issues in antibody design," Trends Biotechnol. 13(8):294-300 (1995).
Cooke et al., "An experimental model of idiopathic pneumonia syndrome after bone marrow transplantation: I. The roles of minor H antigens and endotoxin," Blood. 8(8):3230-9 (1996).
DelMonico et al., "Anti-CD4 monoclonal antibody therapy," Clin Transplant. 10(5):397-403 (1996).
Emmrich et al., "An anti-CD4 antibody for treatment of chronic inflammatory arthritis," Agents Actions Suppl. 32:165-70 (1991).
Emmrich et al., "Treatment of inflammatory bowel disease with anti-CD4 monoclonal antibody," Lancet. 338(8766):570-1 (1991).
Emmrich et al., "[Treatment of autoimmune diseases and graft rejection with anti-CD4 antibodies]," Z Gesamte Inn Med. 47((111):500-7.(1992) (English Abstract Only).

Fehervari et al., "Perturbation of naive TCR transgenic T cell functional responses and upstream activation events by anti-CD4 monoclonal antibodies," Eur J Immunol. 32(2):333-40 (2002).
Graca et al., "Co-receptor and co-stimulation blockade for mixed chimerism and tolerance without myelosuppressive conditioning," BMC Immunol. 7(9):1-8 (2006).
Harding et al., "A therapeutic CD4 monoclonal antibody inhibits TCR-zeta chain phosphorylation, zeta-associated protein of 70-kDa Tyr319 phosphorylation, and TCR internalization in primary human T cells," J Immunol. 169(1):230-8 (2002).
Harlow et al., "Antibody purification on protein a or protein g columns," CSH Protoc. <http://cshprotocols.cshlp.org/content/2006/1/pdb.prot4283.full>, retrieved Oct. 1, 2013 (2 pages).
Higuchi et al., "A general method of in vitro preparation and specific mutagenesis of DNA fragments: study of protein and DNA interactions," Nucleic Acids Res. 16(15):7351-67 (1988).
Hosono et al., "Human/mouse chimeric antibodies show low reactivity with human anti-murine antibodies (HAMA)," Br J Cancer. 65(2):197-200 (1992).
Isaacs., "The antiglobulin response to therapeutic antibodies," Immunol. 2:449-56 (1990).
Ji et al., "Anti-CD25 monoclonal antibody (basiliximab) for prevention of graft-versus-host disease after haploidentical bone marrow transplantation for hematological malignancies," Bone Marrow Transplant. 36(4):349-54 (2005).
Kern et al., "T-cell epitope mapping by flow cytometry," Nat Med. 4(8):975-8 (1998).
Kestendjieva et al., "Characterization of mesenchymal stem cells isolated from the human umbilical cord," Cell Biol Int. 32(7):724-32 (2008).
Knop et al., "Treatment of steroid-resistant acute GvHD with OKT3 and high-dose steroids results in better disease control and lower incidence of infectious complications when compared to high-dose steroids alone: a randomized multicenter trial by the EBMT Chronic Leukemia Working Party," Leukemia. 21(8):1830-3 (2007).
Kohlhaw et al., "The monoclonal anti-CD4 antibody RIB5/2 induces donor-specific tolerance in the high-responder liver transplant model in the rat," Transplant Proc. 33(3):2371-3 (2001).
Kwok et al., "Rapid epitope identification from complex class-II-restricted T-cell antigens," Trends Immunol. 22(11):583-8 (2001).
Laub et al., "A multiple transgenic mouse model with a partially humanized activation pathway for helper T cell responses," J Immunol Methods. 246(1-2):37-50 (2000).
Laub et al., "Anti-human CD4 induces peripheral tolerance in a human CD4+, murine CD4-, HLA-DR+ advanced transgenic mouse model," J Immunol. 169(6):2947-55 (2002).
Madrenas et al., "Interleukin 2 production, not the pattern of early T-cell antigen receptor-dependent tyrosine phosphorylation, controls anergy induction by both agonists and partial agonists," Proc Natl Acad Sci USA. 93(18):9736-41 (1996).
Marshall et al., "Role of the polymorphic residues in HLA-DR molecules in allele-specific binding of peptide ligands," J Immunol. 152(10):4946-57 (1994).
O'Sullivan et al., "Characterization of the specificity of peptide binding to four DR haplotypes," J Immunol. 145(6):1799-808 (1990).
Reinke et al., "Anti-CD4 monoclonal antibody therapy of late acute rejection in renal allograft recipients—CD4+ T cells play an essential role in the rejection process," Transplant Proc. 27(1):859-62 (1995).
Reinke et al., "Anti-CD4 therapy of acute rejection in long-term renal allograft recipients," Lancet. 338(8768):702-3 (1991).
Risch et al., "Inhibition of chronic rejection after kidney transplantation by anti-CD4 treatment," Transplant Proc. 29(1-2):328-9 (1997).
Robadey et al., "The processing routes determined by negatively charged residues in DR1-restricted T cell determinants," J Immunol. 159(7):3238-46 (1997).
Schroff et al., "Human anti-murine immunoglobulin responses in patients receiving monoclonal antibody therapy," Cancer Res. 45(2):879-85 (1985).
Senolt et al., "Prospective new biological therapies for rheumatoid arthritis," Autoimmun Rev. 9(2):102-7 (2009).

(56) References Cited

OTHER PUBLICATIONS

Stern et al., "Crystal structure of the human class II MHC protein HLA-DR1 complexed with an influenza virus peptide," Nature. 368(6468):215-21 (1994).
von Bonin et al., "Treatment of refractory acute GvHD with third-party MSC expanded in platelet lysate-containing medium," Bone Marrow Transplant. 43(3):245-51 (2009).
International Search Report for International Applicaiton No. PCT/EP2011/006060, mailed Jul. 19, 2012 (7 pages).
International Preliminary Report on Patentability for International Application No. PCT/EP2011/006060, dated Jun. 4, 2013 (9 pages).
Extended European Search Report for European Application No. 10015236.2, dated May 24, 2011 (7 pages).
Battaglia et al., "Expanding human T regulatory cells with the mTOR-inhibitor rapamycin," Methods Mol Biol. 821:279-93 (2012).
Canavan et al., "Developing in vitro expanded CD45RA+ regulatory T cells as an adoptive cell therapy for Crohn's disease," Gut. 65(4):584-94 (2016) with supplemental content (27 pages).
Ellis et al., "Generation of induced regulatory T cells from primary human naïve and memory T cells," J Vis Exp. (62)pii: 3738 (2012) (5 pages).
Golab et al., "Impact of culture medium on CD4(+)CD25(high)CD127(lo/neg) Treg expansion for the purpose of clinical application," Int Immunopharmacol. 16(3):358-63 (2013).
Hippen et al., "Massive ex vivo expansion of human natural regulatory T cells (Tregs) with minimal loss of in vivo functional activity," available in PMC Jan. 22, 2013, published in final edited form as: Sci Transl Med. 3(83):83ra41 (2011) (16 pages).
Hoffmann et al., "Large-scale in vitro expansion of polyclonal human CD4(+)CD25high regulatory T cells," Blood. 104(3):895-903 (2004).
Hoffmann et al., "Loss of FOXP3 expression in natural human CD4+CD25+ regulatory T cells upon repetitive in vitro stimulation," Eur J Immunol. 39(4):1088-97 (2009).
Hoffmann et al., "Only the CD45RA+ subpopulation of CD4+CD25high T cells gives rise to homogeneous regulatory T-cell lines upon in vitro expansion," Blood. 108(13):4260-7 (2006).
Kameda et al., "Rheumatoid arthritis," Nippon Rinsho. 67(3):495-99 (2009) (English language abstract).
Marek et al., "The time is crucial for ex vivo expansion of T regulatory cells for therapy," Cell Transplant. 20(11-12):1747-58 (2011).
Rossetti et al., "Ex vivo-expanded, but not in vitro-induced, human regulatory T cells are candidates for cell therapy in autoimmune diseases due to stable demethylation of the FOXP3 TSDRa," available in PMC Jan. 1, 2016, published in final edited form as: J Immunol. 194(1):113-24 (2015) (27 pages).
Scotta et al., "Differential effects of rapamycin and retinoic acid on expansion, stability and suppressive qualities of human CD4(+)CD25(+)FOXP3(+) T regulatory cell subpopulations," Haematologica. 98(8):1291-9 (2013).
Theil et al., "Adoptive transfer of allogeneic regulatory T cells into patients with chronic graft-versus-host disease," Cytotherapy. 17(4):473-86 (2015).
Trzonkowski et al., "First-in-man clinical results of the treatment of patients with graft versus host disease with human ex vivo expanded CD4+CD25+CD127—T regulatory cells," Clin Immunol. 133(1):22-6 (2009).

* cited by examiner

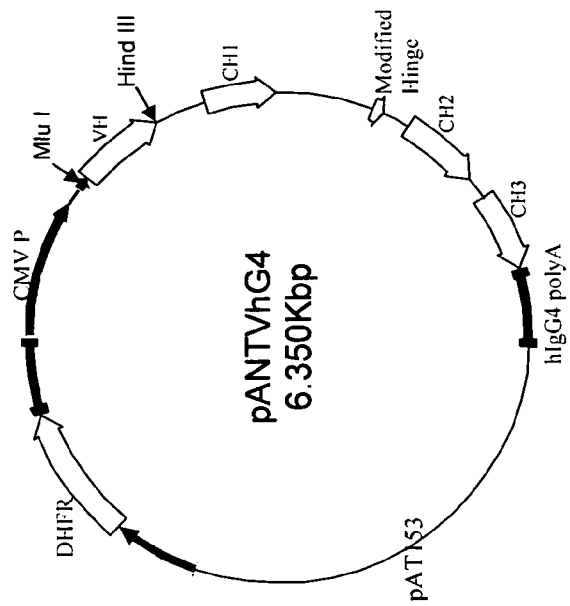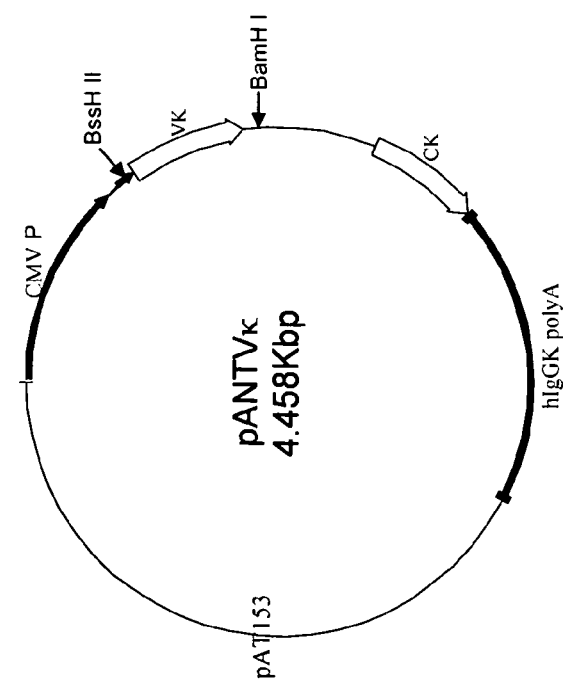
Figure 11

Fig 12: Sequences of Anti-CD4 Heavy Chain Variable Regions

(a) Mouse Anti-CD4 Heavy Chain

```
         10         20         30         40         50         60         70         80         90        100
GAGGTTCAGCTCCAGCAGTCTGGGACTGTGCTGGCAAGCCTGGGGCTTCCGTGCAGATGTCCTGCAAGGCTTCTGGCTACAGCTTTGCCAACTACTGGA
 E  V  Q  L  Q  Q  S  G  T  V  L  A  R  P  G  A  S  V  Q  M  S  C  K  A  S  G  Y  S  F  A  N  Y  W
                            10                          20                          30

110        120        130        140        150        160        170        180        190        200
TGCACTGGGTAAAACAGAGGCCTGGACAGGGTCTACAATGGATTGGTGCTCTTTATCCTGGAAATGTTGATACTACCTACAACCAGAAGTTCAAGGACAA
 M  H  W  V  K  Q  R  P  G  Q  G  L  Q  W  I  G  A  L  Y  P  G  N  V  D  T  T  Y  N  Q  K  F  K  D  K
                   40                          50  52 (A)                          60

210        220        230        240        250        260        270        280        290        300
GGCCAAACTGACTGCAGTCACATCCGCCAGCACTGCCTACATGGAGCTCAGCAGCCTGACAAATGAGGACTCTGCGGTCTATTACTGTACAAGAATGGGT
 A  K  L  T  A  V  T  S  A  S  T  A  Y  M  E  L  S  S  L  T  N  E  D  S  A  V  Y  Y  C  T  R  M  G
       70                          80  82 (A)(B)(C)                  90                         100

310        320        330        340        350        360
ACTACTTTAGAAGCCCCCCTTGACTATTGGGGCCAAGGCACCACTCTCACAGTCTCCTCA              SEQ ID NO: 1
 T  T  L  E  A  P  L  D  Y  W  G  Q  G  T  T  L  T  V  S  S                SEQ ID NO: 2
                   110                          120
         (A)(B)(C)
```

CDR definitions (and letters "(A)", "(B)" and "(C)") according to Kabat. CDR nucleotide and protein sequences are highlighted in italics

Figure 12 a

(b) Heavy chain VH4

```
         10         20         30         40         50         60         70         80         90        100
GAGGTTCAGCTCCAGCAGTCTGGGACTGAGCTGAAAAGGCCTGGGGCCTCCGTGAAGATGTCCTGCAAGGCTTCTGGCTACACCTTTGCCAACTACTGGA
 E  V  Q  L  Q  Q  S  G  T  E  L  K  R  P  G  A  S  V  K  M  S  C  K  A  S  G  Y  T  F  A  N  Y  W
                            10                            20                            30
                            —                                                    —

110        120        130        140        150        160        170        180        190        200
TGCACTGGGTAAAACAGGCCCCTGGACAGGGTCTACAATGGATTGGTGCTCTTTATCCTGGAAATGTTGATACTACTACAACCAGAAGTTCAAGGACAA
 M  H  W  V  K  Q  A  P  G  Q  G  L  Q  W  I  G  A  L  Y  P  G  N  V  D  T  T  Y  N  Q  K  F  K  D  K
                   —                                          50        52 (A)               60
                   40

210        220        230        240        250        260        270        280        290        300
GGCCAAACTGACTGCAGTCACATCCGCCAGCACTGCCTACATGGAACTGAGCAGCCTGACAAATGAGGACTCTGCGGTCTATTACTGTACAAGAATGGGT
 A  K  L  T  A  V  T  S  A  S  T  A  Y  M  E  L  S  S  L  T  N  E  D  S  A  V  Y  Y  C  T  R  M  G
 70                                              80    82 (A) (B) (C)                    90                 100

310        320        330        340        350        360
ACTACTTTAGAAGCCCCCCTTGACTATTGGGGCCAAGGCACCACTCTCACAGTCTCCTCA
 T  T  L  E  A  P  L  D  Y  W  G  Q  G  T  T  V  T  V  S  S         SEQ ID NO: 3
      (A) (B) (C)            110                      —     120      SEQ ID NO: 4
```

CDR definitions (and letters "(A)", "(B)" and "(C)") according to Kabat. CDR nucleotide and protein sequences are highlighted in italics Differences from murine reference sequence are highlighted by underlining

Figure 12 b (c) Heavy chain VH3

```
         10         20         30         40         50         60         70         80         90        100
GAGGTTCAGCTCCAGCAGTCTGGGTCTGAGCTGAAAGGCCTGGAGCTGAGATCTCCTGAAGATGTCCTGCAAGGCTTCTGGCTACACCTTTGCCAACTACTGGA
 E   V   Q   L   Q   Q   S   G   S   E   L   K   R   P   G   A   S   V   K   M   S   C   K   A   S   G   Y   T   F   A   N   Y   W
                             1       5                                     20                                  30
                             _       _                                     _                           _
        110        120        130        140        150        160        170        180        190        200
TGCACTGGGTAAAACAGGCCCCTGGACAGGGTCTACAATGATTGGTGCTCTTTATCCTGGAAAATGTTGATACTACCTACAACCAGAAGTTCAAGGACAA
 M   H   W   V   K   Q   A   P   G   Q   G   L   Q   W   I   G   A   L   Y   P   G   N   V   D   T   T   Y   N   Q   K   F   K   D   K
                 _   40                                         50  52 (A)                         60
        210        220        230        240        250        260        270        280        290        300
GGCCAAACTGACTGCAGTCACATCCGCCAGCACTGCCTACATGGAGCTCCTCAGCAGCCTGACAAATGAGGACACCGCGGTCTATTACTGTACAAGAATGGGT
 A   K   L   T   A   V   T   S   A   S   T   A   Y   M   E   L   S   S   L   T   N   E   D   T   A   V   Y   Y   C   T   R   M   G
         70                                         80  82 (A) (B) (C)        90  _                           100
        310        320        330        340        350        360
ACTACTTTAGAAGCCCCCCTTGACTATTGGGGCCAAGGCACCCTTGTCACAGTCTCCTCA          SEQ ID NO: 5          SEQ ID NO: 6
 T   T   L   E   A   P   L   D   Y   W   G   Q   G   T   L   V   T   V   S   S
             110    (A) (B) (C)                      _               120
```

CDR definitions (and letters "(A)", "(B)" and "(C)") according to Kabat. CDR nucleotide and protein sequences are highlighted in italics Differences from murine reference sequence are highlighted by underlining

Figure 12 c (d) Heavy chain VH2

```
         10         20         30         40         50         60         70         80         90        100
GAGGTTCAGCTCCAGCAGTCTGGGTCTGAGCTGAAAAGGCCTGGGGCTTCCGTGAAGGTGTCCTGCAAGGCTTCTGGCTACACCTTTGCCAACTACTGGA
 E  V  Q  L  Q  Q  S  G  S  E  L  K  R  P  G  A  S  V  K  V  S  C  K  A  S  G  Y  T  F  A  N  Y  W
                        5         10                          20                         30
                        —  —                                  —                          —  —

110        120        130        140        150        160        170        180        190        200
TGCACTGGGTAAAACAGGCCCCTGGACAGGGTCTACAATGGATTGGTGCTCTTTATCCTGGAAATGTTGATACTACAACCAGAAGTTCAAGGACAA
 M  H  W  V  K  Q  A  P  G  Q  G  L  Q  W  I  G  A  L  Y  P  G  N  V  D  T  T  Y  N  Q  K  F  K  D  K
                   —                                      50          52 (A)                     60
                   40

210        220        230        240        250        260        270        280        290        300
GGCCAAACTGACTGCAGACACATCCGCCAGCACTGCCTACATGGAGCTCAGCAGCCTGACAAATGAGGACACCGCGGTCTATTACTGTACAAGAATGGGT
 A  K  L  T  A  D  T  S  A  S  T  A  Y  M  E  L  S  S  L  T  N  E  D  T  A  V  Y  Y  C  T  R  M  G
 70          —                                  80             82 (A) (B) (C)       —
                                                                                    90

310        320        330        340        350        360
ACTACTTTAGAAGCCCCCCTTGACTATTGGGGCCAAGGCACCCTTGTCACAGTCTCCTCA              SEQ ID NO: 7
 T  T  L  E  A  P  L  D  Y  W  G  Q  G  T  L  V  T  V  S  S                SEQ ID NO: 8
 (A) (B) (C)       110                 —  —                120
```

CDR definitions (and letters "(A)", "(B)" and "(C)") according to Kabat. CDR nucleotide and protein sequences are highlighted in italics Differences from murine reference sequence are highlighted by underlining

Figure 12 d

(e) Heavy chain VH1

```
         10         20         30         40         50         60         70         80         90        100
GAGGTTCAGCTGCAGCAGTCTGGGGCTGAGCTGGTGAAAAGGCCTGGGGCCTCAGTGAAGGTGTCCTGCAAGGCTTCTGGCTACACCTTTGCCAACTACTGGA
 E  V  Q  L  Q  Q  S  G  A  E  L  V  K  R  P  G  A  S  V  K  V  S  C  K  A  S  G  Y  T  F  A  N  Y  W
                            S  E                                 K                             T        30
                            10                                  20
        110        120        130        140        150        160        170        180        190        200
TGCACTGGGTAAGACAGGCCCCTGGACAGGGTCTCGAACAATGGATTGGTGCTCTTTATCCTGGAAATGTTGATACTACTTACAACCAGAAGTTCAAGGACAA
 M  H  W  V  R  Q  A  P  G  Q  G  L  Q  W  I  G  A  L  Y  P  G  N  V  D  T  T  Y  N  Q  K  F  K  D  K
             R     Q                                                                             60
             40                              50    52 (A)
        210        220        230        240        250        260        270        280        290        300
GGCCAAAATCACTAGAGACACATCCGCCAGCACTGCCTACATGGAGCTCAGCAGCCTCAGACAAATGAGGACACCGGTCTATTACTGTACAAGAATGGGT
 A  K  I  T  R  D  T  S  A  S  T  A  Y  M  E  L  S  S  L  T  N  E  D  T  A  V  Y  Y  C  T  R  M  G
    70                                           80    82 (A) (B) (C)          90                       100
        310        320        330        340        350        360
ACTACTTTAGAAGCCCCCCCTTGACTATTGGGGCCAAGGCACCCTTGTCACAGTCTCCTCA
 T  T  L  E  A  P  L  D  Y  W  G  Q  G  T  L  V  T  V  S  S
   (A) (B) (C)            110                        120
```

SEQ ID NO: 9
SEQ ID NO: 10

CDR definitions (and letters "(A)", "(B)" and "(C)") according to Kabat. CDR nucleotide and protein sequences are highlighted in italics Differences from murine reference sequence are highlighted by underlining

Figure 12 e

Fig 13: Sequences of Anti-CD4 Light Chain Variable Regions

(a) Mouse Anti-CD4 Light Chain

```
         10         20         30         40         50         60         70         80         90        100
CAAATTGTTCTCACCCAGTCTCCAGCAATCATGTCTCTGCATCTCCAGGGGAGAAGGTCGCCATGACCTGCAGTGCCAGTCAAGTGTAAGTTACTTGTACT
 Q  I  V  L  T  Q  S  P  A  I  M  S  A  S  P  G  E  K  V  A  M  T  C  S  A  R  S  S  V  S  Y  L  Y
                              10                      20                      30

110        120        130        140        150        160        170        180        190        200
GGTACCAGCAGAAGCCAGGATCCTCCCCAGACTCCTGATTTATGACACATCCAACCTGGCTTCTGGAGTCCCTGTTCGCTTCATTGGCAGTGGGTCTGG
 W  Y  Q  Q  K  P  G  S  S  P  R  L  L  I  Y  D  T  S  N  L  A  S  G  V  P  V  R  F  I  G  S  G  S  G
              40                      50                      60

210        220        230        240        250        260        270        280        290        300
GACCTCTTACTCTCTCACAATCAGCCGAATGGAGGCTGAAGATGCTGCCACTTATTACTGCCAGCAGTGGAGTGATTACCCGCTCACGTTCGGTGCTGGG
 T  S  Y  S  L  T  I  S  R  M  E  A  E  D  A  A  T  Y  Y  C  Q  Q  W  S  D  Y  P  L  T  F  G  A  G
      70                      80                      90                          100

310
ACCAAGCTGGAGCTGAAA       SEQ ID NO: 11
 T  K  L  E  L  K        SEQ ID NO: 12
    (A)
```

CDR definitions (and letter "(A)") according to Kabat. CDR nucleotide and protein sequences are highlighted in italics

Figure 13 a

(b) Light Chain VK4

```
         10         20         30         40         50         60         70         80         90        100
CAAATTGTTCTCACCCAGTCTCCAGCAATCCTGTCTGCATCTCCAGGGGAGAAGGCCGCCATGACCTGCAGTGCCAGGTCAAGTGTAAGTTACTTGTACT
 Q  I  V  L  T  Q  S  P  A  I  M  S  A  S  P  G  E  K  A  A  M  T  C  S  A  R  S  S  V  S  Y  L  Y
                            10                        20                        30
        110        120        130        140        150        160        170        180        190        200
GGTACCAGCAGAAGCCAGGGTCCTCCCCCAGACTCCTGATTTATGACACATCCAACCTGGCTTCTGAGTCCCTTCTCGCTTCATTGGCAGTGGGTCTGG
 W  Y  Q  Q  K  P  G  S  S  P  R  L  L  I  Y  D  T  S  N  L  A  S  G  V  P  S  R  F  I  G  S  G  S  G
                  40                        50                              60
        210        220        230        240        250        260        270        280        290        300
GACCGATTACTCTCTCACAATCAGCAGCATGGAGGCTGAAGATGCTGCCACTTATTACTGCCAGCAGTGGAGTGATTACCCGCTCACGTTCGGTGCTGGG
 T  D  Y  S  L  T  I  S  S  M  E  A  E  D  A  A  T  Y  Y  C  Q  Q  W  S  D  Y  P  L  T  F  G  A  G
       70                        80                              90                      100
310
ACCAAGCTGGAGATCAAA              SEQ ID NO: 13
 T  K  L  E  I  K               SEQ ID NO: 14
             (A)
```

CDR definitions (and letter "(A)") according to Kabat. CDR nucleotide and protein sequences are highlighted in italics Differences from murine reference sequence are highlighted by underlining

Figure 13 b

(c) Light chain VK3

```
         10         20         30         40         50         60         70         80         90        100
CAAATTGTTCTCACCCAGTCTCCAGCAACCCTGTCTGCATCTCCAGGGGAGAAGGCCGCCATGACCTGCAGTGCCAGTCAAGTGTAAGTTACTTGTACT
 Q  I  V  L  T  Q  S  P  A  T  L  S  A  S  P  G  E  K  A  A  M  T  C  S  A  R  S  S  V  S  Y  L  Y
                            10                        20                              30

110        120        130        140        150        160        170        180        190        200
GGTACCAGCAGAAGCCAGGGTCCTCCCCCAGACTCCTGATTTATGACACATCCAACCTGGCTTCTGGAGTCCCTTCATTGGCAGTGGGTCTGG
 W  Y  Q  Q  K  P  G  S  S  P  R  L  L  I  Y  D  T  S  N  L  A  S  G  V  P  S  R  F  I  G  S  G  S  G
                 40                              50                              60

210        220        230        240        250        260        270        280        290        300
GACCGATTACTCTCTCACAATCAGCAGCATGGAGGCTGAAGATGCTGCCACTTATTACTGCCAGCAGTGGAGTGATTACCCGCTCACGTTCGGTGCTGGG
 T  D  Y  S  L  T  I  S  S  M  E  A  E  D  A  A  T  Y  Y  C  Q  Q  W  S  D  Y  P  L  T  F  G  A  G
       70                              80                              90                       100

310
ACCAAGCTGGAGATCAAA       SEQ ID NO: 15
 T  K  L  E  I  K         SEQ ID NO: 16
           (A)
```

CDR definitions (and letter "(A)") according to Kabat. CDR nucleotide and protein sequences are highlighted in italics Differences from murine reference sequence are highlighted by underlining

Figure 13 c

(d) Light chain VK2

```
         10         20         30         40         50         60         70         80         90        100
CAAATTGTTCTCACCCAGTCTCCAGCAACCCTGTCTGCATCTCCAGGGGAGAAGGCCGCCATGACCTGCAGTGCCAGTTCAAGTGTAAGTTACTTGTACT
 Q  I  V  L  T  Q  S  P  A  T  L  S  A  S  P  G  E  K  A  A  M  T  C  S  A  R  S  S  V  S  Y  L  Y
                           10                          20                          30

110        120        130        140        150        160        170        180        190        200
GGTACCAGCAGAAGCCAGGGTCCTCCCCCAGACTCCTGATTTATGACACATCCAACCTGGCTTCTGGAGTCCCTTCTCGCTTCAGCGGCAGTGGGTCTGG
 W  Y  Q  Q  K  P  G  S  S  P  R  L  L  I  Y  D  T  S  N  L  A  S  G  V  P  S  R  F  S  G  S  G
                           40                          50                          60

210        220        230        240        250        260        270        280        290        300
GACCGATTACTCTCTCACAATCAGCAGCATGGAGGCTGAAGATGCTGCCACTTATTACTGCCAGCAGTGGAGTGATTACCCGCTCACGTTCGGTGCTGGG
 T  D  Y  S  L  T  I  S  S  M  E  A  E  D  A  A  T  Y  Y  C  Q  Q  W  S  D  Y  P  L  T  F  G  A  G
        70                          80                          90                         100

310
ACCAAGCTGGAGATCAAA                SEQ ID NO: 17
 T  K  L  E  I  K    (A)          SEQ ID NO: 18
```

CDR definitions (and letter "(A)") according to Kabat. CDR nucleotide and protein sequences are highlighted in italics Differences from murine reference sequence are highlighted by underlining

Figure 13 d

(e) Light chain VK1

```
         10        20        30        40        50        60        70        80        90       100
CAAATTGTTCTCACCCAGTCTCCAGCAACCCTGTCTCTGCATCTCCAGGGGAGAAGGCCGCCATGACCTGCAGTGCCAGTCAAGTGCCAGTCAAGTGTAAGTTACTTGTACT
 Q  I  V  L  T  Q  S  P  A  T  L  S  A  S  P  G  E  K  A  A  M  T  C  S  A  R  S  S  V  S  Y  L  Y
                            10                      20                              30

110       120       130       140       150       160       170       180       190       200
GGTACCAGCAGAAGCCAGGGTCCTCCCCCAGAGCCCTGATTTATGACACATCCAACCTGGCTTCTGGAGTCCCTTCTCGCTTCAGCGGCAGTGGGTCTGG
 W  Y  Q  Q  K  P  G  S  S  P  R  A  L  I  Y  D  T  S  N  L  A  S  G  V  P  S  R  F  S  G  S  G  S  G
                40                          50                              60

210       220       230       240       250       260       270       280       290       300
GACCGATTACTCTCTCACAATCAGCAGCATGGAGGCTGAAGATGCTGCCACTTATTACTGCCAGCAGTGGAGTGATTACCCGCTCACGTTCGGTGCTGGG
 T  D  Y  S  L  T  I  S  S  M  E  A  E  D  A  A  T  Y  Y  C  Q  Q  W  S  D  Y  P  L  T  F  G  A  G
    70                              80                              90                      100

310
ACCAAGCTGGAGATCAAA        SEQ ID NO: 19
 T  K  L  E  I  K          SEQ ID NO: 20
         (A)
```

CDR definitions (and letter "(A)") according to Kabat. CDR nucleotide and protein sequences are highlighted in italics Differences from murine reference sequence are highlighted by underlining

Figure 13 e

SEQUENCE LISTING

<160> NUMBER OF SEQ ID NOS: 138

<210> SEQ ID NO 1
<211> LENGTH: 360
<212> TYPE: DNA
<213> ORGANISM: Artificial Sequence
<220> FEATURE:
<223> OTHER INFORMATION: Mouse Anti-CD4 Heavy Chain
<220> FEATURE:
<221> NAME/KEY: CDS
<222> LOCATION: (1)..(360)

<400> SEQUENCE: 1

```
gag gtt cag ctc cag cag tct ggg act gtg ctg gca agg cct ggg gct      48
Glu Val Gln Leu Gln Gln Ser Gly Thr Val Leu Ala Arg Pro Gly Ala
1               5                   10                  15 tcc gtg cag atg tcc tgc aag gct tct ggc tac agc ttt gcc aac tac      96
Ser Val Gln Met Ser Cys Lys Ala Ser Gly Tyr Ser Phe Ala Asn Tyr
            20                  25                  30 tgg atg cac tgg gta aaa cag agg cct gga cag ggt cta caa tgg att     144
Trp Met His Trp Val Lys Gln Arg Pro Gly Gln Gly Leu Gln Trp Ile
        35                  40                  45 ggt gct ctt tat cct gga aat gtt gat act acc tac aac cag aag ttc     192
Gly Ala Leu Tyr Pro Gly Asn Val Asp Thr Thr Tyr Asn Gln Lys Phe
    50                  55                  60 aag gac aag gcc aaa ctg act gca gtc aca tcc gcc agc act gcc tac     240
Lys Asp Lys Ala Lys Leu Thr Ala Val Thr Ser Ala Ser Thr Ala Tyr
65                  70                  75                  80 atg gag ctc agc agc ctg aca aat gag gac tct gcg gtc tat tac tgt     288
Met Glu Leu Ser Ser Leu Thr Asn Glu Asp Ser Ala Val Tyr Tyr Cys
                85                  90                  95 aca aga atg ggt act act tta gaa gcc ccc ctt gac tat tgg ggc caa     336
Thr Arg Met Gly Thr Thr Leu Glu Ala Pro Leu Asp Tyr Trp Gly Gln
            100                 105                 110 ggc acc act ctc aca gtc tcc tca                                     360
Gly Thr Thr Leu Thr Val Ser Ser
        115                 120
```

<210> SEQ ID NO 2
<211> LENGTH: 120
<212> TYPE: PRT
<213> ORGANISM: Artificial Sequence
<220> FEATURE:
<223> OTHER INFORMATION: Synthetic Construct

<400> SEQUENCE: 2

```
Glu Val Gln Leu Gln Gln Ser Gly Thr Val Leu Ala Arg Pro Gly Ala
1               5                   10                  15

Ser Val Gln Met Ser Cys Lys Ala Ser Gly Tyr Ser Phe Ala Asn Tyr
            20                  25                  30

Trp Met His Trp Val Lys Gln Arg Pro Gly Gln Gly Leu Gln Trp Ile
        35                  40                  45

Gly Ala Leu Tyr Pro Gly Asn Val Asp Thr Thr Tyr Asn Gln Lys Phe
    50                  55                  60

Lys Asp Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95
```

```
Thr Arg Met Gly Thr Thr Leu Glu Ala Pro Leu Asp Tyr Trp Gly Gln
            100                 105                 110

Gly Thr Thr Leu Thr Val Ser Ser
        115                 120

<210> SEQ ID NO 3
<211> LENGTH: 360
<212> TYPE: DNA
<213> ORGANISM: Artificial Sequence
<220> FEATURE:
<223> OTHER INFORMATION: Heavy chain VH4
<220> FEATURE:
<221> NAME/KEY: CDS
<222> LOCATION: (1)..(360)

<400> SEQUENCE: 3 gag gtt cag ctc cag cag tct ggg act gag ctg aaa agg cct ggg gct      48
Glu Val Gln Leu Gln Gln Ser Gly Thr Glu Leu Lys Arg Pro Gly Ala
1               5                   10                  15 tcc gtg aag atg tcc tgc aag gct tct ggc tac acc ttt gcc aac tac      96
Ser Val Lys Met Ser Cys Lys Ala Ser Gly Tyr Thr Phe Ala Asn Tyr
            20                  25                  30 tgg atg cac tgg gta aaa cag gcc cct gga cag ggt cta caa tgg att     144
Trp Met His Trp Val Lys Gln Ala Pro Gly Gln Gly Leu Gln Trp Ile
        35                  40                  45 ggt gct ctt tat cct gga aat gtt gat act acc tac aac cag aag ttc     192
Gly Ala Leu Tyr Pro Gly Asn Val Asp Thr Thr Tyr Asn Gln Lys Phe
    50                  55                  60 aag gac aag gcc aaa ctg act gca gtc aca tcc gcc agc act gcc tac     240
Lys Asp Lys Ala Lys Leu Thr Ala Val Thr Ser Ala Ser Thr Ala Tyr
65                  70                  75                  80 atg gag ctc agc agc ctg aca aat gag gac tct gcg gtc tat tac tgt     288
Met Glu Leu Ser Ser Leu Thr Asn Glu Asp Ser Ala Val Tyr Tyr Cys
                85                  90                  95 aca aga atg ggt act act tta gaa gcc ccc ctt gac tat tgg ggc caa     336
Thr Arg Met Gly Thr Thr Leu Glu Ala Pro Leu Asp Tyr Trp Gly Gln
            100                 105                 110 ggc acc act gtc aca gtc tcc tca                                     360
Gly Thr Thr Val Thr Val Ser Ser
        115                 120

<210> SEQ ID NO 4
<211> LENGTH: 120
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Gln Gln Ser Gly Thr Glu Leu Lys Arg Pro Gly Ala
1               5                   10                  15

Ser Val Lys Met Ser Cys Lys Ala Ser Gly Tyr Thr Phe Ala Asn Tyr
            20                  25                  30

Trp Met His Trp Val Lys Gln Ala Pro Gly Gln Gly Leu Gln Trp Ile
        35                  40                  45

Gly Ala Leu Tyr Pro Gly Asn Val Asp Thr Thr Tyr Asn Gln Lys Phe
    50                  55                  60

Lys Asp Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95
```

```
Thr Arg Met Gly Thr Thr Leu Glu Ala Pro Leu Asp Tyr Trp Gly Gln
            100                 105                 110

Gly Thr Thr Val Thr Val Ser Ser
        115                 120

<210> SEQ ID NO 5
<211> LENGTH: 360
<212> TYPE: DNA
<213> ORGANISM: Artificial Sequence
<220> FEATURE:
<223> OTHER INFORMATION: Heavy chain VH3
<220> FEATURE:
<221> NAME/KEY: CDS
<222> LOCATION: (1)..(360)

<400> SEQUENCE: 5 gag gtt cag ctc cag cag tct ggg tct gag ctg aaa agg cct ggg gct      48
Glu Val Gln Leu Gln Gln Ser Gly Ser Glu Leu Lys Arg Pro Gly Ala
1               5                   10                  15 tcc gtg aag atg tcc tgc aag gct tct ggc tac acc ttt gcc aac tac      96
Ser Val Lys Met Ser Cys Lys Ala Ser Gly Tyr Thr Phe Ala Asn Tyr
            20                  25                  30 tgg atg cac tgg gta aaa cag gcc cct gga cag ggt cta caa tgg att     144
Trp Met His Trp Val Lys Gln Ala Pro Gly Gln Gly Leu Gln Trp Ile
        35                  40                  45 ggt gct ctt tat cct gga aat gtt gat act acc tac aac cag aag ttc     192
Gly Ala Leu Tyr Pro Gly Asn Val Asp Thr Thr Tyr Asn Gln Lys Phe
    50                  55                  60 aag gac aag gcc aaa ctg act gca gtc aca tcc gcc agc act gcc tac     240
Lys Asp Lys Ala Lys Leu Thr Ala Val Thr Ser Ala Ser Thr Ala Tyr
65                  70                  75                  80 atg gag ctc agc agc ctg aca aat gag gac acc gcg gtc tat tac tgt     288
Met Glu Leu Ser Ser Leu Thr Asn Glu Asp Thr Ala Val Tyr Tyr Cys
                85                  90                  95 aca aga atg ggt act act tta gaa gcc ccc ctt gac tat tgg ggc caa     336
Thr Arg Met Gly Thr Thr Leu Glu Ala Pro Leu Asp Tyr Trp Gly Gln
            100                 105                 110 ggc acc ctt gtc aca gtc tcc tca                                    360
Gly Thr Leu Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Gln Gln Ser Gly Ser Glu Leu Lys Arg Pro Gly Ala
1               5                   10                  15

Ser Val Lys Met Ser Cys Lys Ala Ser Gly Tyr Thr Phe Ala Asn Tyr
            20                  25                  30

Trp Met His Trp Val Lys Gln Ala Pro Gly Gln Gly Leu Gln Trp Ile
        35                  40                  45

Gly Ala Leu Tyr Pro Gly Asn Val Asp Thr Thr Tyr Asn Gln Lys Phe
    50                  55                  60

Lys Asp Lys Ala Lys Leu Thr Ala Val Thr Ser Ala Ser Thr Ala Tyr
65                  70                  75                  80

Met Glu Leu Ser Ser Leu Thr Asn Glu Asp Thr Ala Val Tyr Tyr Cys
                85                  90                  95
```

```
Thr Arg Met Gly Thr Thr Leu Glu Ala Pro Leu Asp Tyr Trp Gly Gln
            100                 105                 110

Gly Thr Leu Val Thr Val Ser Ser
        115                 120

<210> SEQ ID NO 7
<211> LENGTH: 360
<212> TYPE: DNA
<213> ORGANISM: Artificial Sequence
<220> FEATURE:
<223> OTHER INFORMATION: Heavy chain VH2
<220> FEATURE:
<221> NAME/KEY: CDS
<222> LOCATION: (1)..(360)

<400> SEQUENCE: 7 gag gtt cag ctc cag cag tct ggg tct gag ctg aaa agg cct ggg gct      48
Glu Val Gln Leu Gln Gln Ser Gly Ser Glu Leu Lys Arg Pro Gly Ala
1               5                   10                  15 tcc gtg aag gtg tcc tgc aag gct tct ggc tac acc ttt gcc aac tac      96
Ser Val Lys Val Ser Cys Lys Ala Ser Gly Tyr Thr Phe Ala Asn Tyr
            20                  25                  30 tgg atg cac tgg gta aaa cag gcc cct gga cag ggt cta caa tgg att     144
Trp Met His Trp Val Lys Gln Ala Pro Gly Gln Gly Leu Gln Trp Ile
        35                  40                  45 ggt gct ctt tat cct gga aat gtt gat act acc tac aac cag aag ttc     192
Gly Ala Leu Tyr Pro Gly Asn Val Asp Thr Thr Tyr Asn Gln Lys Phe
    50                  55                  60 aag gac aag gcc aaa ctg act gca gac aca tcc gcc agc act gcc tac     240
Lys Asp Lys Ala Lys Leu Thr Ala Asp Thr Ser Ala Ser Thr Ala Tyr
65                  70                  75                  80 atg gag ctc agc agc ctg aca aat gag gac acc gcg gtc tat tac tgt     288
Met Glu Leu Ser Ser Leu Thr Asn Glu Asp Thr Ala Val Tyr Tyr Cys
                85                  90                  95 aca aga atg ggt act act tta gaa gcc ccc ctt gac tat tgg ggc caa     336
Thr Arg Met Gly Thr Thr Leu Glu Ala Pro Leu Asp Tyr Trp Gly Gln
            100                 105                 110 ggc acc ctt gtc aca gtc tcc tca                                     360
Gly Thr Leu Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Gln Gln Ser Gly Ser Glu Leu Lys Arg Pro Gly Ala
1               5                   10                  15

Ser Val Lys Val Ser Cys Lys Ala Ser Gly Tyr Thr Phe Ala Asn Tyr
            20                  25                  30

Trp Met His Trp Val Lys Gln Ala Pro Gly Gln Gly Leu Gln Trp Ile
        35                  40                  45

Gly Ala Leu Tyr Pro Gly Asn Val Asp Thr Thr Tyr Asn Gln Lys Phe
    50                  55                  60

Lys Asp Lys Ala Lys Leu Thr Ala Asp Thr Ser Ala Ser Thr Ala Tyr
65                  70                  75                  80

Met Glu Leu Ser Ser Leu Thr Asn Glu Asp Thr Ala Val Tyr Tyr Cys
                85                  90                  95
```

```
Thr Arg Met Gly Thr Thr Leu Glu Ala Pro Leu Asp Tyr Trp Gly Gln
            100                 105                 110

Gly Thr Leu Val Thr Val Ser Ser
        115                 120

<210> SEQ ID NO 9
<211> LENGTH: 360
<212> TYPE: DNA
<213> ORGANISM: Artificial Sequence
<220> FEATURE:
<223> OTHER INFORMATION: Heavy chain VH1
<220> FEATURE:
<221> NAME/KEY: CDS
<222> LOCATION: (1)..(360)

<400> SEQUENCE: 9 gag gtt cag ctc cag cag tct ggg tct gag ctg aaa agg cct ggg gct      48
Glu Val Gln Leu Gln Gln Ser Gly Ser Glu Leu Lys Arg Pro Gly Ala
1               5                   10                  15 tcc gtg aag gtg tcc tgc aag gct tct ggc tac acc ttt gcc aac tac      96
Ser Val Lys Val Ser Cys Lys Ala Ser Gly Tyr Thr Phe Ala Asn Tyr
            20                  25                  30 tgg atg cac tgg gta aga cag gcc cct gga cag ggt cta caa tgg att     144
Trp Met His Trp Val Arg Gln Ala Pro Gly Gln Gly Leu Gln Trp Ile
        35                  40                  45 ggt gct ctt tat cct gga aat gtt gat act acc tac aac cag aag ttc     192
Gly Ala Leu Tyr Pro Gly Asn Val Asp Thr Thr Tyr Asn Gln Lys Phe
    50                  55                  60 aag gac aag gcc aaa atc act aga gac aca tcc gcc agc act gcc tac     240
Lys Asp Lys Ala Lys Ile Thr Arg Asp Thr Ser Ala Ser Thr Ala Tyr
65                  70                  75                  80 atg gag ctc agc agc ctg aca aat gag gac acc gcg gtc tat tac tgt     288
Met Glu Leu Ser Ser Leu Thr Asn Glu Asp Thr Ala Val Tyr Tyr Cys
                85                  90                  95 aca aga atg ggt act act tta gaa gcc ccc ctt gac tat tgg ggc caa     336
Thr Arg Met Gly Thr Thr Leu Glu Ala Pro Leu Asp Tyr Trp Gly Gln
            100                 105                 110 ggc acc ctt gtc aca gtc tcc tca                                     360
Gly Thr Leu Val Thr Val Ser Ser
        115                 120

<210> SEQ ID NO 10
<211> LENGTH: 120
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Gln Gln Ser Gly Ser Glu Leu Lys Arg Pro Gly Ala
1               5                   10                  15

Ser Val Lys Val Ser Cys Lys Ala Ser Gly Tyr Thr Phe Ala Asn Tyr
            20                  25                  30

Trp Met His Trp Val Arg Gln Ala Pro Gly Gln Gly Leu Gln Trp Ile
        35                  40                  45

Gly Ala Leu Tyr Pro Gly Asn Val Asp Thr Thr Tyr Asn Gln Lys Phe
    50                  55                  60

Lys Asp Lys Ala Lys Ile Thr Arg Asp Thr Ser Ala Ser Thr Ala Tyr
65                  70                  75                  80

Met Glu Leu Ser Ser Leu Thr Asn Glu Asp Thr Ala Val Tyr Tyr Cys
                85                  90                  95
```

Thr Arg Met Gly Thr Thr Leu Glu Ala Pro Leu Asp Tyr Trp Gly Gln
            100                 105                 110

Gly Thr Leu Val Thr Val Ser Ser
        115                 120

<210> SEQ ID NO 11
<211> LENGTH: 318
<212> TYPE: DNA
<213> ORGANISM: Artificial Sequence
<220> FEATURE:
<223> OTHER INFORMATION: Mouse Anti-CD4 Light Chain
<220> FEATURE:
<221> NAME/KEY: CDS
<222> LOCATION: (1)..(318)

<400> SEQUENCE: 11 caa att gtt ctc acc cag tct cca gca atc atg tct gca tct cca ggg     48
Gln Ile Val Leu Thr Gln Ser Pro Ala Ile Met Ser Ala Ser Pro Gly
1               5                   10                  15 gag aag gtc gcc atg acc tgc agt gcc agg tca agt gta agt tac ttg     96
Glu Lys Val Ala Met Thr Cys Ser Ala Arg Ser Ser Val Ser Tyr Leu
            20                  25                  30 tac tgg tac cag cag aag cca gga tcc tcc ccc aga ctc ctg att tat    144
Tyr Trp Tyr Gln Gln Lys Pro Gly Ser Ser Pro Arg Leu Leu Ile Tyr
        35                  40                  45 gac aca tcc aac ctg gct tct gga gtc cct gtt cgc ttc att ggc agt    192
Asp Thr Ser Asn Leu Ala Ser Gly Val Pro Val Arg Phe Ile Gly Ser
    50                  55                  60 ggg tct ggg acc tct tac tct ctc aca atc agc cga atg gag gct gaa    240
Gly Ser Gly Thr Ser Tyr Ser Leu Thr Ile Ser Arg Met Glu Ala Glu
65                  70                  75                  80 gat gct gcc act tat tac tgc cag cag tgg agt gat tac ccg ctc acg    288
Asp Ala Ala Thr Tyr Tyr Cys Gln Gln Trp Ser Asp Tyr Pro Leu Thr
                85                  90                  95 ttc ggt gct ggg acc aag ctg gag ctg aaa                            318
Phe Gly Ala Gly Thr Lys Leu Glu Leu Lys
            100                 105

<210> SEQ ID NO 12
<211> LENGTH: 106
<212> TYPE: PRT
<213> ORGANISM: Artificial Sequence
<220> FEATURE:
<223> OTHER INFORMATION: Synthetic Construct

<400> SEQUENCE: 12

Gln Ile Val Leu Thr Gln Ser Pro Ala Ile Met Ser Ala Ser Pro Gly
1               5                   10                  15

Glu Lys Val Ala Met Thr Cys Ser Ala Arg Ser Ser Val Ser Tyr Leu
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ile Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Asp Tyr Pro Leu Thr
                85                  90                  95

Phe Gly Ala Gly Thr Lys Leu Glu Leu Lys
            100                 105

<210> SEQ ID NO 13
<211> LENGTH: 318
<212> TYPE: DNA
<213> ORGANISM: Artificial Sequence
<220> FEATURE:
<223> OTHER INFORMATION: Light Chain VK4
<220> FEATURE:
<221> NAME/KEY: CDS
<222> LOCATION: (1)..(318)

<400> SEQUENCE: 13

```
caa att gtt ctc acc cag tct cca gca atc ctg tct gca tct cca ggg      48
Gln Ile Val Leu Thr Gln Ser Pro Ala Ile Leu Ser Ala Ser Pro Gly
1               5                   10                  15 gag aag gcc gcc atg acc tgc agt gcc agg tca agt gta agt tac ttg      96
Glu Lys Ala Ala Met Thr Cys Ser Ala Arg Ser Ser Val Ser Tyr Leu
                20                  25                  30 tac tgg tac cag cag aag cca ggg tcc tcc ccc aga ctc ctg att tat     144
Tyr Trp Tyr Gln Gln Lys Pro Gly Ser Ser Pro Arg Leu Leu Ile Tyr
            35                  40                  45 gac aca tcc aac ctg gct tct gga gtc cct tct cgc ttc att ggc agt     192
Asp Thr Ser Asn Leu Ala Ser Gly Val Pro Ser Arg Phe Ile Gly Ser
        50                  55                  60 ggg tct ggg acc gat tac tct ctc aca atc agc agc atg gag gct gaa     240
Gly Ser Gly Thr Asp Tyr Ser Leu Thr Ile Ser Ser Met Glu Ala Glu
65                  70                  75                  80 gat gct gcc act tat tac tgc cag cag tgg agt gat tac ccg ctc acg     288
Asp Ala Ala Thr Tyr Tyr Cys Gln Gln Trp Ser Asp Tyr Pro Leu Thr
                85                  90                  95 ttc ggt gct ggg acc aag ctg gag atc aaa                             318
Phe Gly Ala Gly Thr Lys Leu Glu Ile Lys
                100             105
```

<210> SEQ ID NO 14
<211> LENGTH: 106
<212> TYPE: PRT
<213> ORGANISM: Artificial Sequence
<220> FEATURE:
<223> OTHER INFORMATION: Synthetic Construct

<400> SEQUENCE: 14

```
Gln Ile Val Leu Thr Gln Ser Pro Ala Ile Leu Ser Ala Ser Pro Gly
1               5                   10                  15

Glu Lys Ala Ala Met Thr Cys Ser Ala Arg Ser Ser Val Ser Tyr Leu
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Ser Arg Phe Ile Gly Ser
        50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ser Asp Tyr Pro Leu Thr
                85                  90                  95

Phe Gly Ala Gly Thr Lys Leu Glu Ile Lys
                100             105
```

<210> SEQ ID NO 15
<211> LENGTH: 318
<212> TYPE: DNA
<213> ORGANISM: Artificial Sequence
<220> FEATURE:
<223> OTHER INFORMATION: Light chain VK3

```
<220> FEATURE:
<221> NAME/KEY: CDS
<222> LOCATION: (1)..(318)

<400> SEQUENCE: 15 caa att gtt ctc acc cag tct cca gca acc ctg tct gca tct cca ggg      48
Gln Ile Val Leu Thr Gln Ser Pro Ala Thr Leu Ser Ala Ser Pro Gly
1               5                   10                  15 gag aag gcc gcc atg acc tgc agt gcc agg tca agt gta agt tac ttg      96
Glu Lys Ala Ala Met Thr Cys Ser Ala Arg Ser Ser Val Ser Tyr Leu
            20                  25                  30 tac tgg tac cag cag aag cca ggg tcc tcc ccc aga ctc ctg att tat     144
Tyr Trp Tyr Gln Gln Lys Pro Gly Ser Ser Pro Arg Leu Leu Ile Tyr
        35                  40                  45 gac aca tcc aac ctg gct tct gga gtc cct tct cgc ttc att ggc agt     192
Asp Thr Ser Asn Leu Ala Ser Gly Val Pro Ser Arg Phe Ile Gly Ser
    50                  55                  60 ggg tct ggg acc gat tac tct ctc aca atc agc agc atg gag gct gaa     240
Gly Ser Gly Thr Asp Tyr Ser Leu Thr Ile Ser Ser Met Glu Ala Glu
65                  70                  75                  80 gat gct gcc act tat tac tgc cag cag tgg agt gat tac ccg ctc acg     288
Asp Ala Ala Thr Tyr Tyr Cys Gln Gln Trp Ser Asp Tyr Pro Leu Thr
                85                  90                  95 ttc ggt gct ggg acc aag ctg gag atc aaa                             318
Phe Gly Ala Gly Thr Lys Leu Glu Ile Lys
            100                 105

<210> SEQ ID NO 16
<211> LENGTH: 106
<212> TYPE: PRT
<213> ORGANISM: Artificial Sequence
<220> FEATURE:
<223> OTHER INFORMATION: Synthetic Construct

<400> SEQUENCE: 16

Gln Ile Val Leu Thr Gln Ser Pro Ala Thr Leu Ser Ala Ser Pro Gly
1               5                   10                  15

Glu Lys Ala Ala Met Thr Cys Ser Ala Arg Ser Ser Val Ser Tyr Leu
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Ser Arg Phe Ile Gly Ser
    50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ser Asp Tyr Pro Leu Thr
                85                  90                  95

Phe Gly Ala Gly Thr Lys Leu Glu Ile Lys
            100                 105

<210> SEQ ID NO 17
<211> LENGTH: 318
<212> TYPE: DNA
<213> ORGANISM: Artificial Sequence
<220> FEATURE:
<223> OTHER INFORMATION: Light chain VK2
<220> FEATURE:
<221> NAME/KEY: CDS
<222> LOCATION: (1)..(318)
```

<400> SEQUENCE: 17

```
caa att gtt ctc acc cag tct cca gca acc ctg tct gca tct cca ggg      48
Gln Ile Val Leu Thr Gln Ser Pro Ala Thr Leu Ser Ala Ser Pro Gly
1               5                   10                  15 gag aag gcc gcc atg acc tgc agt gcc agg tca agt gta agt tac ttg      96
Glu Lys Ala Ala Met Thr Cys Ser Ala Arg Ser Ser Val Ser Tyr Leu
            20                  25                  30 tac tgg tac cag cag aag cca ggg tcc tcc ccc aga ctc ctg att tat     144
Tyr Trp Tyr Gln Gln Lys Pro Gly Ser Ser Pro Arg Leu Leu Ile Tyr
        35                  40                  45 gac aca tcc aac ctg gct tct gga gtc cct tct cgc ttc agc ggc agt     192
Asp Thr Ser Asn Leu Ala Ser Gly Val Pro Ser Arg Phe Ser Gly Ser
    50                  55                  60 ggg tct ggg acc gat tac tct ctc aca atc agc agc atg gag gct gaa     240
Gly Ser Gly Thr Asp Tyr Ser Leu Thr Ile Ser Ser Met Glu Ala Glu
65                  70                  75                  80 gat gct gcc act tat tac tgc cag cag tgg agt gat tac ccg ctc acg     288
Asp Ala Ala Thr Tyr Tyr Cys Gln Gln Trp Ser Asp Tyr Pro Leu Thr
                85                  90                  95 ttc ggt gct ggg acc aag ctg gag atc aaa                             318
Phe Gly Ala Gly Thr Lys Leu Glu Ile Lys
            100                 105
```

<210> SEQ ID NO 18
<211> LENGTH: 106
<212> TYPE: PRT
<213> ORGANISM: Artificial Sequence
<220> FEATURE:
<223> OTHER INFORMATION: Synthetic Construct

<400> SEQUENCE: 18

```
Gln Ile Val Leu Thr Gln Ser Pro Ala Thr Leu Ser Ala Ser Pro Gly
1               5                   10                  15

Glu Lys Ala Ala Met Thr Cys Ser Ala Arg Ser Ser Val Ser Tyr Leu
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ser Asp Tyr Pro Leu Thr
                85                  90                  95

Phe Gly Ala Gly Thr Lys Leu Glu Ile Lys
            100                 105
```

<210> SEQ ID NO 19
<211> LENGTH: 318
<212> TYPE: DNA
<213> ORGANISM: Artificial Sequence
<220> FEATURE:
<223> OTHER INFORMATION: Light chain VK1
<220> FEATURE:
<221> NAME/KEY: CDS
<222> LOCATION: (1)..(318)

<400> SEQUENCE: 19

```
caa att gtt ctc acc cag tct cca gca acc ctg tct gca tct cca ggg      48
Gln Ile Val Leu Thr Gln Ser Pro Ala Thr Leu Ser Ala Ser Pro Gly
1               5                   10                  15 gag aag gcc gcc atg acc tgc agt gcc agg tca agt gta agt tac ttg      96
```

```
                Glu Lys Ala Ala Met Thr Cys Ser Ala Arg Ser Ser Val Ser Tyr Leu
                                20                  25                  30 tac tgg tac cag cag aag cca ggg tcc tcc ccc aga gcc ctg att tat        144
Tyr Trp Tyr Gln Gln Lys Pro Gly Ser Ser Pro Arg Ala Leu Ile Tyr
            35                  40                  45 gac aca tcc aac ctg gct tct gga gtc cct tct cgc ttc agc ggc agt        192
Asp Thr Ser Asn Leu Ala Ser Gly Val Pro Ser Arg Phe Ser Gly Ser
 50                  55                  60 ggg tct ggg acc gat tac tct ctc aca atc agc agc atg gag gct gaa        240
Gly Ser Gly Thr Asp Tyr Ser Leu Thr Ile Ser Ser Met Glu Ala Glu
 65                  70                  75                  80 gat gct gcc act tat tac tgc cag cag tgg agt gat tac ccg ctc acg        288
Asp Ala Ala Thr Tyr Tyr Cys Gln Gln Trp Ser Asp Tyr Pro Leu Thr
                85                  90                  95 ttc ggt gct ggg acc aag ctg gag atc aaa                                318
Phe Gly Ala Gly Thr Lys Leu Glu Ile Lys
               100                 105

<210> SEQ ID NO 20
<211> LENGTH: 106
<212> TYPE: PRT
<213> ORGANISM: Artificial Sequence
<220> FEATURE:
<223> OTHER INFORMATION: Synthetic Construct

<400> SEQUENCE: 20

Gln Ile Val Leu Thr Gln Ser Pro Ala Thr Leu Ser Ala Ser Pro Gly
 1               5                  10                  15

Glu Lys Ala Ala Met Thr Cys Ser Ala Arg Ser Ser Val Ser Tyr Leu
                20                  25                  30

Tyr Trp Tyr Gln Gln Lys Pro Gly Ser Ser Pro Arg Ala Leu Ile Tyr
            35                  40                  45

Asp Thr Ser Asn Leu Ala Ser Gly Val Pro Ser Arg Phe Ser Gly Ser
 50                  55                  60

Gly Ser Gly Thr Asp Tyr Ser Leu Thr Ile Ser Ser Met Glu Ala Glu
 65                  70                  75                  80

Asp Ala Ala Thr Tyr Tyr Cys Gln Gln Trp Ser Asp Tyr Pro Leu Thr
                85                  90                  95

Phe Gly Ala Gly Thr Lys Leu Glu Ile Lys
               100                 105

<210> SEQ ID NO 21
<211> LENGTH: 9
<212> TYPE: PRT
<213> ORGANISM: Artificial Sequence
<220> FEATURE:
<223> OTHER INFORMATION: epitope

<400> SEQUENCE: 21

Leu Gln Gln Ser Gly Thr Val Leu Ala
 1               5

<210> SEQ ID NO 22
<211> LENGTH: 9
<212> TYPE: PRT
<213> ORGANISM: Artificial Sequence
<220> FEATURE:
<223> OTHER INFORMATION: epitope

<400> SEQUENCE: 22

Val Leu Ala Arg Pro Gly Ala Ser Val
 1               5
```

```
<210> SEQ ID NO 23
<211> LENGTH: 9
<212> TYPE: PRT
<213> ORGANISM: Artificial Sequence
<220> FEATURE:
<223> OTHER INFORMATION: epitope

<400> SEQUENCE: 23

Leu Ala Arg Pro Gly Ala Ser Val Gln
1               5

<210> SEQ ID NO 24
<211> LENGTH: 9
<212> TYPE: PRT
<213> ORGANISM: Artificial Sequence
<220> FEATURE:
<223> OTHER INFORMATION: epitope

<400> SEQUENCE: 24

Met Ser Cys Lys Ala Ser Gly Tyr Ser
1               5

<210> SEQ ID NO 25
<211> LENGTH: 9
<212> TYPE: PRT
<213> ORGANISM: Artificial Sequence
<220> FEATURE:
<223> OTHER INFORMATION: epitope

<400> SEQUENCE: 25

Val Lys Gln Arg Pro Gly Gln Gly Leu
1               5

<210> SEQ ID NO 26
<211> LENGTH: 9
<212> TYPE: PRT
<213> ORGANISM: Artificial Sequence
<220> FEATURE:
<223> OTHER INFORMATION: epitope

<400> SEQUENCE: 26

Leu Thr Ala Val Thr Ser Ala Ser Thr
1               5

<210> SEQ ID NO 27
<211> LENGTH: 9
<212> TYPE: PRT
<213> ORGANISM: Artificial Sequence
<220> FEATURE:
<223> OTHER INFORMATION: epitope

<400> SEQUENCE: 27

Val Thr Ser Ala Ser Thr Ala Tyr Met
1               5

<210> SEQ ID NO 28
<211> LENGTH: 9
<212> TYPE: PRT
<213> ORGANISM: Artificial Sequence
<220> FEATURE:
<223> OTHER INFORMATION: epitope

<400> SEQUENCE: 28

Leu Ser Ser Leu Thr Asn Glu Asp Ser
1               5
```

<210> SEQ ID NO 29
<211> LENGTH: 9
<212> TYPE: PRT
<213> ORGANISM: Artificial Sequence
<220> FEATURE:
<223> OTHER INFORMATION: epitope

<400> SEQUENCE: 29

Leu Asp Tyr Trp Gly Gln Gly Thr Thr
1               5

<210> SEQ ID NO 30
<211> LENGTH: 9
<212> TYPE: PRT
<213> ORGANISM: Artificial Sequence
<220> FEATURE:
<223> OTHER INFORMATION: epitope

<400> SEQUENCE: 30

Trp Gly Gln Gly Thr Thr Leu Thr Val
1               5

<210> SEQ ID NO 31
<211> LENGTH: 9
<212> TYPE: PRT
<213> ORGANISM: Artificial Sequence
<220> FEATURE:
<223> OTHER INFORMATION: epitope

<400> SEQUENCE: 31

Ile Val Leu Thr Gln Ser Pro Ala Ile
1               5

<210> SEQ ID NO 32
<211> LENGTH: 9
<212> TYPE: PRT
<213> ORGANISM: Artificial Sequence
<220> FEATURE:
<223> OTHER INFORMATION: epitope

<400> SEQUENCE: 32

Val Leu Thr Gln Ser Pro Ala Ile Met
1               5

<210> SEQ ID NO 33
<211> LENGTH: 9
<212> TYPE: PRT
<213> ORGANISM: Artificial Sequence
<220> FEATURE:
<223> OTHER INFORMATION: epitope

<400> SEQUENCE: 33

Ile Met Ser Ala Ser Pro Gly Glu Lys
1               5

<210> SEQ ID NO 34
<211> LENGTH: 9
<212> TYPE: PRT
<213> ORGANISM: Artificial Sequence
<220> FEATURE:
<223> OTHER INFORMATION: epitope

<400> SEQUENCE: 34

Met Ser Ala Ser Pro Gly Glu Lys Val
1               5

```
<210> SEQ ID NO 35
<211> LENGTH: 9
<212> TYPE: PRT
<213> ORGANISM: Artificial Sequence
<220> FEATURE:
<223> OTHER INFORMATION: epitope

<400> SEQUENCE: 35

Leu Leu Ile Tyr Asp Thr Ser Asn Leu
1               5

<210> SEQ ID NO 36
<211> LENGTH: 9
<212> TYPE: PRT
<213> ORGANISM: Artificial Sequence
<220> FEATURE:
<223> OTHER INFORMATION: epitope

<400> SEQUENCE: 36

Leu Ala Ser Gly Val Pro Val Arg Phe
1               5

<210> SEQ ID NO 37
<211> LENGTH: 9
<212> TYPE: PRT
<213> ORGANISM: Artificial Sequence
<220> FEATURE:
<223> OTHER INFORMATION: epitope

<400> SEQUENCE: 37

Val Arg Phe Ile Gly Ser Gly Ser Gly
1               5

<210> SEQ ID NO 38
<211> LENGTH: 9
<212> TYPE: PRT
<213> ORGANISM: Artificial Sequence
<220> FEATURE:
<223> OTHER INFORMATION: epitope

<400> SEQUENCE: 38

Phe Ile Gly Ser Gly Ser Gly Thr Ser
1               5

<210> SEQ ID NO 39
<211> LENGTH: 9
<212> TYPE: PRT
<213> ORGANISM: Artificial Sequence
<220> FEATURE:
<223> OTHER INFORMATION: epitope

<400> SEQUENCE: 39

Ile Gly Ser Gly Ser Gly Thr Ser Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: epitope

<400> SEQUENCE: 40

Tyr Ser Leu Thr Ile Ser Arg Met Glu
1               5

<210> SEQ ID NO 41
```

```
<211> LENGTH: 9
<212> TYPE: PRT
<213> ORGANISM: Artificial Sequence
<220> FEATURE:
<223> OTHER INFORMATION: epitope

<400> SEQUENCE: 41

Phe Gly Ala Gly Thr Lys Leu Glu Leu
1               5

<210> SEQ ID NO 42
<211> LENGTH: 9
<212> TYPE: PRT
<213> ORGANISM: Artificial Sequence
<220> FEATURE:
<223> OTHER INFORMATION: epitope

<400> SEQUENCE: 42

Leu Gln Gln Ser Gly Thr Glu Leu Lys
1               5

<210> SEQ ID NO 43
<211> LENGTH: 9
<212> TYPE: PRT
<213> ORGANISM: Artificial Sequence
<220> FEATURE:
<223> OTHER INFORMATION: epitope

<400> SEQUENCE: 43

Leu Gln Gln Ser Gly Ser Glu Leu Lys
1               5

<210> SEQ ID NO 44
<211> LENGTH: 9
<212> TYPE: PRT
<213> ORGANISM: Artificial Sequence
<220> FEATURE:
<223> OTHER INFORMATION: epitope

<400> SEQUENCE: 44

Glu Leu Lys Arg Pro Gly Ala Ser Val
1               5

<210> SEQ ID NO 45
<211> LENGTH: 9
<212> TYPE: PRT
<213> ORGANISM: Artificial Sequence
<220> FEATURE:
<223> OTHER INFORMATION: epitope

<400> SEQUENCE: 45

Leu Lys Arg Pro Gly Ala Ser Val Lys
1               5

<210> SEQ ID NO 46
<211> LENGTH: 9
<212> TYPE: PRT
<213> ORGANISM: Artificial Sequence
<220> FEATURE:
<223> OTHER INFORMATION: epitope

<400> SEQUENCE: 46

Met Ser Cys Lys Ala Ser Gly Tyr Thr
1               5

<210> SEQ ID NO 47
<211> LENGTH: 9
```

```
<212> TYPE: PRT
<213> ORGANISM: Artificial Sequence
<220> FEATURE:
<223> OTHER INFORMATION: epitope

<400> SEQUENCE: 47

Val Ser Cys Lys Ala Ser Gly Tyr Thr
1               5

<210> SEQ ID NO 48
<211> LENGTH: 9
<212> TYPE: PRT
<213> ORGANISM: Artificial Sequence
<220> FEATURE:
<223> OTHER INFORMATION: epitope

<400> SEQUENCE: 48

Val Lys Gln Ala Pro Gly Gln Gly Leu
1               5

<210> SEQ ID NO 49
<211> LENGTH: 9
<212> TYPE: PRT
<213> ORGANISM: Artificial Sequence
<220> FEATURE:
<223> OTHER INFORMATION: epitope

<400> SEQUENCE: 49

Leu Thr Ala Asp Thr Ser Ala Ser Thr
1               5

<210> SEQ ID NO 50
<211> LENGTH: 9
<212> TYPE: PRT
<213> ORGANISM: Artificial Sequence
<220> FEATURE:
<223> OTHER INFORMATION: epitope

<400> SEQUENCE: 50

Ile Thr Arg Asp Thr Ser Ala Ser Thr
1               5

<210> SEQ ID NO 51
<211> LENGTH: 9
<212> TYPE: PRT
<213> ORGANISM: Artificial Sequence
<220> FEATURE:
<223> OTHER INFORMATION: epitope

<400> SEQUENCE: 51

Asp Thr Ser Ala Ser Thr Ala Tyr Met
1               5

<210> SEQ ID NO 52
<211> LENGTH: 9
<212> TYPE: PRT
<213> ORGANISM: Artificial Sequence
<220> FEATURE:
<223> OTHER INFORMATION: epitope

<400> SEQUENCE: 52

Leu Ser Ser Leu Thr Asn Glu Asp Thr
1               5

<210> SEQ ID NO 53
<211> LENGTH: 9
<212> TYPE: PRT
```

```
<213> ORGANISM: Artificial Sequence
<220> FEATURE:
<223> OTHER INFORMATION: epitope

<400> SEQUENCE: 53

Leu Asp Tyr Trp Gly Gln Gly Thr Leu
1               5

<210> SEQ ID NO 54
<211> LENGTH: 9
<212> TYPE: PRT
<213> ORGANISM: Artificial Sequence
<220> FEATURE:
<223> OTHER INFORMATION: epitope

<400> SEQUENCE: 54

Trp Gly Gln Gly Thr Thr Val Thr Val
1               5

<210> SEQ ID NO 55
<211> LENGTH: 9
<212> TYPE: PRT
<213> ORGANISM: Artificial Sequence
<220> FEATURE:
<223> OTHER INFORMATION: epitope

<400> SEQUENCE: 55

Trp Gly Gln Gly Thr Leu Val Thr Val
1               5

<210> SEQ ID NO 56
<211> LENGTH: 9
<212> TYPE: PRT
<213> ORGANISM: Artificial Sequence
<220> FEATURE:
<223> OTHER INFORMATION: epitope

<400> SEQUENCE: 56

Ile Val Leu Thr Gln Ser Pro Ala Thr
1               5

<210> SEQ ID NO 57
<211> LENGTH: 9
<212> TYPE: PRT
<213> ORGANISM: Artificial Sequence
<220> FEATURE:
<223> OTHER INFORMATION: epitope

<400> SEQUENCE: 57

Val Leu Thr Gln Ser Pro Ala Thr Leu
1               5

<210> SEQ ID NO 58
<211> LENGTH: 9
<212> TYPE: PRT
<213> ORGANISM: Artificial Sequence
<220> FEATURE:
<223> OTHER INFORMATION: epitope

<400> SEQUENCE: 58

Thr Leu Ser Ala Ser Pro Gly Glu Lys
1               5

<210> SEQ ID NO 59
<211> LENGTH: 9
<212> TYPE: PRT
<213> ORGANISM: Artificial Sequence
```

```
<220> FEATURE:
<223> OTHER INFORMATION: epitope

<400> SEQUENCE: 59

Leu Ser Ala Ser Pro Gly Glu Lys Val
1               5

<210> SEQ ID NO 60
<211> LENGTH: 9
<212> TYPE: PRT
<213> ORGANISM: Artificial Sequence
<220> FEATURE:
<223> OTHER INFORMATION: epitope

<400> SEQUENCE: 60

Ala Leu Ile Tyr Asp Thr Ser Asn Leu
1               5

<210> SEQ ID NO 61
<211> LENGTH: 9
<212> TYPE: PRT
<213> ORGANISM: Artificial Sequence
<220> FEATURE:
<223> OTHER INFORMATION: epitope

<400> SEQUENCE: 61

Leu Ala Ser Gly Val Pro Ser Arg Phe
1               5

<210> SEQ ID NO 62
<211> LENGTH: 9
<212> TYPE: PRT
<213> ORGANISM: Artificial Sequence
<220> FEATURE:
<223> OTHER INFORMATION: epitope

<400> SEQUENCE: 62

Ser Arg Phe Ile Gly Ser Gly Ser Gly
1               5

<210> SEQ ID NO 63
<211> LENGTH: 9
<212> TYPE: PRT
<213> ORGANISM: Artificial Sequence
<220> FEATURE:
<223> OTHER INFORMATION: epitope

<400> SEQUENCE: 63

Ser Arg Phe Ser Gly Ser Gly Ser Gly
1               5

<210> SEQ ID NO 64
<211> LENGTH: 9
<212> TYPE: PRT
<213> ORGANISM: Artificial Sequence
<220> FEATURE:
<223> OTHER INFORMATION: epitope

<400> SEQUENCE: 64

Phe Ile Gly Ser Gly Ser Gly Thr Asp
1               5

<210> SEQ ID NO 65
<211> LENGTH: 9
<212> TYPE: PRT
<213> ORGANISM: Artificial Sequence
<220> FEATURE:
```

<223> OTHER INFORMATION: epitope

<400> SEQUENCE: 65

Phe Ser Gly Ser Gly Ser Gly Thr Asp
1               5

<210> SEQ ID NO 66
<211> LENGTH: 9
<212> TYPE: PRT
<213> ORGANISM: Artificial Sequence
<220> FEATURE:
<223> OTHER INFORMATION: epitope

<400> SEQUENCE: 66

Ile Gly Ser Gly Ser Gly Thr Asp Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: epitope

<400> SEQUENCE: 67

Ser Gly Ser Gly Ser Gly Thr Asp Tyr
1               5

<210> SEQ ID NO 68
<211> LENGTH: 9
<212> TYPE: PRT
<213> ORGANISM: Artificial Sequence
<220> FEATURE:
<223> OTHER INFORMATION: epitope

<400> SEQUENCE: 68

Tyr Ser Leu Thr Ile Ser Ser Met Glu
1               5

<210> SEQ ID NO 69
<211> LENGTH: 9
<212> TYPE: PRT
<213> ORGANISM: Artificial Sequence
<220> FEATURE:
<223> OTHER INFORMATION: epitope

<400> SEQUENCE: 69

Phe Gly Ala Gly Thr Lys Leu Glu Ile
1               5

<210> SEQ ID NO 70
<211> LENGTH: 25
<212> TYPE: DNA
<213> ORGANISM: Artificial Sequence
<220> FEATURE:
<223> OTHER INFORMATION: primer

<400> SEQUENCE: 70
atgrasttsk ggytmarctk grttt                                    25

<210> SEQ ID NO 71
<211> LENGTH: 26
<212> TYPE: DNA
<213> ORGANISM: Artificial Sequence
<220> FEATURE:
<223> OTHER INFORMATION: primer

<400> SEQUENCE: 71
atgraatgsa sctgggtywt yctctt                                          26

<210> SEQ ID NO 72
<211> LENGTH: 29
<212> TYPE: DNA
<213> ORGANISM: Artificial Sequence
<220> FEATURE:
<223> OTHER INFORMATION: primer

<400> SEQUENCE: 72
atggactcca ggctcaattt agttttcct                                       29

<210> SEQ ID NO 73
<211> LENGTH: 26
<212> TYPE: DNA
<213> ORGANISM: Artificial Sequence
<220> FEATURE:
<223> OTHER INFORMATION: primer

<400> SEQUENCE: 73
atggctgtcy trgbgctgyt cytctg                                          26

<210> SEQ ID NO 74
<211> LENGTH: 29
<212> TYPE: DNA
<213> ORGANISM: Artificial Sequence
<220> FEATURE:
<223> OTHER INFORMATION: primer

<400> SEQUENCE: 74
atggvttggs tgtggamctt gcyattcct                                       29

<210> SEQ ID NO 75
<211> LENGTH: 26
<212> TYPE: DNA
<213> ORGANISM: Artificial Sequence
<220> FEATURE:
<223> OTHER INFORMATION: primer

<400> SEQUENCE: 75
atgaaatgca gctggrtyat sttctt                                          26

<210> SEQ ID NO 76
<211> LENGTH: 26
<212> TYPE: DNA
<213> ORGANISM: Artificial Sequence
<220> FEATURE:
<223> OTHER INFORMATION: primer

<400> SEQUENCE: 76
atggrcagrc ttacwtyytc attcct                                          26

<210> SEQ ID NO 77
<211> LENGTH: 26
<212> TYPE: DNA
<213> ORGANISM: Artificial Sequence
<220> FEATURE:
<223> OTHER INFORMATION: primer

<400> SEQUENCE: 77
atgatggtgt taagtcttct gtacct                                          26

<210> SEQ ID NO 78
<211> LENGTH: 26

```
<212> TYPE: DNA
<213> ORGANISM: Artificial Sequence
<220> FEATURE:
<223> OTHER INFORMATION: primer

<400> SEQUENCE: 78
atgggatgga gctrtatcat sytctt                                              26

<210> SEQ ID NO 79
<211> LENGTH: 23
<212> TYPE: DNA
<213> ORGANISM: Artificial Sequence
<220> FEATURE:
<223> OTHER INFORMATION: primer

<400> SEQUENCE: 79
atgaagwtgt ggbtraactg grt                                                 23

<210> SEQ ID NO 80
<211> LENGTH: 25
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (15)..(15)
<223> OTHER INFORMATION: I

<400> SEQUENCE: 80
atggratgga sckkrrtctt tmtct                                               25

<210> SEQ ID NO 81
<211> LENGTH: 25
<212> TYPE: DNA
<213> ORGANISM: Artificial Sequence
<220> FEATURE:
<223> OTHER INFORMATION: primer

<400> SEQUENCE: 81
atgaacttyg ggytsagmtt grttt                                               25

<210> SEQ ID NO 82
<211> LENGTH: 25
<212> TYPE: DNA
<213> ORGANISM: Artificial Sequence
<220> FEATURE:
<223> OTHER INFORMATION: primer

<400> SEQUENCE: 82
atgtacttgg gactgagctg tgtat                                               25

<210> SEQ ID NO 83
<211> LENGTH: 23
<212> TYPE: DNA
<213> ORGANISM: Artificial Sequence
<220> FEATURE:
<223> OTHER INFORMATION: primer

<400> SEQUENCE: 83
atgagagtgc tgattctttt gtg                                                 23

<210> SEQ ID NO 84
<211> LENGTH: 28
<212> TYPE: DNA
<213> ORGANISM: Artificial Sequence
<220> FEATURE:
```

<223> OTHER INFORMATION: primer

<400> SEQUENCE: 84
atggattttg ggctgattttt ttttattg                                    28

<210> SEQ ID NO 85
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (21)..(21)
<223> OTHER INFORMATION: I

<400> SEQUENCE: 85
ccagggrcca rkggatarac rgrtgg                                       26

<210> SEQ ID NO 86
<211> LENGTH: 24
<212> TYPE: DNA
<213> ORGANISM: Artificial Sequence
<220> FEATURE:
<223> OTHER INFORMATION: primer

<400> SEQUENCE: 86
atgragwcac akwcycaggt cttt                                         24

<210> SEQ ID NO 87
<211> LENGTH: 25
<212> TYPE: DNA
<213> ORGANISM: Artificial Sequence
<220> FEATURE:
<223> OTHER INFORMATION: primer

<400> SEQUENCE: 87
atggagacag acacactcct gctat                                        25

<210> SEQ ID NO 88
<211> LENGTH: 29
<212> TYPE: DNA
<213> ORGANISM: Artificial Sequence
<220> FEATURE:
<223> OTHER INFORMATION: primer

<400> SEQUENCE: 88
atggagwcag acacactsct gytatgggt                                    29

<210> SEQ ID NO 89
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (27)..(27)
<223> OTHER INFORMATION: I

<400> SEQUENCE: 89
atgaggrccc ctgctcagwt tyttggrwtc tt                                32

<210> SEQ ID NO 90
<211> LENGTH: 31
<212> TYPE: DNA
<213> ORGANISM: Artificial Sequence
<220> FEATURE:
<223> OTHER INFORMATION: primer

<400> SEQUENCE: 90
atgggcwtca agatgragtc acakwyycwg g                                    31

<210> SEQ ID NO 91
<211> LENGTH: 29
<212> TYPE: DNA
<213> ORGANISM: Artificial Sequence
<220> FEATURE:
<223> OTHER INFORMATION: primer

<400> SEQUENCE: 91
atgagtgtgc ycactcaggt cctggsgtt                                       29

<210> SEQ ID NO 92
<211> LENGTH: 31
<212> TYPE: DNA
<213> ORGANISM: Artificial Sequence
<220> FEATURE:
<223> OTHER INFORMATION: primer

<400> SEQUENCE: 92
atgtggggay cgktttyamm cttttcaatt g                                    31

<210> SEQ ID NO 93
<211> LENGTH: 28
<212> TYPE: DNA
<213> ORGANISM: Artificial Sequence
<220> FEATURE:
<223> OTHER INFORMATION: primer

<400> SEQUENCE: 93
atggaagccc cagctcagct tctcttcc                                        28

<210> SEQ ID NO 94
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (12)..(12)
<223> OTHER INFORMATION: I
<220> FEATURE:
<221> NAME/KEY: modified_base
<222> LOCATION: (18)..(18)
<223> OTHER INFORMATION: I

<400> SEQUENCE: 94
atgagrmmkt crmttcartt cytggg                                          26

<210> SEQ ID NO 95
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (12)..(12)
<223> OTHER INFORMATION: I
<220> FEATURE:

```
<221> NAME/KEY: modified_base
<222> LOCATION: (24)..(24)
<223> OTHER INFORMATION: I

<400> SEQUENCE: 95
atgakgthcy crgctcagyt yctrrg                                          26

<210> SEQ ID NO 96
<211> LENGTH: 25
<212> TYPE: DNA
<213> ORGANISM: Artificial Sequence
<220> FEATURE:
<223> OTHER INFORMATION: primer

<400> SEQUENCE: 96
atggtrtccw casctcagtt ccttg                                           25

<210> SEQ ID NO 97
<211> LENGTH: 27
<212> TYPE: DNA
<213> ORGANISM: Artificial Sequence
<220> FEATURE:
<223> OTHER INFORMATION: primer

<400> SEQUENCE: 97
atgtatatat gtttgttgtc tatttct                                         27

<210> SEQ ID NO 98
<211> LENGTH: 29
<212> TYPE: DNA
<213> ORGANISM: Artificial Sequence
<220> FEATURE:
<223> OTHER INFORMATION: primer

<400> SEQUENCE: 98
atgaagttgc ctgttaggct gttggtgct                                       29

<210> SEQ ID NO 99
<211> LENGTH: 29
<212> TYPE: DNA
<213> ORGANISM: Artificial Sequence
<220> FEATURE:
<223> OTHER INFORMATION: primer

<400> SEQUENCE: 99
atggatttwc argtgcagat twtcagctt                                       29

<210> SEQ ID NO 100
<211> LENGTH: 27
<212> TYPE: DNA
<213> ORGANISM: Artificial Sequence
<220> FEATURE:
<223> OTHER INFORMATION: primer

<400> SEQUENCE: 100
atggtyctya tvtccttgct gttctgg                                         27

<210> SEQ ID NO 101
<211> LENGTH: 27
<212> TYPE: DNA
<213> ORGANISM: Artificial Sequence
<220> FEATURE:
<223> OTHER INFORMATION: primer

<400> SEQUENCE: 101
atggtyctya tvttrctgct gctatgg                                         27
```

<210> SEQ ID NO 102
<211> LENGTH: 21
<212> TYPE: DNA
<213> ORGANISM: Artificial Sequence
<220> FEATURE:
<223> OTHER INFORMATION: primer

<400> SEQUENCE: 102
actggatggt gggaagatgg a                                                21

<210> SEQ ID NO 103
<211> LENGTH: 25
<212> TYPE: DNA
<213> ORGANISM: Artificial Sequence
<220> FEATURE:
<223> OTHER INFORMATION: primer

<400> SEQUENCE: 103
atggcctgga ytycwctywt mytct                                            25

<210> SEQ ID NO 104
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (15)..(15)
<223> OTHER INFORMATION: I

<400> SEQUENCE: 104
agctcytcwg wggarggygg raa                                              23

<210> SEQ ID NO 105
<211> LENGTH: 39
<212> TYPE: DNA
<213> ORGANISM: Artificial Sequence
<220> FEATURE:
<223> OTHER INFORMATION: primer

<400> SEQUENCE: 105
gatcacgcgt gtccactccg aagtgcagct ggtggagtc                             39

<210> SEQ ID NO 106
<211> LENGTH: 33
<212> TYPE: DNA
<213> ORGANISM: Artificial Sequence
<220> FEATURE:
<223> OTHER INFORMATION: primer

<400> SEQUENCE: 106
gtacaagctt acctgaggag acggtgactg agg                                   33

<210> SEQ ID NO 107
<211> LENGTH: 35
<212> TYPE: DNA
<213> ORGANISM: Artificial Sequence
<220> FEATURE:
<223> OTHER INFORMATION: primer

<400> SEQUENCE: 107
catggcgcgc gatgtgacat ccagatgact cagtc                                 35

<210> SEQ ID NO 108

```
<211> LENGTH: 63
<212> TYPE: DNA
<213> ORGANISM: Artificial Sequence
<220> FEATURE:
<223> OTHER INFORMATION: primer

<400> SEQUENCE: 108
tgcgggatcc aactgaggaa gcaaagttta aattctactc acgtctcagc tccagcttgg      60
tcc                                                                   63

<210> SEQ ID NO 109
<211> LENGTH: 65
<212> TYPE: DNA
<213> ORGANISM: Artificial Sequence
<220> FEATURE:
<223> OTHER INFORMATION: primer

<400> SEQUENCE: 109
gttgctacgc gtgtccactc cgaggttcag ctccagcagt ctgggactga gctgaaaagg      60
cctgg                                                                 65

<210> SEQ ID NO 110
<211> LENGTH: 65
<212> TYPE: DNA
<213> ORGANISM: Artificial Sequence
<220> FEATURE:
<223> OTHER INFORMATION: primer

<400> SEQUENCE: 110
actgagctga aaaggcctgg ggcttccgtg aagatgtcct gcaaggcttc tggctacacc      60
tttgc                                                                 65

<210> SEQ ID NO 111
<211> LENGTH: 21
<212> TYPE: DNA
<213> ORGANISM: Artificial Sequence
<220> FEATURE:
<223> OTHER INFORMATION: primer

<400> SEQUENCE: 111
acagggtcta caatggattg g                                               21

<210> SEQ ID NO 112
<211> LENGTH: 37
<212> TYPE: DNA
<213> ORGANISM: Artificial Sequence
<220> FEATURE:
<223> OTHER INFORMATION: primer

<400> SEQUENCE: 112
ccaatccatt gtagaccctg tccaggggcc tgtttta                              37

<210> SEQ ID NO 113
<211> LENGTH: 39
<212> TYPE: DNA
<213> ORGANISM: Artificial Sequence
<220> FEATURE:
<223> OTHER INFORMATION: primer

<400> SEQUENCE: 113
cccagaaagc ttacctgagg agactgtgac agtggtgcc                            39

<210> SEQ ID NO 114
<211> LENGTH: 60
```

```
<212> TYPE: DNA
<213> ORGANISM: Artificial Sequence
<220> FEATURE:
<223> OTHER INFORMATION: primer

<400> SEQUENCE: 114
gttgctacgc gtgtccactc cgaggttcag ctccagcagt ctgggtctga gctgaaaagg      60

<210> SEQ ID NO 115
<211> LENGTH: 24
<212> TYPE: DNA
<213> ORGANISM: Artificial Sequence
<220> FEATURE:
<223> OTHER INFORMATION: primer

<400> SEQUENCE: 115
caaatgagga caccgcggtc tatt                                             24

<210> SEQ ID NO 116
<211> LENGTH: 24
<212> TYPE: DNA
<213> ORGANISM: Artificial Sequence
<220> FEATURE:
<223> OTHER INFORMATION: primer

<400> SEQUENCE: 116
aatagaccgc ggtgtcctca tttg                                             24

<210> SEQ ID NO 117
<211> LENGTH: 39
<212> TYPE: DNA
<213> ORGANISM: Artificial Sequence
<220> FEATURE:
<223> OTHER INFORMATION: primer

<400> SEQUENCE: 117
cccagaaagc ttacctgagg agactgtgac aagggtgcc                             39

<210> SEQ ID NO 118
<211> LENGTH: 25
<212> TYPE: DNA
<213> ORGANISM: Artificial Sequence
<220> FEATURE:
<223> OTHER INFORMATION: primer

<400> SEQUENCE: 118
cttccgtgaa ggtgtcctgc aaggc                                            25

<210> SEQ ID NO 119
<211> LENGTH: 25
<212> TYPE: DNA
<213> ORGANISM: Artificial Sequence
<220> FEATURE:
<223> OTHER INFORMATION: primer

<400> SEQUENCE: 119
gccttgcagg acaccttcac ggaag                                            25

<210> SEQ ID NO 120
<211> LENGTH: 25
<212> TYPE: DNA
<213> ORGANISM: Artificial Sequence
<220> FEATURE:
<223> OTHER INFORMATION: primer

<400> SEQUENCE: 120
```
aactgactgc agacacatcc gccag                                           25

<210> SEQ ID NO 121
<211> LENGTH: 25
<212> TYPE: DNA
<213> ORGANISM: Artificial Sequence
<220> FEATURE:
<223> OTHER INFORMATION: primer

<400> SEQUENCE: 121
ctggcggatg tgtctgcagt cagtt                                           25

<210> SEQ ID NO 122
<211> LENGTH: 25
<212> TYPE: DNA
<213> ORGANISM: Artificial Sequence
<220> FEATURE:
<223> OTHER INFORMATION: primer

<400> SEQUENCE: 122
tgcactgggt aagacaggcc cctgg                                           25

<210> SEQ ID NO 123
<211> LENGTH: 25
<212> TYPE: DNA
<213> ORGANISM: Artificial Sequence
<220> FEATURE:
<223> OTHER INFORMATION: primer

<400> SEQUENCE: 123
ccaggggcct gtcttaccca gtgca                                           25

<210> SEQ ID NO 124
<211> LENGTH: 46
<212> TYPE: DNA
<213> ORGANISM: Artificial Sequence
<220> FEATURE:
<223> OTHER INFORMATION: primer

<400> SEQUENCE: 124
gttcaaggac aaggccaaaa tcactagaga cacatccgcc agcact                    46

<210> SEQ ID NO 125
<211> LENGTH: 46
<212> TYPE: DNA
<213> ORGANISM: Artificial Sequence
<220> FEATURE:
<223> OTHER INFORMATION: primer

<400> SEQUENCE: 125
agtgctggcg gatgtgtctc tagtgatttt ggccttgtcc ttgaac                    46

<210> SEQ ID NO 126
<211> LENGTH: 26
<212> TYPE: DNA
<213> ORGANISM: Artificial Sequence
<220> FEATURE:
<223> OTHER INFORMATION: primer

<400> SEQUENCE: 126
ctccagggga gaaggccgcc atgacc                                          26

<210> SEQ ID NO 127
<211> LENGTH: 26
<212> TYPE: DNA
<213> ORGANISM: Artificial Sequence
<220> FEATURE:
<223> OTHER INFORMATION: primer

<400> SEQUENCE: 127
ggtcatggcg gccttctccc ctggag   26

<210> SEQ ID NO 128
<211> LENGTH: 51
<212> TYPE: DNA
<213> ORGANISM: Artificial Sequence
<220> FEATURE:
<223> OTHER INFORMATION: primer

<400> SEQUENCE: 128
tcctgattta tgacacatcc aacctggctt ctggagtccc ttctcgcttc a   51

<210> SEQ ID NO 129
<211> LENGTH: 23
<212> TYPE: DNA
<213> ORGANISM: Artificial Sequence
<220> FEATURE:
<223> OTHER INFORMATION: primer

<400> SEQUENCE: 129
gttggatgtg tcataaatca gga   23

<210> SEQ ID NO 130
<211> LENGTH: 43
<212> TYPE: DNA
<213> ORGANISM: Artificial Sequence
<220> FEATURE:
<223> OTHER INFORMATION: primer

<400> SEQUENCE: 130
tctgggaccg attactctct cacaatcagc agcatggagg ctg   43

<210> SEQ ID NO 131
<211> LENGTH: 43
<212> TYPE: DNA
<213> ORGANISM: Artificial Sequence
<220> FEATURE:
<223> OTHER INFORMATION: primer

<400> SEQUENCE: 131
cagcctccat gctgctgatt gtgagagagt aatcggtccc aga   43

<210> SEQ ID NO 132
<211> LENGTH: 61
<212> TYPE: DNA
<213> ORGANISM: Artificial Sequence
<220> FEATURE:
<223> OTHER INFORMATION: primer

<400> SEQUENCE: 132
attgcgggat ccaactgagg aagcaaagtt taaattctac tcacgtttga tctccagctt   60
g   61

<210> SEQ ID NO 133
<211> LENGTH: 55
<212> TYPE: DNA
<213> ORGANISM: Artificial Sequence
<220> FEATURE:
<223> OTHER INFORMATION: primer

```
<400> SEQUENCE: 133
cccaggcgcg cgatgtcaaa ttgttctcac ccagtctcca gcaaccctgt ctgca        55

<210> SEQ ID NO 134
<211> LENGTH: 22
<212> TYPE: DNA
<213> ORGANISM: Artificial Sequence
<220> FEATURE:
<223> OTHER INFORMATION: primer

<400> SEQUENCE: 134
ttctcgcttc agcggcagtg gg                                            22

<210> SEQ ID NO 135
<211> LENGTH: 22
<212> TYPE: DNA
<213> ORGANISM: Artificial Sequence
<220> FEATURE:
<223> OTHER INFORMATION: primer

<400> SEQUENCE: 135
cccactgccg ctgaagcgag aa                                            22

<210> SEQ ID NO 136
<211> LENGTH: 22
<212> TYPE: DNA
<213> ORGANISM: Artificial Sequence
<220> FEATURE:
<223> OTHER INFORMATION: primer

<400> SEQUENCE: 136
ctcccccaga gccctgattt at                                            22

<210> SEQ ID NO 137
<211> LENGTH: 22
<212> TYPE: DNA
<213> ORGANISM: Artificial Sequence
<220> FEATURE:
<223> OTHER INFORMATION: primer

<400> SEQUENCE: 137
ataaatcagg gctctggggg ag                                            22

<210> SEQ ID NO 138
<211> LENGTH: 9
<212> TYPE: PRT
<213> ORGANISM: Artificial Sequence
<220> FEATURE:
<223> OTHER INFORMATION: epitope

<400> SEQUENCE: 138

Val Arg Gln Ala Pro Gly Gln Gly Leu
1               5
```

ANTI CD4 ANTIBODIES TO PREVENT IN PARTICULAR GRAFT-VERSUS-HOST-DISEASE (GVHD)

CROSS-REFERENCE TO RELATED APPLICATION

This application is the U.S. national stage filing under 35 U.S.C. §371 of International Application No. PCT/EP2011/006060, filed Dec. 2, 2011, which claims the benefit of the filing date of European Patent Application No. 10015236.2, filed Dec. 2, 2010.

The invention relates to the field of grafts and transplantations thereof. In particular, the invention relates to modified grafts, methods of obtaining same, as well as related uses. Among others, the invention relates to grafts containing immunocompetent viable cells.

In an additional aspect, the present invention relates to modified anti human CD4-antibodies, in which the immune characteristic is modified by means of a reduced number of T cell epitopes, and to related subject-matter.

BACKGROUND OF THE INVENTION

Today, allogeneic hematopoietic stem cell transplantation (HSCT) is the only curative treatment for many patients with hematological malignancies. Bone marrow (Aschan, 2006), peripheral mobilized stem cells (Bacigalupo et al., 2002) and umbilical cord blood (Kestendjieva et al., 2008) are the common sources for HSCT. Despite the use of highly sophisticated therapeutic approaches, HSCT is still associated with a considerable mortality caused by a number of complications such as graft versus host disease (GvHD), infectious diseases, veno-occlusive disease, donor graft rejection, and relapses of the underlying diseases.

The use of conventionally immunosuppressive drugs leads to a suppression of the entire immune system, which enhances the possibility for infections or development of malignant tumors. Also in some cases, the effectiveness of these drugs can be reduced or even abrogated. For example, steroid refractory GvHD is one of the major problems following allogeneic hematopoietic stem cell transplantation (Auletta et al., 2009; von Bonin et al., 2009). For treatment of GvHD, immunosuppressive strategies against key elements of T-cell reactions were already performed (von Bonin et al., 2009). However, because of the high numbers of patients, these strategies were mainly used in rheumatology (Kameda et al., 2009; Senolt et al., 2009) or for patients after kidney transplantation. For therapy of acute GvHD, most experiences are available for OKT3® (Benekli M et al., 2006; Knop et al., 2007) or interleukin 2 receptor antibodies (Chen et al., 2004; Ji et al., 2005), and for chronic GvHD with anti CD20 antibodies (Bates et al., 2009). However, these antibodies can be associated with less long-term success and toxicity because of appearance of infectious complications. The use of monoclonal antibodies for clinical application was restricted because of the missing humanization. Murine antibodies or antibodies from other species are huge molecules with a molecular weight in the range of 150 kDa that may be highly immunogenic in humans. After application of murine anti human monoclonal antibodies, life-threatening and anaphylactic complications were observed (Chester et al., 1995). Also, the immunogenic potential of the antibodies depends from their peptide structure. IgG4 isotypes, for example, are less immunogenic than IgG1 isotypes because of the low potential for complement activation. Besides, the humanization of antibodies leads to chimeric isotypes that are less immunogenic than their originally murine counterparts (Hosono et al., 1992). Up to date, there are no clear data that show that totally human antibodies have clinically advantages compared to chimeric antibodies.

Accordingly, the investigation of alternative or improved therapeutic approaches or procedures including the use of new cell sources, the treatment with antibodies or other biologicals are still in need.

One possible approach focuses on CD4 positive T helper cells. Said cells coordinate both the pathological and the physiological immune reaction in the human body. Influencing CD4 positive T helper cells by application of anti CD4 antibodies should, therefore, lead to a targeted modulation of the immune system.

Previously, the murine anti human CD4 monoclonal antibody Max16H5 (IgG1) was used in clinical application in patients with auto-immune diseases or as a protective therapy against transplant rejection (Chatenoud et al., 1995; Emmrich et al., 1991a; Emmrich et al., 1991b). Furthermore, in human kidney transplantation, Max16H5 (IgG1) had the potential to effectively reduce graft rejection (Reinke et al., 1991; Reinke et al., 1995). The application of anti CD4 specific monoclonal antibodies may not only result in suppression of immune activity but also in the induction of tolerance against tetanus toxoid in an triple transgeneic mouse model (Laub et al., 2002). The induction of tolerance by a rat monoclonal antibody has also been demonstrated (Kohlhaw et al., 2001). Said monoclonal antibody Max16H5 is also disclosed in EP 1 454 137, which is incorporated herein by reference and which, among others, relates to the use of a labeled ligand having specificity for the human CD4 molecule to produce an in vivo diagnostic agent.

CD4+ molecules on T helper cells bind directly to constant regions of HLA molecules on antigen presenting cells (APCs) to allow a complete T cell activation. To interfere with this binding by non depleting monoclonal antibodies may inhibit this activation by a total steric blockage, by shortening of cell-cell contact between APC and T cell (Fehervari et al., 2002) or by induction of negative signals by inhibition of protein tyrosine phosphorylation (Harding et al., 2002) or induction of T cell anergy (Madrenas et al., 1996). Here, Fehérvári at al. and Harding et al. do not disclose the methods and uses of the invention. Among others, they did not incubate stem cell grafts with anti CD4 antibodies, but isolated CD4+ cells separated out of spleens (murine) and buffy coats (human).

In addition, WO 2004/112835 describes, among others, methods involving the use of antibodies including antibodies directed against CD4. Here, anti CD4 antibodies were used to generate regulatory T cells over a long period in order to induce immunological tolerance.

In view of the above, there is still a need of promising alternative and improved, respectively, therapeutic approaches that may lack disadvantages of the prior art methodologies.

Furthermore, there are many instances whereby the efficacy of a therapeutic protein is limited by an unwanted immune reaction to the therapeutic protein. Several mouse monoclonal antibodies have shown promise as therapies in a number of human disease settings but in certain cases have failed due to the induction of significant degrees of a human anti-murine antibody (HAMA) response (Schroff et al. (1985)). For monoclonal antibodies, a number of techniques have been developed in attempt to reduce the HAMA response (see e.g. WOA9106667). These recombinant DNA approaches have generally reduced the mouse genetic information in the final antibody construct whilst increasing the human genetic information in the final construct. Notwithstanding, the resultant "humanized" antibodies have, in several cases, still elicited an immune response in patients (Isaacs J. D. (1990)).

Antibodies are not the only class of polypeptide molecule administered as a therapeutic agent against which an immune response may be mounted. Even proteins of human origin and with the same amino acid sequences as occur within humans can still induce an immune response in humans.

Key to the induction of an immune response is the presence of peptides within the protein that can stimulate the activity of T cells via presentation on MHC class II molecules, so-called "T-cell epitopes."

MHC Class II molecules are a group of highly polymorphic proteins which play a central role in helper T cell selection and activation. The human leukocyte antigen group DR (HLA-DR) are the predominant isotype of this group of proteins; however, isotypes HLA-DQ and HLA-DP perform similar functions. In the human population, individuals bear two to four DR alleles, two DQ and two DP alleles. The structure of a number of DR molecules have been solved and these appear as an open-ended peptide binding groove with a number of pockets that engage amino acid side chains (pocket residues) of the peptide (Stern et al. (1994)). Polymorphisms identifying the different allotypes of class II molecule contributes to a wide diversity of different binding surfaces for peptides within the peptide binding groove and, at the population level, ensures maximal flexibility with regard to the ability to recognize foreign proteins and mount an immune response to pathogenic organisms.

An immune response to a therapeutic protein proceeds via the MHC class II peptide presentation pathway. Here exogenous proteins are engulfed by antigen presenting cells (APCs) and processed for presentation at the cell surface in association with MHC class II molecules of the DR, DQ or DP type. MHC Class II molecules are expressed by professional antigen presenting cells, such as macrophages and dendritic cells amongst others. Engagement of a MHC class II peptide complex by a cognate T cell receptor on the surface of the T cell, together with the cross-binding of certain other co-receptors such as the CD4 molecule, can induce an activated state within the T cell. Activation leads to the release of cytokines further activating other lymphocytes such as B cells to produce antibodies or activating T killer cells as a full cellular immune response.

T cell epitope identification is the first step to epitope elimination as recognized in WO98/52976 and WO00/34317. In these teachings, predicted T cell epitopes are removed by the use of judicious amino acid substitutions within the protein of interest. Besides computational techniques, there are in vitro methods for measuring the ability of synthetic peptides to bind MHC class II molecules. An exemplary method uses B-cell lines of defined MHC allotype as a source of MHC class II binding surface and may be applied to MHC class II ligand identification (Marshall et al. (1994); O'Sullivan et al. (1990); Robadey et al. (1997)). However, such techniques are not adapted for the screening of multiple potential epitopes to a wide diversity of MHC allotypes, nor can they confirm the ability of a binding peptide to function as a T cell epitope.

Recently, techniques exploiting soluble complexes of recombinant MHC molecules in combination with synthetic peptides have come into use (Kern et al. (1998); Kwok et al (2001)). These reagents and procedures are used to identify the presence of T cell clones from peripheral blood samples from human or experimental animal subjects that are able to bind particular MHC-peptide complexes and are not adapted for the screening multiple potential epitopes to a wide diversity of MHC allotypes.

CD4 is a surface glycoprotein primarily expressed on cells of the T lymphocyte lineage including a majority of thymocytes and a subset of peripheral T cells. Low levels of CD4 are also expressed by some non-lymphoid cells although the functional significance of such divergent cellular distribution is unknown. On mature T cells, CD4 serves a co-recognition function through interaction with MHC Class II molecules expressed in antigen presenting cells. CD4+ T cells constitute primarily the helper subset which regulates T and B cell functions during T-dependent responses to viral, bacterial, fungal and parasitic infections.

During the pathogenesis of autoimmune diseases, in particular when tolerance to self antigens breaks down, CD4+ T cells contribute to inflammatory responses which result in joint and tissue destruction. These processes are facilitated by the recruitment of inflammatory cells of the hematopoietic lineage, production of antibodies, inflammatory cytokines and mediators, and by the activation of killer cells.

CD4 antibodies are known in the art. An exemplary CD4 antibody, monoclonal mouse anti human CD4-antibody 30F16H5, is disclosed in DE 3919294. Said antibody is obtainable from the hybridoma cell line ECACC 88050502.

To reduce the immunogenicity of mouse anti-CD4 antibodies, humanized anti-CD4 antibody have been previously engineered by cloning the hypervariable regions of a mouse antibody into frameworks provided by human immunoglobulins (e.g. Boon et al. (2002)). Although reducing the immunogenicity compared to mouse anti-CD4, these humanized antibody still elicited immune responses in several cases.

Furthermore, it is known from the art that such a "humanization" of antibodies often results in antibodies with lower or significantly lower affinity to the given target.

It is, hence, a further objective of the invention to provide for modified forms of an anti human CD4-antibody to reduce the immune reaction to mouse anti-CD4 antibodies. In particular, it is desirable to provide anti-CD4 antibodies with a reduced number of T cell epitopes which may result in a reduced or absent potential to induce an immune response in a human subject. Such proteins may be expected to display an increased circulation time within a human subject capable of mounting an immune response to the non-modified antibody and may be of particular benefit in chronic or recurring disease settings such as is the case for a number of indications for anti-CD4. While others have provided anti-CD4 antibody molecules including "humanized" forms, none of these teachings recognize the importance of T cell epitopes to the immunogenic properties of the protein nor have been conceived to directly influence said properties in a specific and controlled way according to the scheme of the present invention.

SUMMARY OF THE INVENTION

In one aspect, the present invention relates to an in vitro method of modifying a cell graft containing immune cells comprising the steps of a) incubating a cell graft containing immune cells with an anti CD4 antibody wherein said incubating is carried out for from 1 minute to 7 days, b) removing unbound antibody from said graft.

In another aspect, the present invention relates to a modified cell graft containing immune cells wherein said graft i) is obtainable in accordance with the in vitro method of the invention; and/or ii) comprises anti CD4 antibodies bound to from 40% to 100% of the accessible CD4 epitopes of said graft.

In another aspect, the present invention relates to the modified cell graft containing immune cells of the invention for use in medicine, particularly for use in a method of treating in a subject one or more diseases treatable by transplantation.

In another aspect, the present invention relates to the use of an anti CD4 antibody for the in vitro modification of a cell graft containing immune cells, the modification comprising incubating said graft with said antibody for from 1 minute to 7 days.

In other aspects, the invention relates to methods, uses and grafts as defined in the claims and hereinbelow. In other aspects, the invention relates to particular antibodies disclosed herein.

A so-called additional aspect of the invention is summarized as follows: One facet of this additional aspect of the present invention relates to an anti human CD4-antibody comprising a heavy chain immunoglobulin variable domain (VH) and a light chain immunoglobulin variable domain (VL), wherein at least one T cell epitope located outside the CDRs of said immunoglobulin variable domains is removed from said immunoglobulin variable domains, particularly to an anti human CD4-antibody as defined hereinbelow. In a preferred embodiment of the said additional aspect of the present invention, said antibody has the CDRs of the antibody produced by the hybridoma cell line ECACC 88050502, or said antibody has the CDRs of SEQ ID NO: 2 and SEQ ID NO: 12. In a particular embodiment, the heavy chain immunoglobulin variable domain comprises a sequence selected from the group consisting of SEQ ID NOs: 4, 6, 8, and 10; and the light chain immunoglobulin variable domain comprises a sequence selected from the group consisting of SEQ ID NO: 14, 16, 18, and 20. In another facet, the said additional aspect of the present invention relates to a pharmaceutical composition comprising said antibody and a pharmaceutically acceptable carrier. In another facet, the said additional aspect of the present invention also relates to the use of said antibody for the manufacture of a medicament for therapeutically treating a subject and methods of treatment using said antibody. In another facet, the said additional aspect of the present invention relates to a nucleic acid encoding a heavy chain and/or a light chain immunoglobulin variable domain of said antibody, and to a vector comprising said nucleic acid, particularly wherein the nucleic acid is operably linked to an expression control sequence. The said additional aspect of the present invention further relates to a host cell comprising said nucleic acid and/or at least one vector described above, as well as to a method of preparing an antibody of the said additional aspect of the present invention, comprising culturing the host cell described above under conditions permitting expression under the control of suitable expression control sequence(s), and purifying said antibody from the medium of the cell. The said additional aspect of the present invention also relates to an anti human CD4-antibody, wherein the antibody is obtained using the expression vectors pANTVhG4 and pANTVK. Generally, it is envisaged that the definitions, facets and embodiments described in context with the said additional aspect may also be applied to the invention in general. Preferably, in said additional aspect, the specificity and mode of action of the anti-CD4 antibodies are not affected by the modification(s)

SHORT DESCRIPTION OF THE FIGURES

FIG. 1 schematically illustrates the principle of antibody incubation of grafts as well as subsequent transplantation into a subject, such as a human being.

FIG. 2 contains an explanation of triple transgenic mice (TTG) as donors on a stable C57B1/6 background. TTG mice express human CD4 and HLA-DR while murine CD4 molecules are knocked out. That allows the determination of specific human surface molecules after transplantation (unique analysis of chimerism) and the direct testing of anti human CD4 antibodies in mice.

FIG. 3 shows an explanation of the experimental design. Bone marrow cells and splenocytes were taken from TTG mice, mixed and transplanted in lethally irradiated TTG mice with or without pre-treatment of anti human CD4 antibodies. These experiments were compared by using donor cells from C57B1/6 wild-type mice. Therapeutic effects (survival, organ repair, chimerism, GvHD) after transplantation were investigated.

FIG. 4 depicts the survival rate after transplantation of BM/splenocytes from TTG mice in Balb/c mice with or without pre-incubation of anti CD4 antibodies. In mice receiving pre-treated cells, the survival rate was significantly increased (0% to 83%, $p<0.001$). The observed effect was specific for transplantation from TTG in Balb/c mice, because by using wild-type C57B1/6 mice as donors, the effect could not be repeated. This result shows the specific binding of the antibody to human CD4 and thus wild-type donor cells are not affected.

FIG. 5 illustrates the hematopoietic recovery after transplantation of BM/splenocytes from TTG mice in Balb/c mice with (A+C) or without (A+B) pre-incubation of anti CD4 antibodies. In mice receiving pre-treated cells, the hematopoietic system recovered to the initial values after transplantation. Compared to recipients transplanted without pre-incubated cells, the reconstitution of monocytes and granulocytes was before lymphocyte reconstitution (C).

FIG. 6 depicts the GvHD score (that includes body weight according to Cooke et al., 1996) after transplantation of BM/splenocytes from TTG mice in Balb/c mice with or without pre-incubation of anti CD4 antibodies. In mice receiving pre-treated cells, the GvHD score in antibody receiving mice was lower than in animals receiving bone marrow and splenocytes without pre-treatment of anti CD4 antibodies indicating no GvHD development. Engraftment was also confirmed by immunohistological analyses. In bone marrow cavities there was a prevalent form of hematopoiesis in transplanted animals and a stable engraftment of human CD4 expressing T cells.

FIG. 7 relates to experiments involving the engraftment of human CD4, murine CD4, and murine CD8 after transplantation of BM/splenocytes from TTG mice in Balb/c mice without pre-incubation of anti human CD4 antibodies. Twelve days after transplantation, human CD4, murine CD4, and murine CD8 cells could be stably detected and mice develop a severe GvHD.

FIG. 8 relates to experiments involving the engraftment of human HLA-DR3 and murine MHC class I of TTG/C57B1/6 of (H-2 Kb) after transplantation of BM/splenocytes from TTG mice in Balb/c mice without pre-incubation of anti human CD4 antibodies. Twelve days after transplantation, human HLA-DR3 and MHC class I of TTG/C57B1/6 of H-2 Kb and mice develop a severe GvHD.

FIG. 9 relates to experiments involving the engraftment of human CD4, murine CD8 and decrease of murine CD4 of TTG/C57Bl/6 of (H-2 Kb) after transplantation of BM/splenocytes from TTG mice in Balb/c mice with pre-incubation of anti human CD4 antibodies. After transplantation a stable engraftment could be observed without development of GvHD.

FIG. 11 depicts exemplified vectors for expression of modified light and heavy chains in mammalian cells. dhfr is dihydrofolate reductase gene used for gene amplification by exposure of cells to increasing concentrations of methotrexate; CMV P is the CMV IE promoter.

FIG. 12 depicts the DNA and amino acid sequences of exemplary modified heavy chain variable regions.

FIG. 13 depicts the DNA and amino acid sequences of exemplary modified light chain variable regions.

DETAILED DESCRIPTION OF THE PREFERRED EMBODIMENTS

Figure 1:
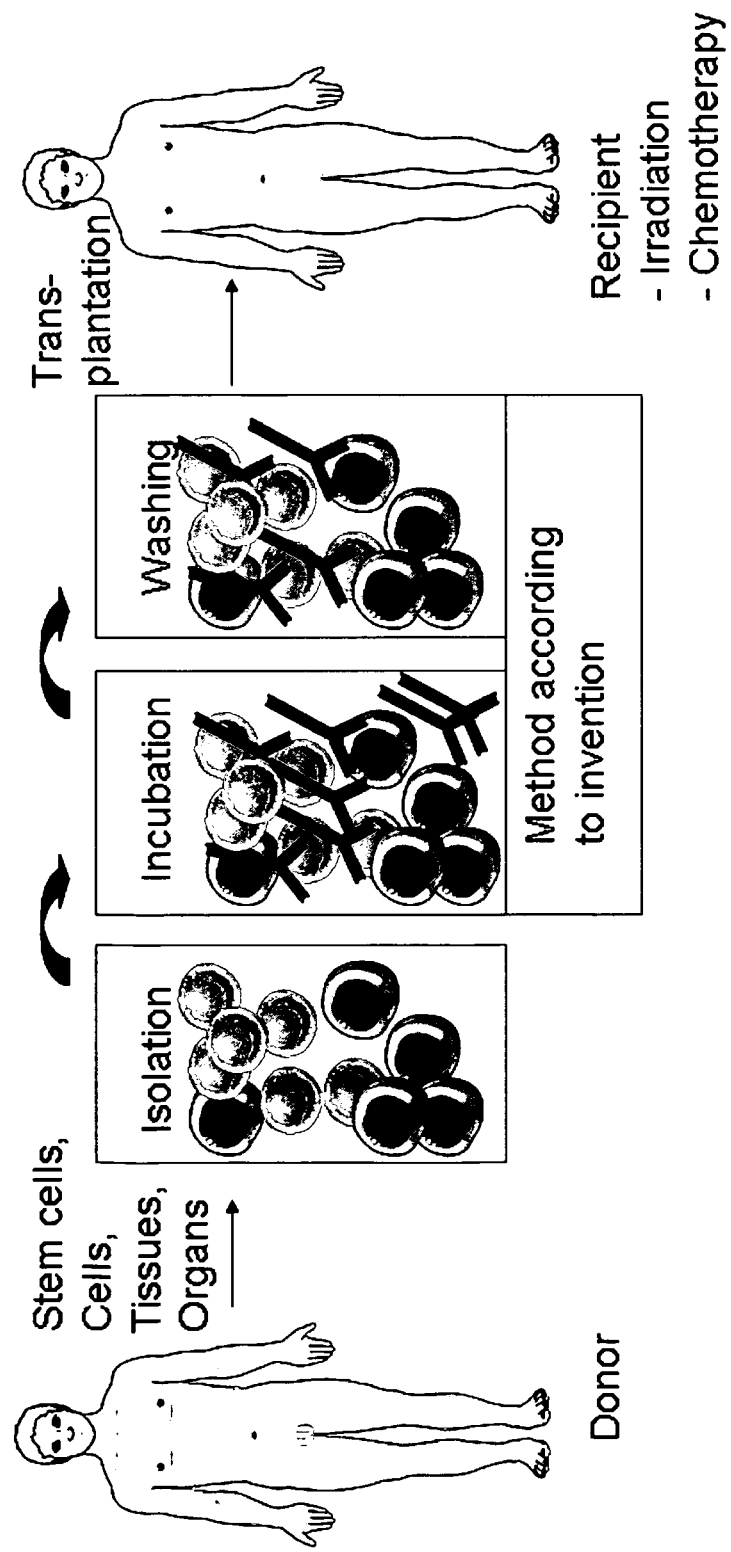
Figure 2:
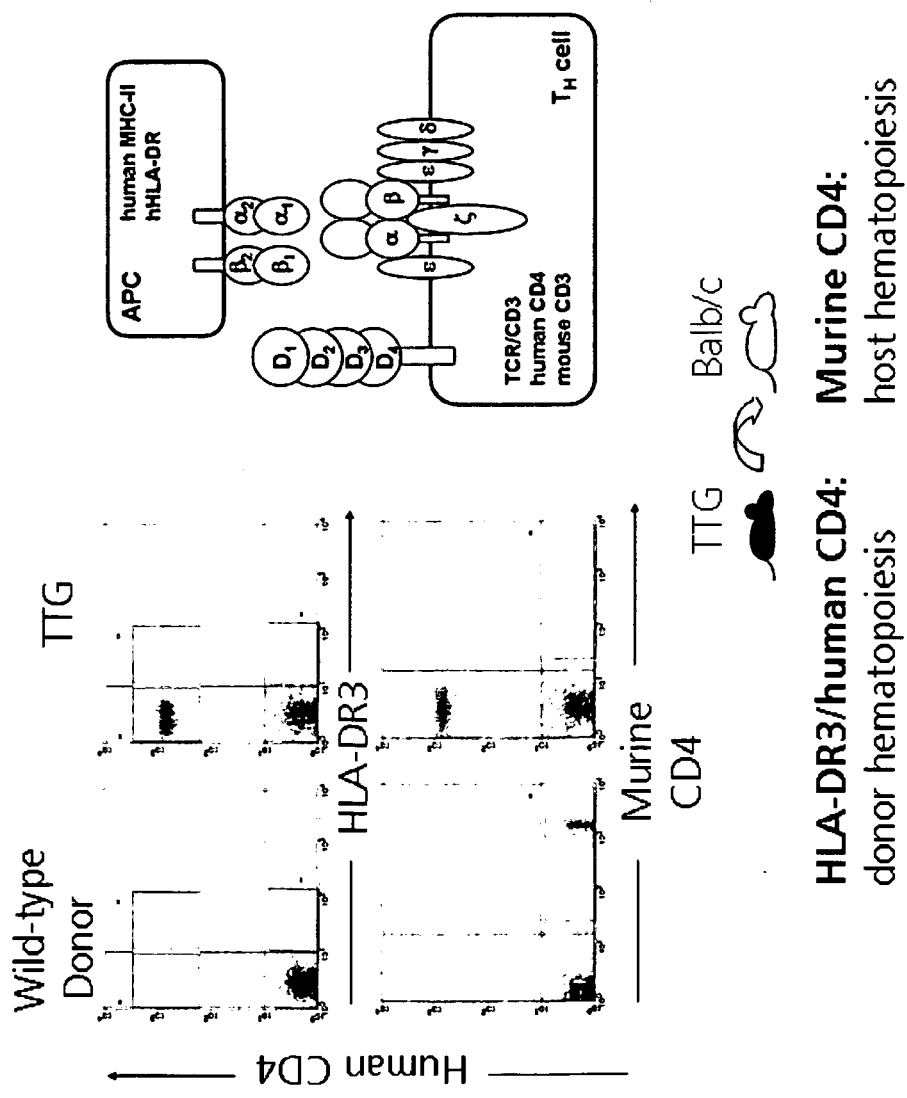
Figure 3:
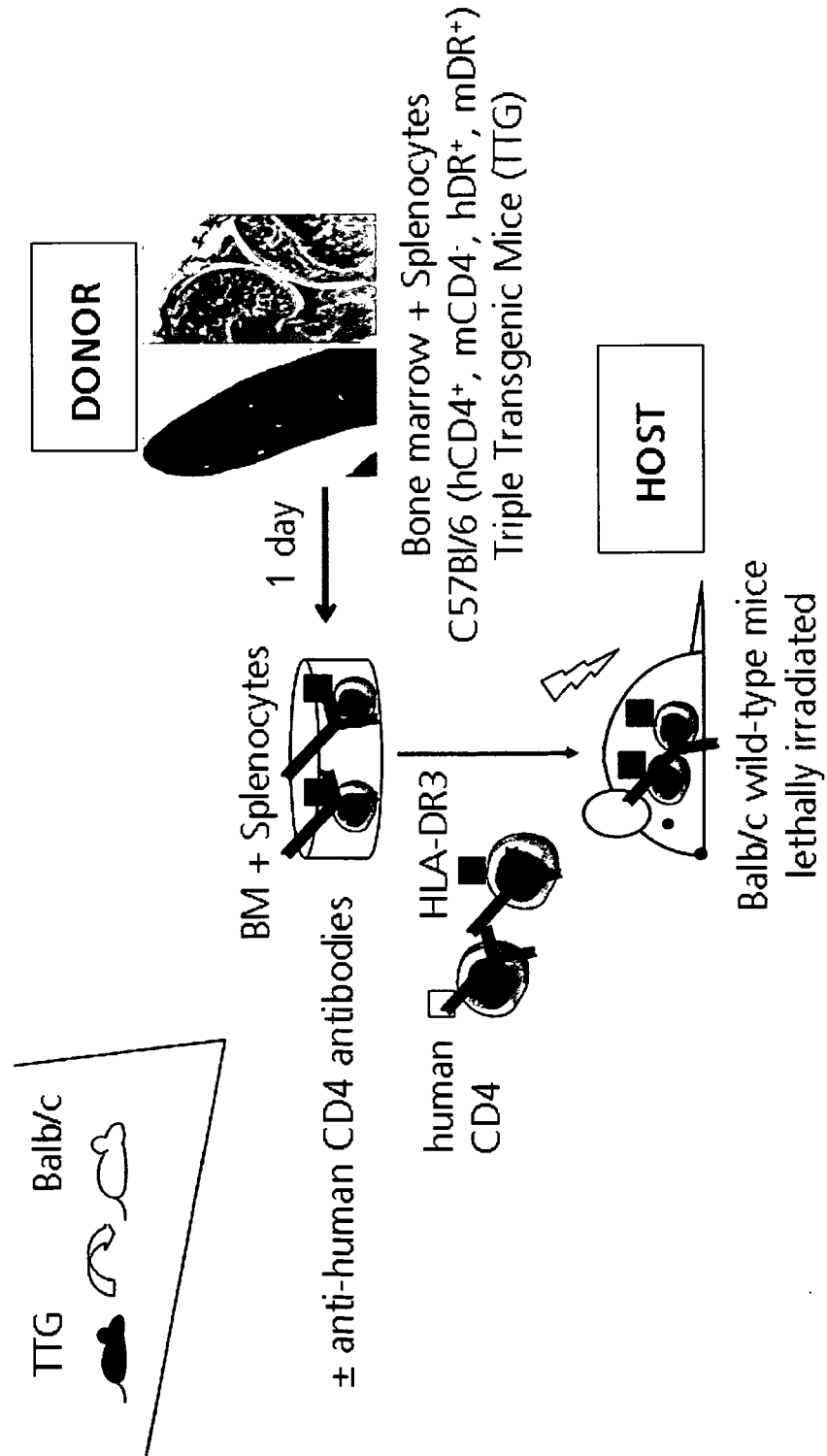
Figure 4:
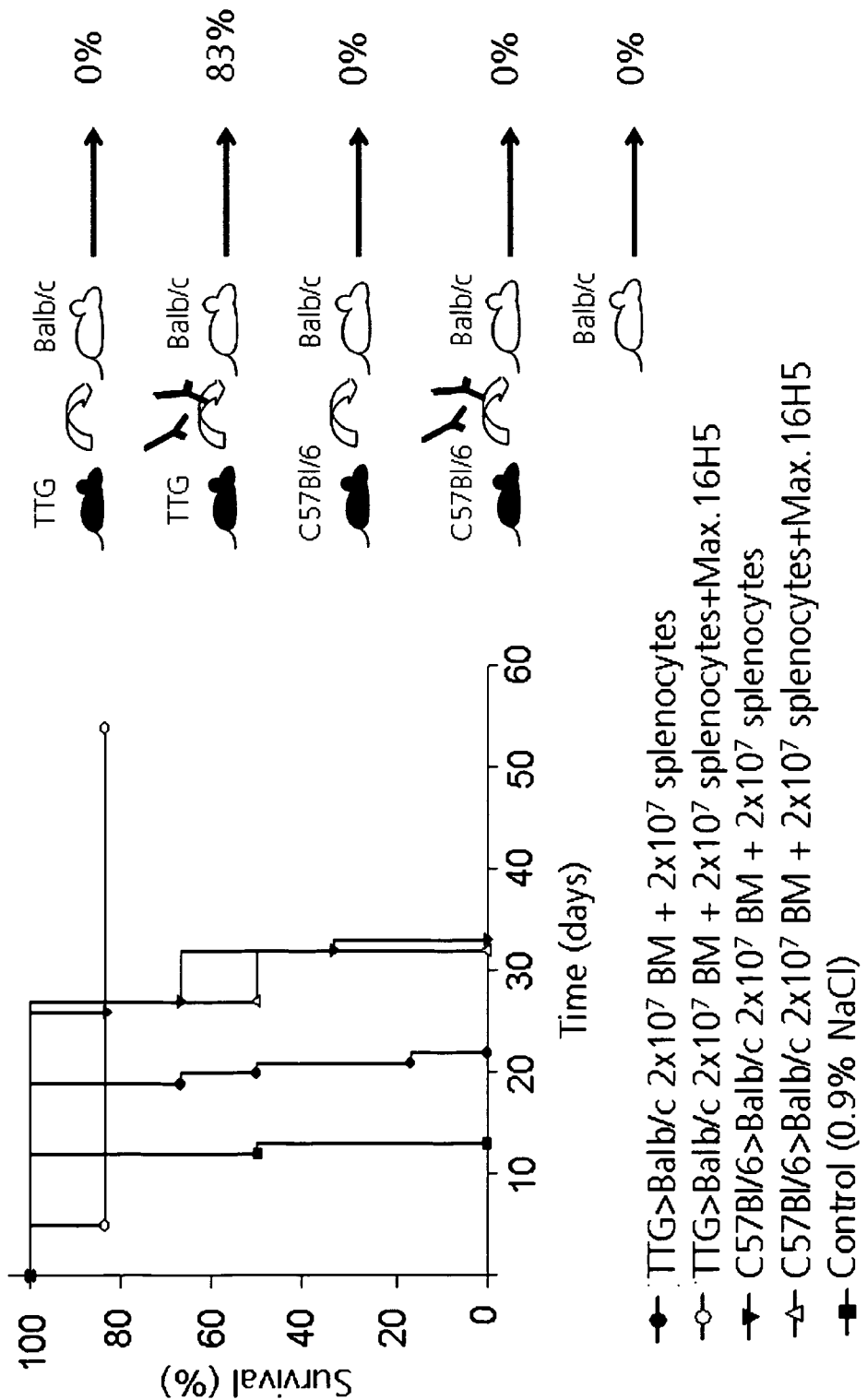
Figure 5:
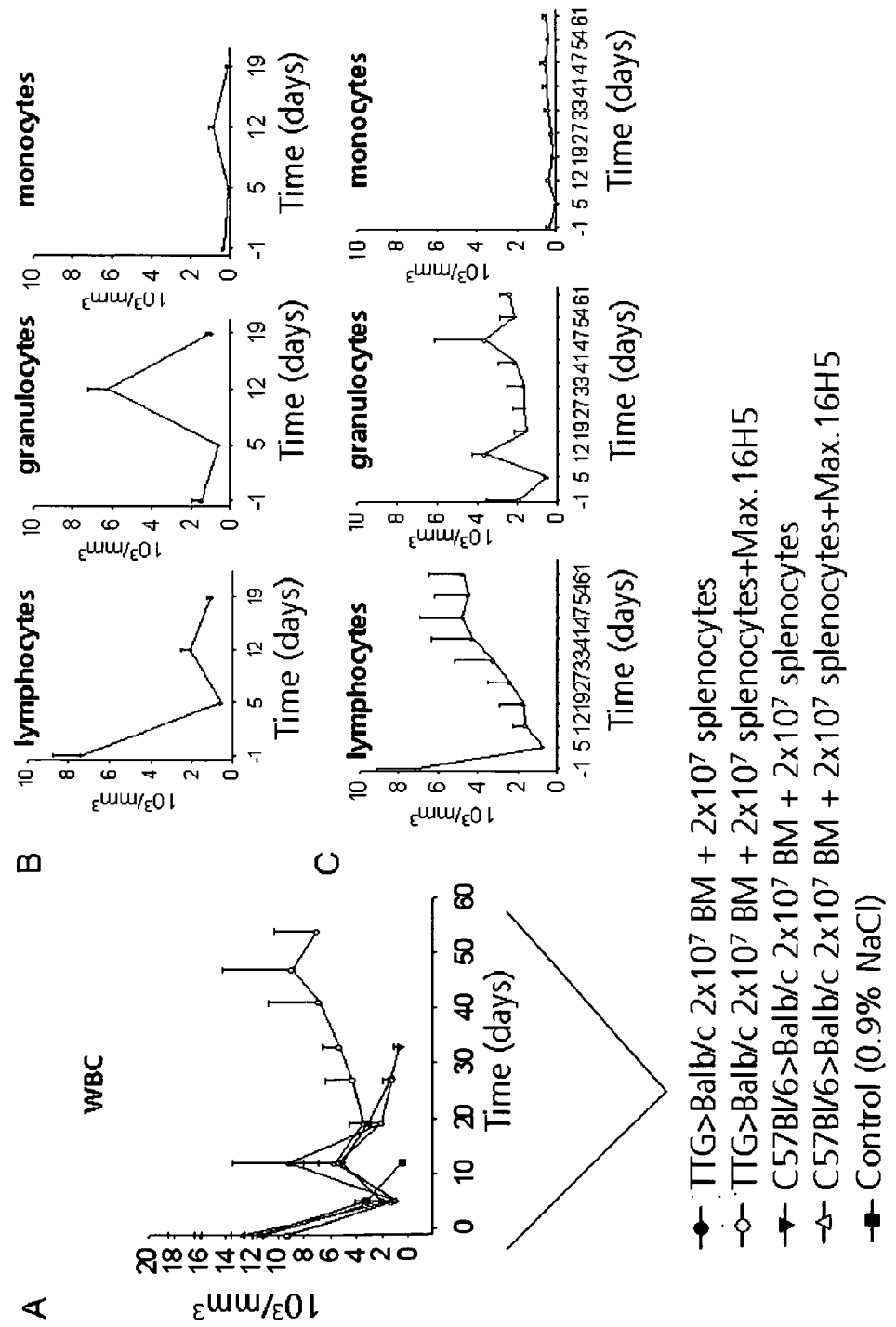
Figure 6:
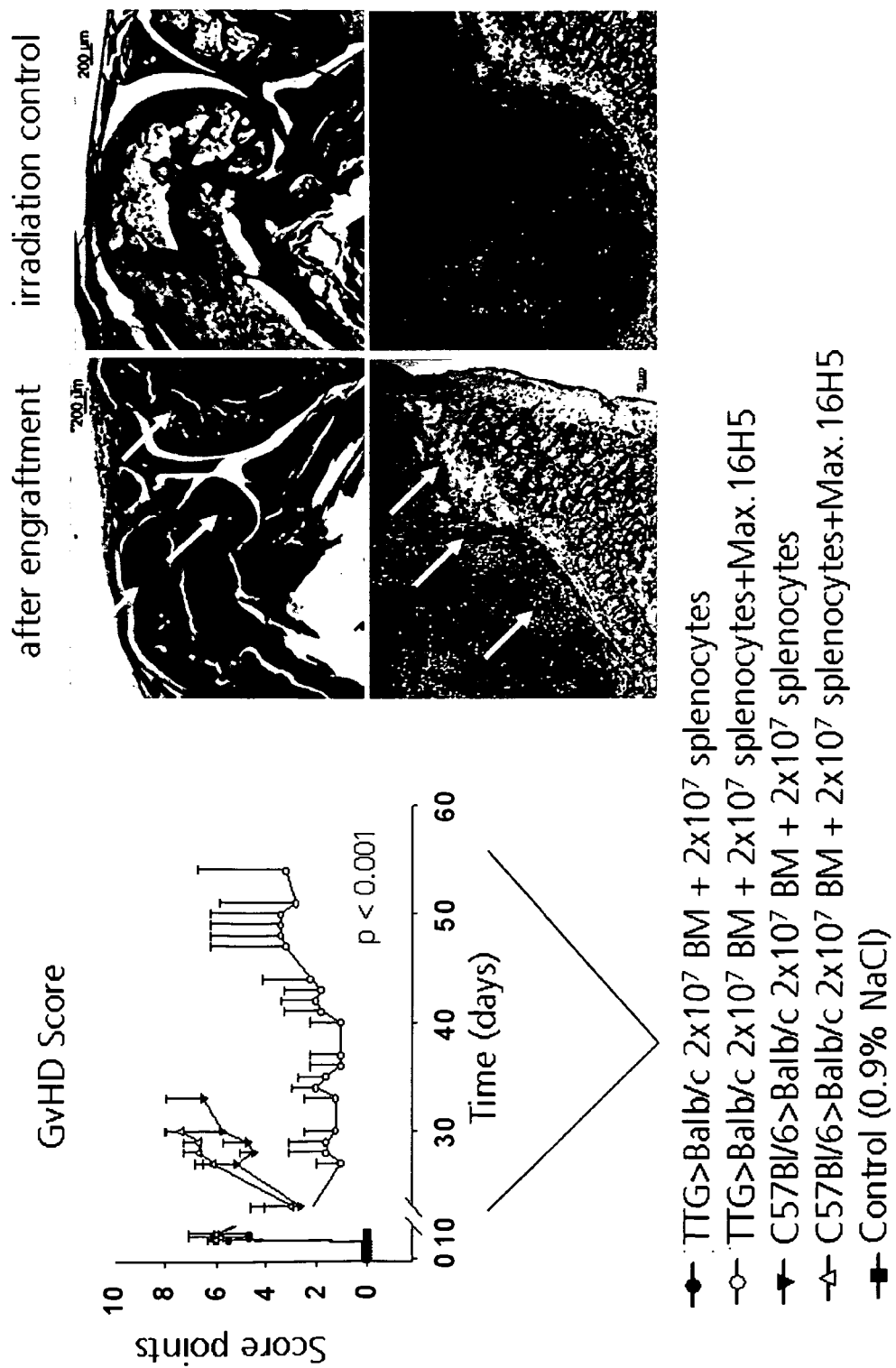
Figure 7:
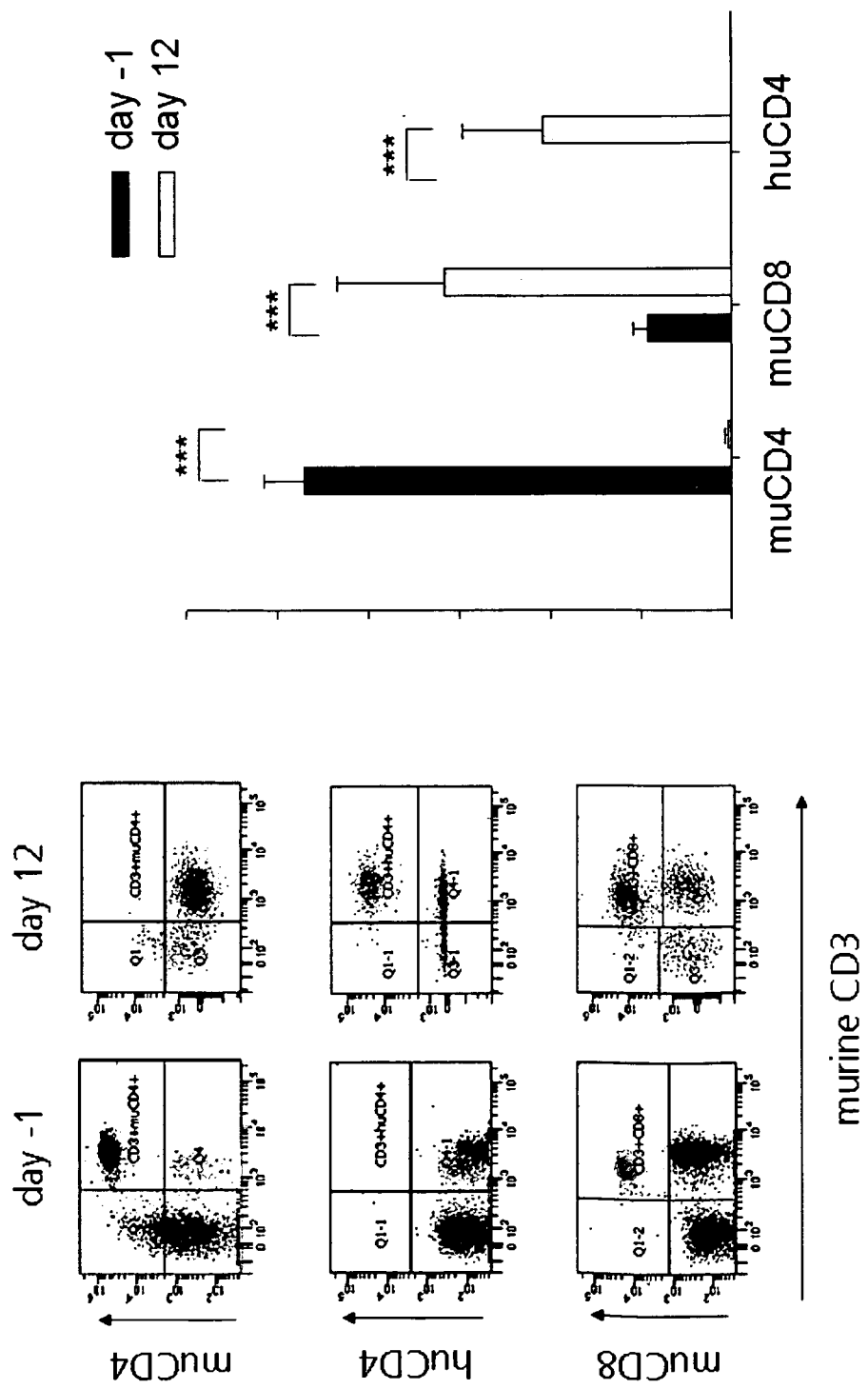
Figure 8:
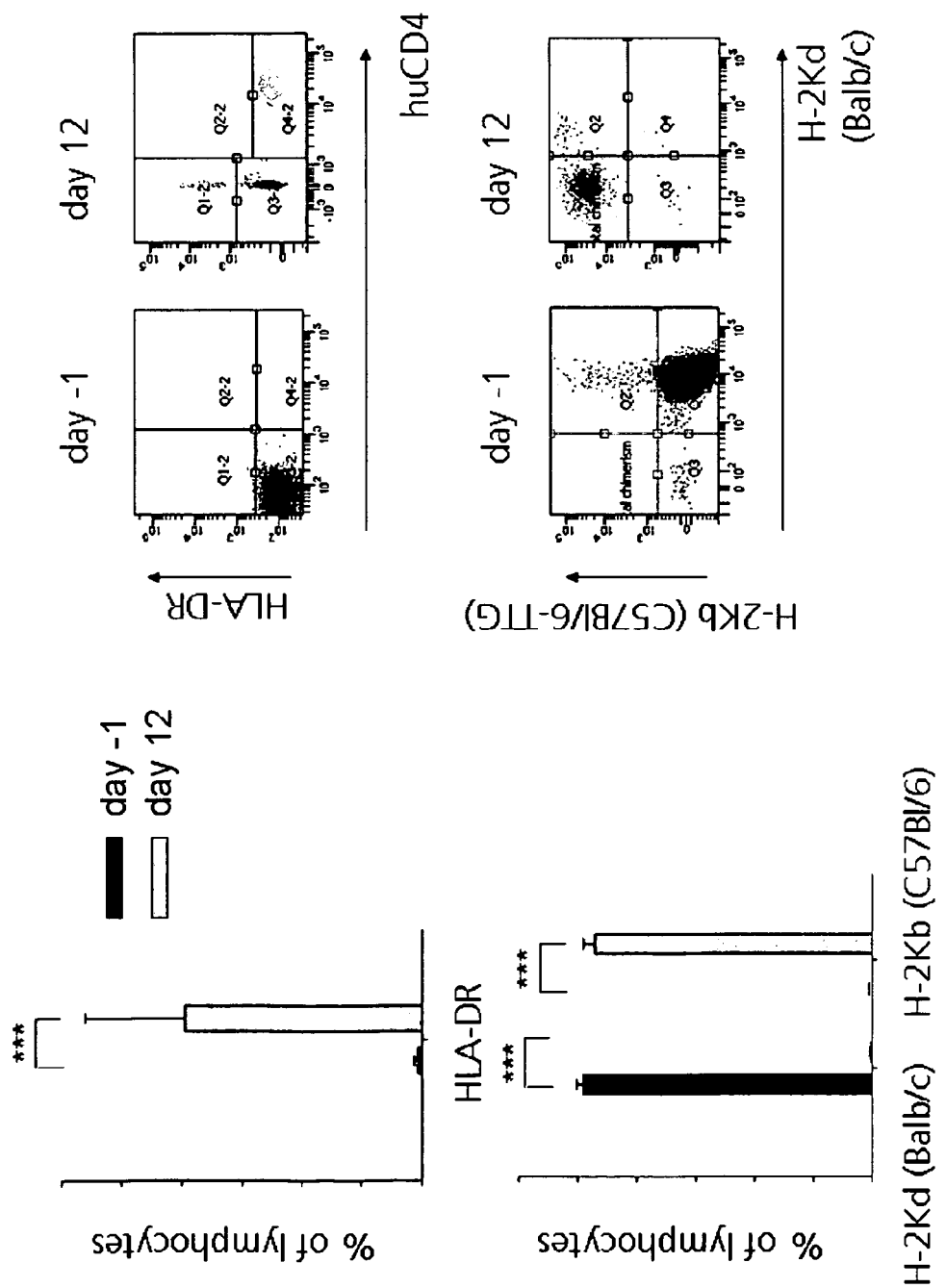
Figure 9:
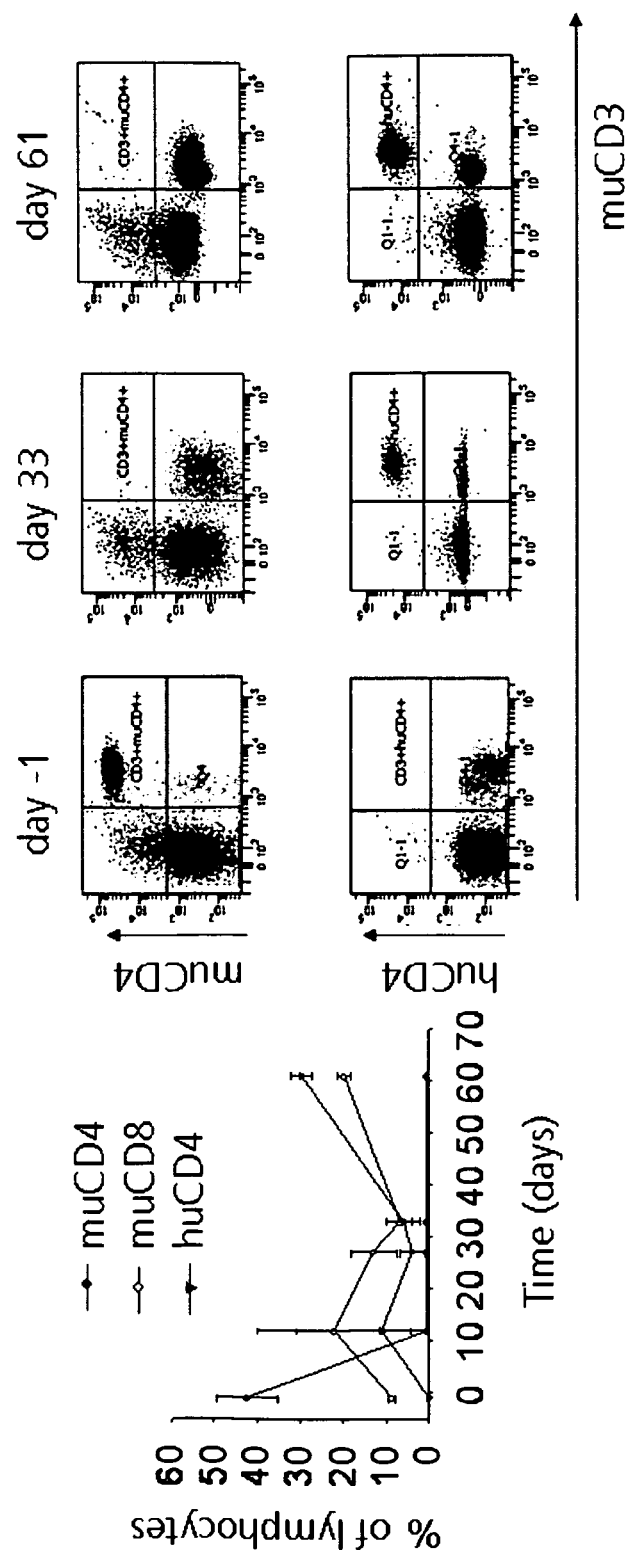
Figure 10:
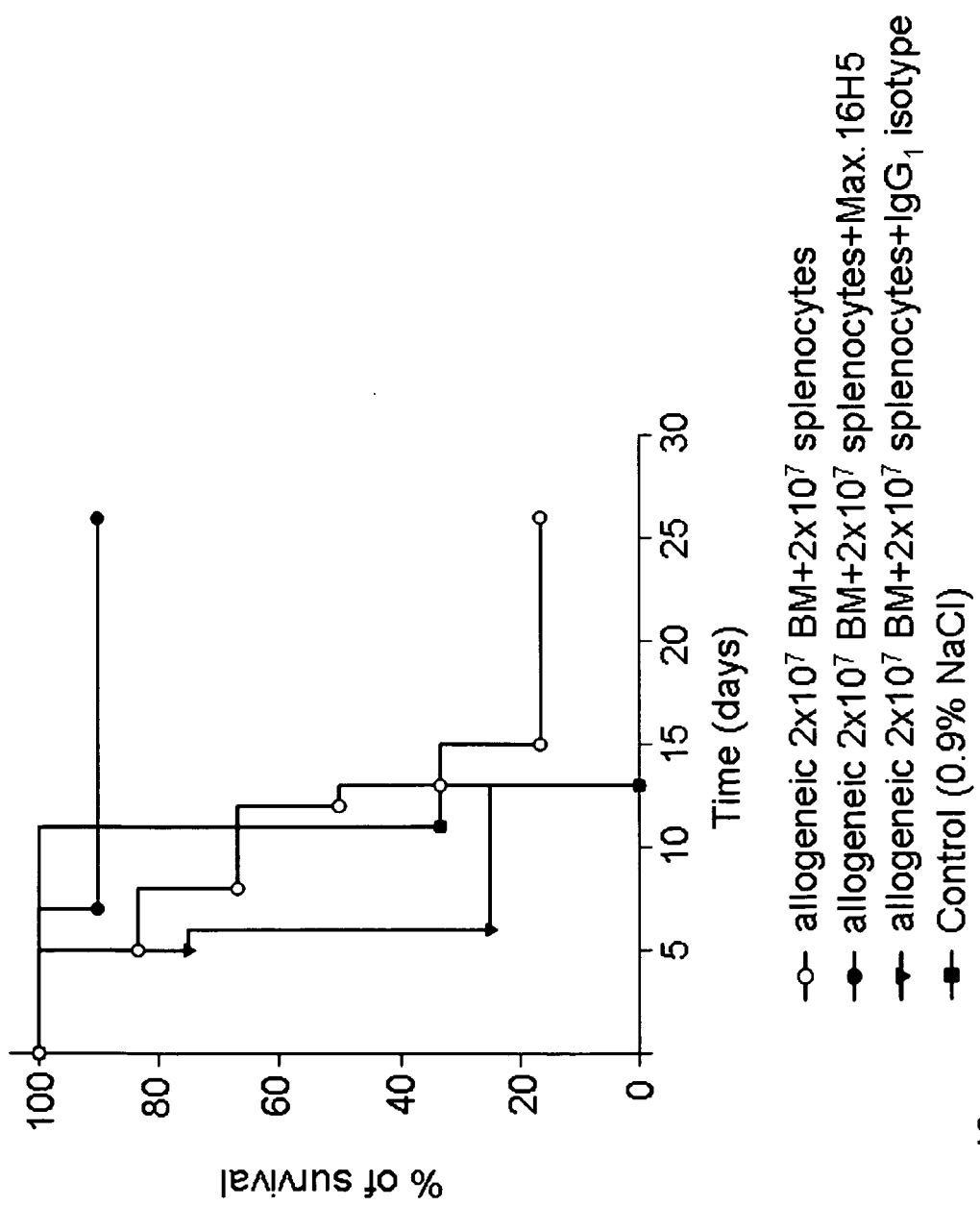
FIG. 10 depicts the survival rate after transplantation of BM/splenocytes from TTG mice in Balb/c mice with or without pre-incubation of anti CD4 antibodies. Using an IgG1-isotype control antibody, the preventive GvHD effect could not be observed.

The present invention e.g. relates to the in vitro treatment of cell grafts containing immune cells with antibodies, which avoids their direct application in vivo. That is, the present inventors could, for example, show that the (preferably short term) incubation of bone marrow grafts with an anti human CD4 antibody before transplantation of these cell grafts containing immune cells prevents the development of GvHD after transplantation as compared to isotype or untreated controls.

As opposed to work of the prior art, the presented work e.g. deals with the short term incubation of a (stem cell) graft such as cell suspensions containing T cells, in particular CD4 cells, with the aim of tolerance induction or immunosuppression to prevent e.g. Graft-versus-Host-Disease (GvHD).

Without intending to be bound by theory, the present inventors consider the anti CD4 antibody incubation of (stem cell) grafts comprising CD4 positive (immune) cells and subsequent removing of unbound antibodies to result in a modified graft, wherein the antibody labeled cells are selectively inactivated by the antibody or are prepared for becoming inactivated or becoming regulatory cells as soon as they encounter specific antigen, such that e.g. GvHD is not initiated. It is assumed that the anti CD4 antibody binds to immune cells (such as lymphocytes) bearing CD4 and thereby exerts its beneficial effect. In addition, it is considered feasible that the preferred anti CD4 antibodies described herein show particularly advantageous features due to their binding of (a) specific epitope(s) in order to e.g. prepare the cell for subsequent inactivation.

As will be readily apparent to the skilled person, substantially reducing or avoiding the administration of free anti CD4 antibodies, i.e. anti CD4 antibodies that are not bound to an to antigen located on the graft, is advantageous. Generally, the present invention is considered to be related to one or more of the following advantages: i) no direct applications of the antibodies to the recipients are required; ii) a short term incubation of the graft, such as cell suspensions, tissues, and organs containing T cells, in particular CD4 cells; iii) GvHD prevention after transplantation of the graft of the invention; iv) prevention of other immunological complications after transplantation of the graft of the invention (e.g. cytokine-release syndrome); v) reduction of costs due to the avoidance or reduction of conventional immunosuppressive drugs and a significantly reduced amount of antibodies as compared to systemic application; vi) improvement of survival of patients receiving a transplantation of the graft of the invention; vii) facilitation of transplantation of grafts also for patients such as older patients, which can not be transplanted with regular grafts due to expected immunological complications; and viii) use of HLA mismatch donors for transplantation or less good HLA matches than without the invention.

In a first aspect, the present invention relates to an in vitro method of modifying a cell graft containing immune cells comprising the steps of a) incubating a cell graft containing immune cells with an anti CD4 antibody, especially wherein said incubating is carried out for from 1 minute to 7 days, b) removing unbound antibody from said graft.

Antibodies and also anti CD4 antibodies are generally well known in the art. As used herein, by "antibody" is meant inter alia a protein of the immunoglobulin family that is capable of specifically combining, interacting or otherwise associating with an antigen, wherein said combining, interacting or otherwise associating (such as binding) of the antibody to the antigen is mediated by complementarity-determining regions (CDRs). Similarly, term "antigen" is used herein to refer to a substance that is capable of specifically combining, interacting or otherwise associating with said antibody. In the context of the anti CD4 antibody of the present invention the antigen is meant to be CD4, particularly human CD4.

As used herein, the term "CDR" refers to the "complementarity-determining region" of an antibody, i.e. to one of the hypervariable regions within an immunoglobulin variable domain contributing to the determination of antibody specificity. CDRs are well known to a person skilled in the art. Typically, both the heavy chain immunoglobulin variable domain and the light chain immunoglobulin variable domain contain three CDRs.

In the context of the present invention, the term "antibody" is considered to also relate to antibody fragments including for example Fv, Fab, Fab' and F(ab')2 fragments. Such fragments may be prepared by standard methods (for example; Coligan et al., 1991-1997, incorporated herein by reference). The present invention also contemplates the various recombinant forms of antibody derived molecular species well known in the art. Such species include stabilized Fv fragments including single chain Fv forms (e.g., scFv) comprising a peptide linker joining the VH and VL domains, or an Fv stabilized by interchain disulphide linkage (dsFv) and which contain additional cysteine residues engineered to facilitate the conjoining of the VH and VL domains. Equally, other compositions are familiar in the art and could include species referred to as "minibodies"; and single variable domain "dAbs". Other species still may incorporate means for increasing the valency of the modified antibody V-region domain, i.e. species having multiple antigen binding sites for example by the engineering of dimerisation domains (e.g., "leucine zippers") or also chemical modification strategies. Moreover, the term "antibody" also relates to multimers of scFv such as diabodies, triabodies or tetrabodies, tandabs, flexibodies, bispecific antibodies, and chimeric antibodies, all known in the art. As used herein, antibodies are considered to also include any bivalent or multivalent antibodies. They also include any antibody derivatives and any other derivatives known to the skilled person.

In some embodiments, the antibody is a polyclonal antibody. In preferred embodiments, the antibody is a monoclonal antibody.

According to the invention, the term "anti CD4 antibody" refers to an antibody, which has the ability to bind to CD4. Preferably, the anti CD4 antibody is an anti human CD4 antibody. "CD4" or "cluster of differentiation 4" refers to a protein, more precisely a surface glycoprotein, well known to the person skilled in the art (cf Bowers et al., 1997). In the present context CD4 may also refer to a fragment of full-length CD4, or an otherwise modified form of CD4, provided that the fragment or otherwise modified form still functions as an antigen in the context of the antibody of the present invention.

Preferred anti CD4 antibodies are selected from the group consisting of Max16H5, OKT4A, OKTcdr4a, cMT-412, YHB.46. Most preferably, said antibody is Max16H5. Cells for the production of Max16H5 have been deposited with the ECACC (European Collection of Cell Cultures) with accession number ECACC 88050502. Said antibody is also disclosed in DE 3919294, which is incorporated by reference herein. As used herein, the antibody "Max16H5" may also be referred to as "Max.16H5", "MAX16H5" or "MAX.16H5", or also "30F16H5" (wherein the latter name is also the name of deposited cells producing said antibody). Max.16H5 may also be obtained from the cell line MAX.16H5/30F16H5.

A further preferred anti CD4 antibody for use in the invention is 16H5.chimIgG4. As used herein, said antibody may also be referred to as "16H5.chim" or as "CD4.16H5.chimIgG4" (wherein the latter name is also the name of deposited cells producing said antibody). 16H5.chimIgG4 may be obtained from the cell line CD4.16H5.chimIgG4.

In detail, certain preferred anti CD4 antibodies in the context with the present invention are e.g. obtainable from any of the following deposits of biological material:
 deposit with the European Collection of Cell Cultures having the accession number ECACC 88050502;
 deposit "MAX.16H5/30F16H5", deposited with the DSMZ on Dec. 2, 2011;
 deposit "CD4.16H5.chimIgG4", deposited with the DSMZ on Dec. 2, 2011.

All of these deposits involve cells or cell lines, respectively, from which particular anti CD4 antibodies in the context with the present invention may be obtained. Deposit ECACC 88050502 is e.g. also described in application DE 3919294.

In some embodiments of the method, modified graft, or modified graft for use of the invention, said anti CD4 antibody i) is selected from the group consisting of Max16H5, OKT4A, OKTcdr4a, cMT-412, YHB.46, particularly wherein said anti CD4 antibody is Max16H5; and/or ii) is antibody 30F16H5; and/or iii) is obtainable from a cell line deposited with accession number ECACC 88050502; and/or iv) is obtainable from a cell line MAX.16H5/30F16H5 deposited with the DSMZ on Dec. 2, 2011; and/or v) is antibody 16H5.chimIgG4; and/or vi) is obtainable from a cell line CD4.16H5.chimIgG4 deposited with the DSMZ on Dec. 2, 2011; and/or vii) is an antibody comprising the VH and the VK of antibody 16H5.chimIgG4; and/or viii) is an antibody comprising a VH and a VK of an antibody obtainable from a cell line CD4.16H5.chimIgG4 deposited with the DSMZ on Dec. 2, 2011; and/or ix) is an antibody comprising any combination of a VH disclosed in FIG. 12 and of a VK disclosed in FIG. 13, particularly wherein said combination is selected from VH1/VK1, VH2/VK2, VH4/VK2 and VH4/VK4, especially wherein said combination is VH2/VK2.

In particular embodiments, the anti CD4 antibody used in the invention is "MAX.16H5". In particular embodiments, the anti CD4 antibody used in the invention is an antibody obtainable from cells of ECACC 88050502. In particular embodiments, the anti CD4 antibody used in the invention is an antibody obtainable from a deposit of biological material made by the Applicants with the DSMZ on Dec. 2, 2011. In particular embodiments, the anti CD4 antibody used in the invention is an antibody obtainable from cells deposited by the Applicants with the DSMZ on Dec. 2, 2011. In particular embodiments, the anti CD4 antibody used in the invention is an antibody obtainable from a deposit with the European Collection of Cell Cultures having the accession number ECACC 88050502. In particular embodiments, the anti CD4 antibody used in the invention is an antibody obtainable from cells "MAX.16H5/30F16H5" deposited with the DSMZ on Dec. 2, 2011. In particular embodiments, the anti CD4 antibody used in the invention is an antibody obtainable from cells "CD4.16H5.chimIgG4" deposited with the DSMZ on Dec. 2, 2011. In some embodiments, the anti CD4 antibody used in the invention comprises VH1 of FIG. 12. In some embodiments, the anti CD4 antibody used in the invention comprises VH2 of FIG. 12. In some embodiments, the anti CD4 antibody used in the invention comprises VH4 of FIG. 12. In some embodiments, the anti CD4 antibody used in the invention comprises VK1 of FIG. 13. In some embodiments, the anti CD4 antibody used in the invention comprises VK2 of FIG. 13. In some embodiments, the anti CD4 antibody used in the invention comprises VK4 of FIG. 13. In some embodiments, the anti CD4 antibody used in the invention comprises SEQ ID NO: 10. In some embodiments, the anti CD4 antibody used in the invention comprises SEQ ID NO: 8. In some embodiments, the anti CD4 antibody used in the invention comprises SEQ ID NO: 4. In some embodiments, the anti CD4 antibody used in the invention comprises SEQ ID NO: 20. In some embodiments, the anti CD4 antibody used in the invention comprises SEQ ID NO: 18. In some embodiments, the anti CD4 antibody used in the invention comprises SEQ ID NO: 14. In some embodiments, the anti CD4 antibody used in the invention comprises VH1 of FIG. 12 and/or VK1 of FIG. 13. In some particularly preferred embodiments, the anti CD4 antibody used in the invention comprises VH2 of FIG. 12 and/or VK2 of FIG. 13. In some embodiments, the anti CD4 antibody used in the invention comprises VH4 of FIG. 12 and/or VK2 of FIG. 13. In some embodiments, the anti CD4 antibody used in the invention comprises VH4 of FIG. 12 and/or VK4 of FIG. 13. In some embodiments, the anti CD4 antibody used in the invention comprises SEQ ID NO: 10 and/or SEQ ID NO: 20. In some particularly preferred embodiments, the anti CD4 antibody used in the invention comprises SEQ ID NO: 8 and/or SEQ ID NO: 18. In some embodiments, the anti CD4 antibody used in the invention comprises SEQ ID NO: 4 and/or SEQ ID NO: 18. In some embodiments, the anti CD4 antibody used in the invention comprises SEQ ID NO: 4 and/or SEQ ID NO: 14.

In some embodiments, the anti CD4 antibody used in the invention comprises the VH and the VK of the antibody 16H5.chimIgG4. In some embodiments, the anti CD4 antibody used in the invention comprises the CDRs of SEQ ID NO: 2 and SEQ ID NO: 12. In other preferred embodiments, the anti CD4 antibody for use in the invention is an anti CD4 antibody of or in accordance with the said additional aspect of the invention disclosed in detail hereinbelow. Preferably, said anti CD4 antibody is as described in the embodiments thereof, where preferred embodiments are particularly preferred. In general, the anti CD4 antibody used in the invention may be any anti CD4 antibody disclosed herein.

In certain preferred embodiments, the anti CD4 antibody is selected from antibodies recognizing the first and/or the second domain of the CD4 molecules. In certain preferred embodiments, the anti CD4 antibody is selected from antibodies recognizing the same domain/s of the CD4 molecules as Max16H5.

As used herein, "unbound antibody" refers to an antibody which, following the step of incubating, is not bound to the graft. In other words, it refers to an antibody which is not essentially associated with its ligands on the graft.

As used herein, an "in vitro method" refers to a method that is performed outside a living subject. It particularly also includes an "ex vivo method", such as in case of the graft comprising or being a tissue or an organ, but particularly excludes an "in vivo method" performed inside a living subject.

Preferably, according to the invention, the (step of) incubating is carried out for a time sufficient to allow binding of said antibody to said graft. Preferably, said incubating is carried out for a time sufficient to allow the binding of anti CD4 antibodies to from 40% to 100%, particularly 50% to 100%, particularly 60% to 100%, particularly 70% to 100%, more particularly 80% to 100%, more particularly 90% to 100%, more particularly 95% to 100%, more particularly 99% to 100%, of the accessible CD4 epitopes of said graft. Most preferably, following said incubating, anti CD4 antibodies bind to essentially all of the accessible CD4 epitopes of said graft.

An appropriate incubation period will easily be determined by the person skilled in the art. Usually, an appropriate incubation period will depend on the type of graft used. A preferred incubation period may also dependent on the amount of antibody used. Generally, where the graft e.g. is a cell suspension, shorter incubation periods will be required than where the graft e.g. is an organ.

Generally, where the graft comprises or is a tissue or an organ, longer incubation periods are preferred to allow the antibody to be transported—e.g. via diffusion—into the respective compartments.

Moreover, in any case, the skilled person may easily test the (status of the) binding of the anti CD4 antibodies according to methods well known within the art that may, for example, involve flow cytometry.

Generally, short incubation periods are preferred over long incubation periods in order to minimize any possible damage to the graft due to in vitro processing.

According to the invention said incubating may e.g. be carried out for from 1 minute to 7 days. In some embodiments, said incubating is carried out for from 1 to 150 minutes, particularly for from 10 minutes to 150 minutes, more particularly for from 30 minutes to 150 minutes, more particularly for from 40 minutes to 120 minutes, more particularly for from 45 minutes to 90 minutes, especially for from 50 minutes to 70 minutes. In other embodiments, said incubating is carried out for from 150 minutes to 7 days, particularly for from 150 minutes to 5 days, more particularly from 150 minutes to 3 days, more particularly from 150 minutes to 1 day, especially for from 150 minutes to 8 hours.

As to the removing of unbound (anti CD4) antibody in accordance with the methods and uses of the invention, various ways of performing said step are known to the skilled person. One exemplary way of removing unbound antibody from the graft is by washing the graft. Washing may e.g. occur by employing centrifugation where the graft comprises or is a cell suspension.

In the step of removing, preferably at least 40%, more particularly at least 50%, more particularly at least 60%, more particularly at least 70%, more particularly at least 80%, more particularly at least 90%, of unbound (anti CD4) antibody are removed from the graft. Preferably, up to 100% of unbound (anti CD4) antibody are removed from the graft.

The amount of antibody employed in the above step of incubating is not particularly limited. Appropriate amounts may easily be determined by the person skilled in the art and may e.g. depend on the type of graft used. Preferably according to the invention, said incubating is carried out with an antibody amount of from 0.1 µg to 100 mg.

In some embodiments, particularly where the graft is a cell suspension, said incubating is carried out with an antibody concentration of from 0.1 µg/ml cell suspension to 150 µg/ml cell suspension, particularly from 7 µg/ml cell suspension to 100 µg/ml cell suspension, more particularly from 30 µg/ml cell suspension to 100 µg/ml cell suspension, especially from 40 µg to 60 µg/ml cell suspension.

In some embodiments, particularly where the graft is a tissue or where the graft is an organ, said incubating is carried out with an antibody amount of from 0.1 mg to 10 mg, particularly from 1 mg to 10 mg, more particularly from 2 mg to 9 mg, more particularly from 3 mg to 8 mg, especially from 4 mg to 6 mg.

In some embodiments, particularly where the graft is a tissue or where the graft is an organ, said incubating is carried out with an antibody concentration in the incubation solution of from 0.1 mg/ml to 10 mg/ml, particularly from 1 mg/ml to 10 mg/ml, more particularly from 2 mg/ml to 9 mg/ml, more particularly from 3 mg/ml to 8 mg/ml, especially from 4 mg/ml to 6 mg/ml. Preferably, the specified volume includes the volume of said tissue or organ as well as the volume of the (antibody-containing) solution, in which said tissue or organ is incubated.

In some embodiments, particularly where the graft is a tissue or where the graft is an organ, said incubating is carried out by incubating said tissue or organ in a solution having an antibody concentration of from 10 µg/ml to 150 µg/ml, particularly from 20 µg/ml to 100 µg/ml, more particularly from 30 µg/ml to 100 µg/ml, especially from 40 µg/ml to 60 µg/ml. Preferably, the specified volume includes the volume of said tissue or organ as well as the volume of the (antibody-containing) solution, in which said tissue or organ is incubated.

When incubating tissues and/or organs with an antibody-containing solution, the skilled person will readily perform such incubation such as by means of a suitable container.

The selection of suitable amounts of antibody is well within the expertise of the skilled person. Generally, higher amounts or concentrations, respectively, of antibody are preferred where the graft comprises or is a tissue or an organ. Moreover, the selection of an exact amount or a concentration, respectively, of antibody used will also depend on the size of such tissue or organ.

In preferred embodiments, the above in vitro method or use is for reducing the likelihood of any one of the group consisting of GvHD, donor graft rejection, and organ rejection; particularly of GvHD, upon transplantation of said graft. In preferred embodiments, the above in vitro method or use is for achieving tolerance within the transplanted immunocompetent cells against the recipient's tissue upon transplantation of said modified graft. In preferred embodiments, the above in vitro method or use is for achieving tolerance or partial tolerance within the recipient's tissue against the modified graft upon transplantation of said modified graft. As used herein, a "partial tolerance" is a partial immunotolerance results in a reduced immune response. In preferred embodiments, the above in vitro method or use is for silencing cell activation within said graft.

Grafts including cell grafts containing immune cells are very well known to the person skilled in the art. As used herein, a "cell graft containing immune cells" is a graft comprising immune cells. The cell graft containing immune cells is not particularly limited.

According to the present invention, the graft may comprise a cell suspension, a tissue and/or an organ. Preferably, the graft is a cell suspension, a tissue and/or an organ. More preferably, the graft is selected from the group consisting of a cell suspension, a tissue and an organ.

In addition, in some preferred embodiments of the invention, the graft comprises stem cells. A graft comprising stem cells may also be referred to herein as a stem cell graft.

According to the present invention, the graft comprises cells bearing the CD4 antigen. Preferably, the graft comprises immune cells, particularly immune cells bearing the CD4 antigen. Such cells are well known to the person skilled in the art. In certain preferred embodiments, these immune cells are CD4 positive T lymphocytes or precursor cells thereof. In certain preferred embodiments, these immune cells include, but are not limited to T helper cells and cells belonging to the monocyte and macrophage lineage, such as monocytes and macrophages. Another example for such cells are microglia.

In some embodiments, said graft comprises, preferably is, a tissue, preferably a stem-cell-containing tissue. According to the present invention, suitable tissues include, but are not limited to blood, muscle, adipose tissue, connective tissue, epithelium, embryonic, and cellular tissue.

In other embodiments, said graft comprises, preferably is, an organ, preferably a stem-cell-containing organ. Suitable organs include, but are not limited to skin, intestine, kidney, and liver. Preferably, said organ is an intestine.

In preferred embodiments, said graft comprises, preferably is, a cell suspension, preferably a stem-cell-containing cell suspension. Suitable cell suspensions and methods for obtaining them are well known to the skilled person. For example, a cell suspension graft may be obtained by puncture of bones comprising bone marrow, e.g. puncture of the iliac crests or sterna or taken from stem cell niches throughout the whole body, e.g. fat tissue, tooth root, root of a hair and any other source mentioned above.

In preferred embodiments, the cell suspension, particularly the stem-cell-containing cell suspension, comprises bone marrow cells, non adherent bone marrow cells, peripheral blood cells, cord blood cells, cells from Wharton's jelly, placenta-derived cells, hair-root-derived cells, and/or fat-tissue-derived cells. In preferred embodiments, the cell suspension, particularly the stem-cell-containing cell suspension, comprises lymphocytes, monocytes and/or macrophages.

In certain preferred embodiments the graft, particularly the cell suspension, comprises any of bone marrow stem cells, peripheral blood stem cells, umbilical cord blood stem cells, adult stem cells of the bone marrow such as NA-BMCs, embryonic stem cells and/or reprogrammed adult stem cells (i.e. induced pluripotent cells).

In some particular embodiments, the graft does not consist of or does not comprise embryonic stem cells. In some particular embodiments, the graft does not consist of or does not comprise totipotent stem cells.

In preferred embodiments, the graft is a bone marrow suspension, particularly comprising bone marrow stem cells. Generally, the graft, particularly the bone marrow suspension, may additionally comprise any of stem cells comprised in blood cells, cord blood cells, donor lymphocytes, peripheral blood stem cells, adult stem cells of the bone marrow, embryonic stem cells and/or reprogrammed adult stem cells (i.e. induced pluripotent cells).

The graft, particularly the bone marrow suspension, may additionally comprise any of stem cells comprised in blood cells, cord blood cells, donor lymphocytes, peripheral blood stem cells, and/or adult stem cells of the bone marrow.

Generally, it is intended that the cell suspension also includes any cell suspension that comprises (any combination of) stem cells, optionally along with any (combination of) other cells.

The graft may also be a combination of grafts, such as a combination of one or more of the grafts referred to above, e.g. a combination of an organ and a cell suspension.

In a further aspect, the invention relates to a modified cell graft containing immune cells obtainable in accordance with an in vitro method of the invention.

Likewise, the invention relates to a modified cell graft containing immune cells, wherein said graft comprises anti CD4 antibodies bound to from 40% to 100% of the accessible CD4 epitopes of said graft. Preferably, the modified cell graft containing immune cells comprises anti CD4 antibodies bound to 50% to 100%, particularly 60% to 100%, particularly 70% to 100%, more particularly 80% to 100%, more particularly 90% to 100%, more particularly 95% to 100%, more particularly 99% to 100%, of the accessible CD4 epitopes of said graft. Most preferably, essentially all of the accessible CD4 epitopes of the cell graft containing immune cells are bound to anti CD4 antibodies.

In a further aspect, the invention relates to a modified graft of the invention for use in medicine.

In a further aspect, the invention relates to a modified graft of the invention for use in a method of treating in a subject one or more diseases treatable by transplantation.

The use of grafts including cell grafts containing immune cells in transplantation is well known in the art. The present invention provides a modified graft which is intended to avoid severe side effects which are associated with transplantation, as known in the art. Therefore, the modified grafts of the invention are used as it is known for the unmodified grafts.

Preferably, said subject is a mammalian subject, particularly a human. Preferably, said one or more diseases treatable by transplantation is/are selected from the group consisting of acute myeloid leukemia (AML); acute lymphoid leukemia (ALL); chronic myeloid leukemia (CML); myelodysplastic syndrome (MDS)/myeloproliferative syndrome; malign lymphomas, particularly selected from Morbus Hodgkin, high grade Non-Hodgkin Lymphoma (NHL), mantle cell lymphoma (MCL), low malign NHL, chronic lymphatic leukemia (CLL), multiple myeloma; severe aplastic anemia; thalassemia; sickle cell anemia; immunological defects particularly selected from severe combined immunodeficiency (SCID), Wiskott-Aldrich syndrome (WAS), and hemophagocytic lymphohistiocytosis (HLH); inborn errors of metabolism particularly selected from lysosomal storage disorders and disorders of peroxisomal function; autoimmune diseases; rheumatologic diseases; and recidivisms of any of the above.

Even more preferably, said one or more diseases are one or more hematological malignancies especially selected from acute myeloid leukemia (AML); acute lymphoid leukemia (ALL); chronic myeloid leukemia (CML); myelodysplastic syndrome (MDS)/myeloproliferative syndrome; malign lymphomas, particularly selected from Morbus Hodgkin, high grade Non-Hodgkin lymphoma (NHL), mantle cell lymphoma (MCL), low malign Non-Hodgkin lymphoma (NHL), chronic lymphatic leukemia (CLL), multiple myeloma; severe aplastic anemia; thalassemia; and sickle cell anemia.

Generally herein, said one or more diseases also include recidivisms of any of the above as well as any combination of diseases mentioned herein.

In the latter aspects, preferably, the graft is further defined as described hereinabove in connection with the in vitro methods of the invention. That is, the graft may preferably be selected from the group consisting of a cell suspension, a tissue and an organ. More preferably, said graft is selected from the group consisting of a cell suspension comprising bone marrow cells, non adherent bone marrow cells, peripheral blood cells, cord blood cells, cells from Wharton's jelly, placenta-derived cells, hair-root-derived cells, and/or fat-tissue-derived cells; a cell suspension comprising lymphocytes, monocytes and/or macrophages; a stem-cell-containing tissue; and a stem-cell-containing organ.

In some embodiments the treatment implies a reduced likelihood of developing any one of the group consisting of GvHD, donor graft rejection, and organ rejection; particularly of GvHD, upon transplantation of said graft. In other embodiments, the treatment implies tolerance within the transplanted immunocompetent cells against the recipient's tissue upon transplantation of said modified graft. In other embodiments, the treatment implies tolerance against the modified graft upon transplantation of said modified graft. In other embodiments, the treatment implies tolerance or partial tolerance within the recipient's tissue against the modified graft upon transplantation of said modified graft. In other embodiments, the treatment is for silencing cell activation within said graft. In preferred embodiments, the treatment implies/is for any combination of the above.

The amount of cells contained in the graft is not particularly limited. Any person skilled in the art will easily be able to choose appropriate amounts of a graft and of cells of the graft for transplantation. Furthermore, suitable guidance is also available e.g. from the specific guidelines for transplantation developed by the "Deutsche Bundesärztekammer", e.g. for human hematopoietic stem cells in patients.

Preferably, in accordance with the invention, particularly in case of the graft being a cell suspension, an amount of from $2\times10^6$ cells to $2\times10^{10}$ nucleated cells, particularly of from $4\times10^6$ to $1\times10^9$ nucleated cells, more particularly of from $1\times10^7$ to $1\times10^8$ nucleated cells are administered to said subject, preferably to the human subject.

Where the graft comprises or is a tissue or an organ, any suitable amounts of said tissue or organ may be administered to said subject. As will be understood by the skilled person, cell numbers in tissues or organs are difficult to determine. Particularly for this reason, the amount of cells contained in the graft is not particularly limited. Appropriate amounts will easily be determined or selected, respectively, by the skilled person, e.g. taking into consideration the particular type of subject, graft and/or disease to be treated. In case of organs, the administration of whole organs is preferred.

In the methods, modified grafts, and modified grafts for use of the present invention, the graft may additionally be incubated with soluble bioactive molecules, particularly with agents promoting immunosuppression, immunotolerance and/or formation of regulatory T cells or with any combination of such agents. Such agents preferably support the features or advantages, respectively, of the present methods, uses, modified grafts, or modified grafts for use described hereinabove, such as reducing the likelihood of any one of the group consisting of GvHD, donor graft rejection, and organ rejection; particularly of GvHD, upon transplantation of said graft or such as achieving tolerance upon transplantation of said modified graft. Such agents particularly include cytokines. In preferred embodiments, such agent(s) is/are selected from the group consisting of Il-2, TGF-β, rapamycin, retinoic acid, 4-1BB ligand, and anti-CD28 antibodies, or any combination thereof.

Likewise, in the modified grafts for use of the present invention, the graft may optionally be administered to the subject together with any medicament or combination of medicaments. Said medicament(s) may be administered prior to, together with and/or following transplantation. Suitable administration modes and routes are not particularly limited and will easily be chosen by the skilled person. Preferably, such medicament(s) support the features or advantages, respectively, of the present methods, uses, modified grafts, or modified grafts for use described hereinabove, such as reducing the likelihood of any one of the group consisting of GvHD, donor graft rejection, and organ rejection. Non-limiting examples for such medicaments include rapamycin and retinoic acid.

In a further aspect, the invention features a method of treating a subject in need of such treatment with a modified graft of the invention, particularly a modified graft obtainable in accordance with the in vitro method of the invention. In preferred embodiments, said graft, subject, treatment, and/or disease are as described hereinabove.

In a further aspect, the invention relates to the use of an anti CD4 antibody for the in vitro modification of a graft, particularly a cell graft containing immune cells, the modification comprising incubating said graft with said antibody for from 1 minute to 7 days, especially wherein the modification additionally comprises removing unbound antibody from said graft. In preferred embodiments, said use is further defined as described herein for the methods of the invention.

In a further aspect, the invention relates to the use of a modified graft of the invention for the manufacture of a medicament for the treatment of one or more diseases treatable by transplantation in a subject. In preferred embodiments, said use is further defined as described herein for the methods of the invention. In particular the graft, subject, treatment, and/or disease are preferably as described hereinabove.

In an even further aspect of the methods, uses, modified grafts, or modified grafts for use of the present invention, the anti CD4 antibody is replaced by any other CD4 ligand. Preferred CD4 ligands include, but are not limited to peptide ligands (including naturally occurring peptide ligands and peptide constructs) as well as aptamers. Such CD4 ligands are known in the art.

In an even further aspect, the graft referred to in the methods, uses, modified grafts, and modified grafts for use of the present invention, may or may not comprise stem cells. That is, according to the latter aspect, the cell graft containing immune cells may be replaced by any graft and includes a graft comprising stem cells as well as a graft not comprising stem cells. In other words, the graft of the invention or used in accordance with the invention may be any graft or may be a cell graft containing immune cells. In even other words, in certain embodiments the graft of the invention or used in accordance with the invention comprises stem cells, whereas in other embodiments, the graft of the invention or used in accordance with the invention does not comprise stem cells. In certain embodiments, the graft does not comprise isolated CD4+ cells.

As further described in the examples, the present inventors e.g. employed CD4−/− C57B1/6 mice transgenic for human CD4 and HLA-DR3 (triple transgenic mice, TTG; cf. Laub et al., 2000). The TTG mice have a complete functional murine immune system but without murine CD4 instead of human CD4 and where in addition to murine MHC-II the human HLA-DR3 is present. In this setting, the bone marrow cells can be taken as TTG grafts and incubated with anti human CD4 antibodies before transplantation in Balb/c wild-type mice. In this full MHC class I mismatch transplantation model, GvHD induction is highly presumably and a challenge for the anti CD4 antibody.

The engraftment of TTG/C57B16 donor cells in Balb/c mice was confirmed by flow cytometry. Stable Engraftment of H-2 Kd (C57B1/6), human CD4, HLA-DR, and a decrease of murine CD4 after transplantation indicates a full donor (TTG) hematopoiesis, first observed 12 days after transplantation. GvHD was confirmed by survival analysis, scoring system and histology. Severity of GvHD was higher by using TTG donor cells than C57B1/6 wild-type donor cells. Survival of GvHD mice treated with anti CD4 antibody was significantly increased from 0 to 83%. Without antibody treatment, GvHD mice died within 19-35 days. Used anti CD4 antibodies effectively suppress GvHD development after murine HSCT in a full MHC mismatch model (TTG mice in Balb/c mice). This unique transplantation model allows direct testing of anti human CD4 antibodies in mice by a stable murine GvHD model using TTG mice as donors. There was no induction of GvHD after anti human CD4 pre-treatment of bone marrow grafts from TTG mice. These findings are considered relevant for the refinement of strategies for suppression of reactive T cell clones.

In an even further aspect, the invention relates to an anti CD4 antibody, selected from the group consisting of i) antibody 16H5.chimIgG4; ii) an antibody obtainable from a cell line CD4.16H5.chimIgG4 deposited with the DSMZ on Dec. 2, 2011; iii) an antibody comprising the VH and the VK of antibody 16H5.chimIgG4; iv) an antibody comprising a VH and a VK of an antibody obtainable from a cell line CD4.16H5.chimIgG4 deposited with the DSMZ on Dec. 2, 2011; v) an antibody comprising a combination of a VH disclosed in FIG. 12 and of a VK disclosed in FIG. 13, wherein said combination is selected from VH1/VK1, VH2/VK2, VH4/VK2 and VH4/VK4, especially wherein said combination is VH2/VK2.

In particular embodiments of this even further aspect, the anti CD4 antibody of the invention is "MAX.16H5". In particular embodiments, the anti CD4 antibody of the invention is an antibody obtainable from a deposit of biological material made by the Applicants with the DSMZ on Dec. 2, 2011. In particular embodiments, the anti CD4 antibody of the invention is an antibody obtainable from cells deposited by the Applicants with the DSMZ on Dec. 2, 2011. In particular embodiments, the anti CD4 antibody of the invention is an antibody obtainable from cells "MAX.16H5/30F16H5" deposited with the DSMZ on Dec. 2, 2011. In particular embodiments, the anti CD4 antibody of the invention is an antibody obtainable from cells "CD4.16H5.chimIgG4" deposited with the DSMZ on Dec. 2, 2011. In some embodiments, the anti CD4 antibody of the invention comprises VH1 of FIG. 12. In some embodiments, the anti CD4 antibody of the invention comprises VH2 of FIG. 12. In some embodiments, the anti CD4 antibody of the invention comprises VH4 of FIG. 12. In some embodiments, the anti CD4 antibody of the invention comprises VK1 of FIG. 13. In some embodiments, the anti CD4 antibody of the invention comprises VK2 of FIG. 13. In some embodiments, the anti CD4 antibody of the invention comprises VK4 of FIG. 13. In some embodiments, the anti CD4 antibody of the invention comprises SEQ ID NO: 10. In some embodiments, the anti CD4 antibody of the invention comprises SEQ ID NO: 8. In some embodiments, the anti CD4 antibody of the invention comprises SEQ ID NO: 4. In some embodiments, the anti CD4 antibody of the invention comprises SEQ ID NO: 20. In some embodiments, the anti CD4 antibody of the invention comprises SEQ ID NO: 18. In some embodiments, the anti CD4 antibody of the invention comprises SEQ ID NO: 14. In some embodiments, the anti CD4 antibody of the invention comprises VH1 of FIG. 12 and/or VK1 of FIG. 13. In some particularly preferred embodiments, the anti CD4 antibody of the invention comprises VH2 of FIG. 12 and/or VK2 of FIG. 13. In some embodiments, the anti CD4 antibody of the invention comprises VH4 of FIG. 12 and/or VK2 of FIG. 13. In some embodiments, the anti CD4 antibody of the invention comprises VH4 of FIG. 12 and/or VK4 of FIG. 13. In some embodiments, the anti CD4 antibody of the invention comprises SEQ ID NO: 10 and/or SEQ ID NO: 20. In some particularly preferred embodiments, the anti CD4 antibody of the invention comprises SEQ ID NO: 8 and/or SEQ ID NO: 18. In some embodiments, the anti CD4 antibody of the invention comprises SEQ ID NO: 4 and/or SEQ ID NO: 18. In some embodiments, the anti CD4 antibody of the invention comprises SEQ ID NO: 4 and/or SEQ ID NO: 14. In some embodiments, the anti CD4 antibody of the invention comprises the VH and the VK of the antibody 16H5.chimIgG4.

Generally, the invention also relates to embodiments, where the term "comprises" or an equivalent term is replaced by "has" or an equivalent term. For example, the invention generally also relates to embodiments, where the term "comprising" or an equivalent term is replaced by "having" or an equivalent term.

In the following, an additional aspect of the invention is described in detail:

In one facet, the said additional aspect of the present invention relates to an anti human CD4-antibody comprising a heavy chain immunoglobulin variable domain (VH) and a light chain immunoglobulin variable domain (VL), wherein at least one T cell epitope located outside the CDRs of said immunoglobulin variable domains is removed from said immunoglobulin variable domains.

Such antibodies are less immunogenic than their parental antibodies and, therefore, less likely to stimulate or activate T cells and, hence, are less likely to cause an undesired T cell mediated immune response against the antibody, e.g. in a human subject.

Moreover, advantageously, said antibodies substantially retain the capability of the corresponding non-modified antibody to bind to human CD4 and, preferably, further retain at least one of their advantageous features.

As used in said additional aspect of the invention, by "antibody" is meant inter alia a protein of the immunoglobulin family that is capable of combining, interacting or otherwise associating with an antigen.

In the context of said additional aspect of the present invention, the term "antibody" is preferably considered to also relate to antibody fragments including for example Fv, Fab, Fab' and F(ab')2 fragments. Such fragments may be prepared by standard methods The said additional aspect of the present invention preferably also contemplates the various recombinant forms of antibody derived molecular species well known in the art. Such species include stabilized Fv fragments including single chain Fv forms (e.g., scFv) comprising a peptide linker joining the VH and VL domains, or an Fv stabilized by interchain di-sulphide linkage (dsFv) and which contain additional cysteine residues engineered to facilitate the conjoining of the VH and VL domains. Equally, other compositions are familiar in the art and could include species referred to as "minibodies"; and single variable domain "dAbs." Other species still may incorporate means for increasing the valency of the modified antibody V-region domain, i.e. species having multiple antigen binding sites for example by the engineering of dimerisation domains (e.g., "leucine zippers") or also chemical modification strategies. Moreover, the term "antibody" preferably also relates to multimers of scFv such as diabodies, triabodies or tetrabodies, tandabs, flexibodies, bispecific antibodies, and chimeric antibodies. According to the said additional aspect of the present invention, the term "anti human CD4-antibody" preferably refers to an antibody as defined above, which has the ability to bind to human CD4. Moreover, as used in said additional aspect of the invention, the term "non-modified antibody" or "parental antibody" preferably refers to a corresponding anti human CD4-antibody wherein, as opposed to the antibodies of the said additional aspect of the present invention, no T cell epitope located outside the CDRs of said immunoglobulin variable domains is removed from the immunoglobulin variable domains. The term "antigen" is preferably used in said additional aspect of the invention to refer to a substance that is capable of interacting with the antibody. In the context of the antibody of the said additional aspect of the present invention the antigen is preferably meant to be CD4, particularly human CD4. "CD4" or "cluster of differentiation 4" refers to a protein, more precisely a surface glycoprotein, well known to the person skilled in the art. In the present context CD4 may preferably also refer to a fragment of full-length CD4, or an otherwise modified form of CD4, provided that the fragment or otherwise modified form still functions as an antigen in the context of the antibody of the said additional aspect of the present invention. The term "immunoglobulin domain" is preferably used in said additional aspect of the invention to inter alia refer to a protein domain comprising an immunoglobulin fold. Immunoglobulin domains and proteins are well-known in the art. The term "VH" is preferably used in said additional aspect of the invention to refer to the heavy chain variable region of the heavy chain of an antibody. The "heavy chain variable region" is also referred to as "heavy chain immunoglobulin variable domain". Also these terms are well-known in the art. The term "VL" is preferably used in said additional aspect of the invention to refer to the light chain variable region of the light chain of an antibody. The "light chain variable region" is also referred to as "light chain immunoglobulin variable domain". Also these terms are well-known in the art.

Preferably, a heavy chain immunoglobulin variable domain and a light chain immunoglobulin variable domain together provide the binding surface capable of interacting with the antigen.

As used in said additional aspect of the invention, VH preferably means a polypeptide that is about 110 to 125 amino acid residues in length, the sequence of which corresponds to any of the specified VH chains in said additional aspect of the invention which in combination with a VL are capable of binding CD4 antigen. Similarly, VL preferably means a polypeptide that is about 95-130 amino acid residues in length the sequence of which corresponds to any of the specified VL chains in said additional aspect of the invention which in combination with a VH are capable of binding the CD4 antigen.

Full-length immunoglobulin heavy chains have preferably a molecular weight of about 50 to 70 kDa and are usually encoded by a VH gene at the N-terminus and one of the constant region genes (e.g., [gamma], [alpha] or [epsilon]) at the C-terminus. Similarly, full-length light chains have preferably a molecular weight of about 25 kDa and are usually encoded by a V-region gene at the N-terminus and a [kappa] or [lambda] constant region gene at the C-terminus.

The light chain of an antibody may be a "lambda" ("λ") type chain or a "kappa" ("κ") type chain. Accordingly, the light chain variable region may be a "lambda" ("Vl", "Vλ") type light chain variable region or a "kappa" ("Vk", "Vκ") type light chain variable region.

In common with numerous monoclonal antibodies the light chain preferably is a "kappa" ("κ") type chain. Accordingly, VL is preferably a Vk ("VK", "Vκ") type chain.

In the context of the said additional aspect of the present invention, there are provided a number of different heavy chain immunoglobulin variable domain sequences and light chain immunoglobulin variable domain sequences. The present disclosure provides no limit to the possible combinations of said variable domain sequences that may be comprised in a complete antibody molecule.

Preferably, the antibody of the said additional aspect of the present invention comprises two identical heavy chain immunoglobulin variable domains and two identical light chain immunoglobulin variable domains, wherein said heavy chain immunoglobulin variable domains and light chain immunoglobulin variable domains are selected from the variable domains disclosed in said additional aspect of the invention.

According to the said additional aspect of the present invention, the term "T cell epitope" preferably refers to a peptide sequence, which has a potential to bind to MHC molecules, preferably MHC class II molecules. Such sequences, in complex with MHC class II, may stimulate T cells and/or bind (without necessarily activating) T cells.

Preferably, the term "T cell epitope" refers to a peptide sequence, which, when bound to MHC class II molecules, can be recognized by a T cell receptor (TCR), and which can, at least in principle, cause the stimulation or activation of the corresponding T cell by engaging the TCR to promote a T cell response.

In order to identify T cell epitopes of an antibody, any of the in silico methods or in vitro methods which are known to a person skilled in the art and/or which are described or referred to in the present application, may be used.

Preferably, a T cell epitope consists of eight or more amino acids, more preferably of eight to twenty amino acids, more preferably of eight to eleven amino acids, particularly preferred of nine amino acids.

The term "peptide" as used in said additional aspect of the invention, is preferably a compound that includes two or more amino acids, which are linked together by a peptide bond. Some peptides may contain only a few amino acid units. In the art, short peptides, e.g. peptides having less than ten amino acid units, are sometimes referred to as "oligopeptides" whereas peptides containing a larger number of amino acid residues, e.g. 10 to 100 or more than 100, are usually referred to as "polypeptides".

Throughout the said additional aspect of the present invention, a T cell epitope is preferably said to be "removed" when T cell mediated immune response based on said epitope against the antibody is reduced or, preferably, eliminated.

Preferably, T cell mediated immune response against the antibody is reduced (preferably eliminated), when the potential of the T cell epitope to bind to MHC molecules, preferably MHC class II molecules, is reduced (preferably eliminated).

According to an exemplary method described in Example 2, a modified T cell epitope may be tested in silico for binding MHC class II alleles. In this method, a T cell epitope is considered to be "removed", when a lower number or no MHC Class II alleles are predicted to bind to the modified T cell epitope (see Example 2).

Other methods to measure the reduction or elimination of T cell mediated immune response are well known to the person skilled in the art and include, for example, in vitro MHC class II binding assays, utilizing either purified MHC class II molecules or homozygous immortalized B cell lines, or ex vivo T cell proliferation assays.

The removal of a T cell epitope may result in a decreased, preferably absent, immunogenicity displayed by the antibody. The term "immunogenicity" inter alia relates to an ability to provoke, induce or otherwise facilitate a humoral and or T cell mediated response in a host animal, in particular where the host animal is a human, and/or an ability to elicit a response in a suitable in vitro assay. For example, the immunogenicity is said to be reduced if it is reduced compared to a corresponding parental antibody, e.g., a non-modified rodent or chimeric (rodent V-regions; human constant regions) monoclonal antibody.

As used in said additional aspect of the invention, the term "CDR" preferably refers to the "complementarity-determining region" of an antibody, i.e. to one of the hypervariable regions within an immunoglobulin variable domain contributing to the determination of antibody specificity. CDRs are well known to a person skilled in the art. Typically, both the heavy chain immunoglobulin variable domain and the light chain immunoglobulin variable domain contain three CDRs. The CDRs in immunoglobulin variable domains may for example be identified and defined according to the methods developed by Kabat, which are well-known to a person skilled in the art. According to a preferred embodiment of the said additional aspect of the present invention, the CDRs are defined according to Kabat (Kabat et al. (1991).

As used in said additional aspect of the invention, a removed T cell epitope is preferably said to be "located outside the CDRs of the immunoglobulin variable domains", when the sequence of the T cell epitope which is to be removed does not overlap with any of the CDRs of said immunoglobulin variable domains. Besides, a removed T cell epitope is also said to be "located outside the CDRs of the immunoglobulin variable domains" in a case, in which the sequence of the T cell epitope which is to be removed does overlap with any of the CDRs of said immunoglobulin variable domains, in which, however, all of the alterations which have been made to such T cell epitope have been made outside the CDRs of the immunoglobulin variable domains.

The anti human CD4-antibody of the said additional aspect of the present invention may be a polyclonal antibody or a monoclonal antibody. Preferably, the antibody is a monoclonal antibody.

According to a preferred embodiment, the antibody is derived from the monoclonal antibody produced by hybridoma cell line ECACC 88050502.

The antibody produced by the hybridoma cell line ECACC 88050502 is a CD4 antibody, and more specifically a monoclonal mouse anti human CD4-antibody, also referred to as 30F16H5, which is, for example, disclosed in DE 3919294. Said antibody is obtainable from the hybridoma cell line which was deposited with the ECACC (accession number 88050502).

An antibody of the said additional aspect of the present invention is said to be "derived" from the monoclonal antibody produced by hybridoma cell line ECACC 88050502, when it has been obtained by any suitable method known to the person skilled in the art using the sequence of the monoclonal antibody produced by hybridoma cell line ECACC 88050502, or by using the hybridoma cell line ECACC 88050502.

Preferably, the antibody has the CDRs of the antibody produced by the hybridoma cell line ECACC 88050502, or the antibody has the CDRs of SEQ ID NO: 2 and SEQ ID NO: 12.

The CDRs of SEQ ID NO: 2 and SEQ ID NO: 12 have the sequences highlighted in italics in FIG. 12(a) and FIG. 13(a), which figures depict preferred immunoglobulin variable domain sequences of the parental anti human CD4-antibody 30F16H5 (SEQ ID NO: 2 and SEQ ID NO: 12). In each of FIG. 12(a) and FIG. 13(a) three CDRs are shown. Here, the CDRs in FIG. 12(a) are formed by amino acids 31-35, 50-66 and 99-109 of SEQ ID NO: 2 and the CDRs in FIG. 13(a) are formed by amino acids 24-33, 50-55 and 88-96 of SEQ ID NO: 12.

Antibodies having the CDRs of the antibody produced by the hybridoma cell line ECACC 88050502, or of SEQ ID NO: 2 and SEQ ID NO: 12 have a high potential to bind the human CD4 with an affinity comparable to that of the parental antibody 30F16H5.

In another preferred embodiment of the antibody of the said additional aspect of the present invention, with the exception of the differences due to the removal of one or more T cell epitopes from said immunoglobulin variable domains, the heavy chain immunoglobulin variable domain is identical to the heavy chain immunoglobulin variable domain of the antibody produced by the hybridoma cell line ECACC 88050502, or comprises a sequence identical to SEQ ID NO: 2; and the light chain immunoglobulin variable domain is identical to the light chain immunoglobulin variable domain of the antibody produced by the hybridoma cell line ECACC 88050502, or comprises a sequence identical to SEQ ID NO: 12.

As described in Example 2b, the current inventors have discovered and herein disclose T cell epitopes of the parental anti human CD4-antibody 30F16H5, which regions are e.g. depicted in Table 5 and Table 6 below.

This T cell epitopes referred to in said additional aspect of the invention as EH1 to EH10 ("T cell epitope of heavy chain variable region" 1 to 10) are individually depicted in Table 5 (SEQ ID NOs: 21-30) and the T cell epitopes referred to in said additional aspect of the invention as EL1 to EL11 EH10 ("T cell epitope of light chain variable region" 1 to 11) are individually depicted in Table 6 (SEQ ID NOs: 31-41). Each of these T cell epitopes may also be described on basis of their position on the sequences of the respective parental variable regions SEQ ID NO: 2 and SEQ ID NO: 12, respectively.

Accordingly, in a preferred embodiment of the said additional aspect of the present invention, the at least one T cell epitope is selected from the group consisting of the T cell epitopes of the heavy chain immunoglobulin variable domain at position 4 to 12 of SEQ ID NO: 2 (EH1), position 10 to 18 of SEQ ID NO: 2 (EH2), position 11 to 19 of SEQ ID NO: 2 (EH3), position 20 to 28 of SEQ ID NO: 2 (EH4), position 37 to 45 of SEQ ID NO: 2 (EH5), position 70 to 78 of SEQ ID NO: 2 (EH6), position 73 to 81 of SEQ ID NO: 2 (EH7), position 83 to 91 of SEQ ID NO: 2 (EH8), position 107 to 115 of SEQ ID NO: 2 (EH9), position 110 to 118 of SEQ ID NO: 2 (EH10), and the T cell epitopes of the light chain immunoglobulin variable domain at position 2 to 10 of SEQ ID NO: 12 (EL1), position 3 to 11 of SEQ ID NO: 12 (EL2), position 10 to 18 of SEQ ID NO: 12 (EL3), position 11 to 19 of SEQ ID NO: 12 (EL4), position 45 to 53 of SEQ ID NO: 12 (EL5), position 53 to 61 of SEQ ID NO: 12 (EL6), position 59 to 67 of SEQ ID NO: 12 (EL7), position 61 to 69 of SEQ ID NO: 12 (EL8), position 62 to 70 of SEQ ID NO: 12 (EL9), position 70 to 78 of SEQ ID NO: 12 (EL10), and position 97 to 105 of SEQ ID NO: 12 (EL11).

It is understood that under certain circumstances additional regions of sequence to those disclosed in said additional aspect of the invention can become immunogenic epitopes, for example in the event of infection with a pathogen expressing a protein or peptide with a similar sequence to that of the present case.

According to a preferred embodiment of the said additional aspect of the present invention, the at least one T cell epitope is removed by alteration of at least one amino acid residue.

In particular, as used in said additional aspect of the invention, the "alteration" or "modification" of the at least one amino acid residue preferably may be any of the following the substitution of at least one originally present amino acid residue by other amino acid residue,
the addition of at least one amino acid residue;
the deletion of at least one originally present amino acid residue;
the chemical modification of at least one amino acid residue; or a combination thereof.

Reference to the term "alteration" of at least one amino acid residue also includes a situation, wherein, if necessary, additional alteration(s), usually by substitution, addition or deletion of specific amino acid(s), are effected within the same T cell epitope or elsewhere in the antibody molecule to substantially retain the capability of the corresponding non-modified antibody to bind to human CD4. More preferably, such additional alteration(s) may be effected in order to additionally retain one or more of the advantageous features of the antibody.

Preferably, one or more alterations are effected at one or more residues from any or all of EH1 to EH10 and/or EL1 to EL11, preferably any or all of EH1 to EH10 and EL1 to EL11.

Particularly preferred, the alteration(s) are effected at one ore more amino acids commonly designated as "pocket residues", since they are engaged by the pockets of the MHC binding grooves. As will be understood by a person skilled in the art, said pocket residues constitute residues which are of particular relevance to immunogenicity and, hence, are more likely to reduce or, preferably, eliminate T cell mediated immune response against the antibody. Generally, it is particularly preferred to provide modified antibody molecules in which amino acid alteration is conducted within the most immunogenic regions of the parental antibody.

However, amino acid alterations, either singly within a given epitope or in combination within a single epitope may not only be made at positions equating to pocket residues with respect to the MHC class II binding groove, but at any point within the peptide sequence. All such alterations fall within the scope of the said additional aspect of the present invention.

Moreover, as will be clear to the person skilled in art, multiple alternative sets of alterations could be arrived at which achieve the removing of epitopes. The resulting sequences would, however, remain broadly homologous with the specific compositions disclosed in said additional aspect of the invention and therefore fall under the scope of the invention. It would be typical to arrive at sequences that were around 70%, or around 90%, or around 95%, or around 99% or more homologous with the present specified sequences over their least homologous region and yet remain operationally equivalent. Such sequences would equally fall under the scope of the present.

Preferably, the alteration of the at least one amino acid residue is the substitution of one ore more amino acids.

Accordingly, in a preferred embodiment of the antibody of the said additional aspect of the present invention, at least one amino acid within the at least one T cell epitope is substituted by another amino acid for removing the at least one T cell epitope.

It is understood that single amino acid substitutions within a given T cell epitope is a preferred route by which the epitope may be eliminated. Besides, combinations of substitution within a single epitope may be contemplated and for example can be particularly appropriate where individually defined epitopes are in overlap with each other.

In various embodiments, more than 2 amino acid substitutions, or more than 3 amino acid substitutions, or more than 4 amino acid substitutions, or more than 5 amino acid substitutions, or more than 6 amino acid substitutions, or more than 7 amino acid, or more than 8, or more than 9, or more than 10, or more than 11 or more than 12 substitutions are made in the heavy chain and/or the light chain. In some embodiments, between 1 and 21, between 5 and 20, or between 7 and 14, amino acid substitutions are made in the heavy and light chain.

In each of the T cell epitopes EH1 to EH10 and EL1 to EL11 referred to above, 0, 1, 2, 3, 4, 5, 6, 7, 8, or 9 substitutions may be present, provided that at least one substitution is present and that the antibody retains its ability to bind to human CD4.

Preferably, the number of substitutions is selected such, that the number of MHC II alleles predicted to bind or bound, respectively, is significantly decreased. Preferably, said number is decreased to at least 50%, more preferably 40%, more preferably 30%, more preferably 20%, more preferably 10%, more preferably 5%, more preferably 2%, more preferably 1% and most preferably 0% as compared to the number of alleles bound when no substitutions are present.

As exemplified in Example 2b, in a particular assay, the "number of MHC II alleles bound", is the number of MHC class II alleles among a given panel of MHC class II alleles examined in the assay (e.g. 34 MHC class II alleles), which are found to be binding peptides for a T cell epitope at issue. Said number is said to be "decreased", when the number is reduced for a modified T cell epitope when compared to the unmodified T cell epitope of the parental antibody.

As disclosed herein, various modified anti human CD4-antibodies, in which one ore more to T cell epitopes are removed, have been created by means of MHC class II epitope removal involving amino acid substitution. Examples of particularly useful substitutions in this respect are provided in FIG. 12 and FIG. 13, disclosing particular individual substitutions, i.e. the individual substitutions highlighted in FIG. 12(e) and FIG. 13(e), which may be made in SEQ ID NO: 2 (cf. FIG. 12(a)) or SEQ ID NO: 12 (cf. FIG. 13(a)), respectively. These substitutions are also depicted in Table 5 (relating to the heavy chain immunoglobulin domain) and Table 6 (relating to the light chain immunoglobulin domain).

Hence, according to a preferred embodiment of the said additional aspect of the present invention, the at least one substitution is selected from the group consisting of T9S, V10E, A12K, Q19K, S28T, K38R, R40A, L70I, A72R, V73D, S91T, T115L, L116V in SEQ ID NO: 2, and I10T, M11L, L46A, V59S, I62S, S69D, R76S, L105I in SEQ ID NO: 12.

In a particularly preferred embodiment, 0, 1, 2, or 3 substitutions are within each of EH1 and EH6; 0, 1 or 2 substitutions are within each of EH2, EH5, and EH10; 0 or 1 substitutions are within each of EH3, EH4, EH7, EH8, and EH9; 0, 1 or 2 substitutions are within each of EL2, EL3, EL7, EL8, and EL9; and 0 or 1 substitutions are within each of EL1, EL4, EL5, EL6, EL10, and EL11, with the proviso that at least one substitution is present.

According to a embodiment of the said additional aspect of the present invention, 6, 8, or 10 T cell epitopes are removed from the heavy chain immunoglobulin variable domain, and/or 5, 9, 10, or 11 T cell epitopes are removed from the light chain immunoglobulin variable domain of the antibody of the said additional aspect of the present invention.

More preferably, 6, 8, or 10 T cell epitopes are removed from the heavy chain immunoglobulin variable domain, and 5, 9, 10, or 11 T cell epitopes are removed from the light chain immunoglobulin variable domain of the antibody of the said additional aspect of the present invention.

According to one embodiment, all T cell epitopes are removed from the immunoglobulin variable domains.

Furthermore, according to the said additional aspect of the present invention, exemplary groups of substitutions have been made in the immunoglobulin variable domains, which groups are comprised by SEQ ID NOs: 4, 6, 8, and 10 (depicted in FIG. 12(*b*)-(*e*)) and SEQ ID NOs: 14, 16, 18, and 20 (depicted in FIG. 13(*b*)-(*e*)).

Hence, further preferred embodiments of the said additional aspect of the present invention are anti human CD4-antibodies, wherein the heavy chain immunoglobulin variable domain comprises a sequence selected from the group consisting of SEQ ID NOs: 4, 6, 8, and 10; and/or the light chain immunoglobulin variable domain comprises a sequence selected from the group consisting of SEQ ID NOs: 14, 16, 18, and 20.

More preferably, the heavy chain variable domain comprises a sequence selected from the group consisting of SEQ ID NOs: 4, 6, 8, and 10; and the light chain variable domain comprises a sequence selected from the group consisting of SEQ ID NO: 14, 16, 18, and 20.

Even more preferred, the heavy chain immunoglobulin variable domain comprises a sequence identical to SEQ ID NO: 4 and the light chain immunoglobulin variable domain comprises a sequence identical to SEQ ID NO: 14; the heavy chain immunoglobulin variable domain comprises a sequence identical to SEQ ID NO: 4 and the light chain immunoglobulin variable domain comprises a sequence identical to SEQ ID NO: 20; the heavy chain immunoglobulin variable domain comprises a sequence identical to SEQ ID NO: 6 and the light chain immunoglobulin variable domain comprises a sequence identical to SEQ ID NO: 14; the heavy chain immunoglobulin variable domain comprises a sequence identical to SEQ ID NO: 6 and the light chain immunoglobulin variable domain comprises a sequence identical to SEQ ID NO: 16; the heavy chain immunoglobulin variable domain comprises a sequence identical to SEQ ID NO: 6 and the light chain immunoglobulin variable domain comprises a sequence identical to SEQ ID NO: 20; the heavy chain immunoglobulin variable domain comprises a sequence identical to SEQ ID NO: 8 and the light chain immunoglobulin variable domain comprises a sequence identical to SEQ ID NO: 16; the heavy chain immunoglobulin variable domain comprises a sequence identical to SEQ ID NO: 8 and the light chain immunoglobulin variable domain comprises a sequence identical to SEQ ID NO: 20; the heavy chain immunoglobulin variable domain comprises a sequence identical to SEQ ID NO: 10 and the light chain immunoglobulin variable domain comprises a sequence identical to SEQ ID NO: 14; the heavy chain immunoglobulin variable domain comprises a sequence identical to SEQ ID NO: 10 and the light chain immunoglobulin variable domain comprises a sequence identical to SEQ ID NO: 16; or the heavy chain immunoglobulin variable domain comprises a sequence identical to SEQ ID NO: 10 and the light chain immunoglobulin variable domain comprises a sequence identical to SEQ ID NO: 20.

As can be taken from Example 2, antibodies comprising these particular variable domain sequence combinations show advantageous features particularly as regards their binding affinity to the CD4 antigen.

Particularly preferred, the heavy chain immunoglobulin variable domain comprises a sequence identical to SEQ ID NO: 4 and the light chain immunoglobulin variable domain comprises a sequence identical to SEQ ID NO: 14; the heavy chain immunoglobulin variable domain comprises a sequence identical to SEQ ID NO: 6 and the light chain immunoglobulin variable domain comprises a sequence identical to SEQ ID NO: 16; the heavy chain immunoglobulin variable domain comprises a sequence identical to SEQ ID NO: 10 and the light chain immunoglobulin variable domain comprises a sequence identical to SEQ ID NO: 16; or the heavy chain immunoglobulin variable domain comprises a sequence identical to SEQ ID NO: 10 and the light chain immunoglobulin variable domain comprises a sequence identical to SEQ ID NO: 20.

As shown in Example 2c disclosed herein, the antibodies according to these embodiments show a binding to human CD4, which is improved when compared to the parental monoclonal mouse anti CD4-antibody 30F16H5, which was used as a reference.

Generally, as indicated above, the modified antibody of the present exhibits an ability to bind to human CD4. As used in said additional aspect of the invention, an antibody is preferably said to "substantially retain" its capability to bind to human CD4, if the affinity for its target antigen CD4 is at least 5%, more preferably at least 10%, more preferably at least 20%, more preferably at least 40%, more preferably at least 50%, more preferably at least 60%, more preferably at least 70%, more preferably at least 80%, more preferably at least 90%, more preferably at least 100% of the affinity exhibited by the non-modified monoclonal anti CD4-antibody.

Various methods for the measurement of the affinity of antibodies are well known to a person skilled in the art. Suitable methods include the measurement of the affinity via competition ELISA as described in Example 2c herein, or a Scatchard analysis or analysis using a Biacore (Perkin Elmer) or similar instrument.

In a preferred embodiment of the said additional aspect of the present invention, the affinity for its target antigen CD4 is within an order of magnitude higher or lower than the affinity exhibited by the parental anti-CD4 monoclonal antibody.

For example, the binding affinity of the antibody of the said additional aspect of the present invention to CD4 is preferably within one order of magnitude higher or lower than the binding affinity of the antibody produced by the hybridoma cell line ECACC 88050502.

More preferably, the binding affinity is twofold higher or lower than the binding affinity of the antibody produced by the hybridoma cell line ECACC 88050502.

According to particularly preferred embodiments, the antibody has a higher binding affinity to CD4 than the antibody produced by the hybridoma cell line ECACC 88050502.

Preferably, the modified antibodies disclosed in said additional aspect of the invention in additionally retain at least one and most preferably all of the functional activities of the parental anti human CD4-antibody. Embodiments of the said additional aspect of the present invention therefore encompass modified antibodies in which one or more, and most preferably all of the beneficial technical features associated with the therapeutic efficacy of the parental non-modified antibody are exhibited, while the antibody has a reduced ability to bind to MHC class II molecules and/or induces a weaker or no immune response in a subject.

Preferably, the anti human CD4-antibody heavy chain further comprises a human IgG4 constant region domain and the light chain further comprises a human kappa constant region domain. Accordingly, in another preferred embodiment, the heavy chain variable region of the antibody of the said additional aspect of the present invention is linked to a human IgG4 constant region domain, and the light chain variable region of the antibody of the said additional aspect of the present invention is linked to a human kappa constant region domain. IgG4 has a low propensity to stimulate effector functions such as ADCC (antibody dependent cell-mediated cytotoxicity) and CDC (complement-induced cell death) and cannot therefore stimulate a pro-inflammatory response in the patient.

In particular embodiments, the anti human CD4-antibody further comprises a human IgG4 constant region domain adjacent to a heavy chain variable region sequence selected from SEQ ID NOs: 4, 6, 8, and 10 and a human kappa constant region domain adjacent to a light chain variable region sequence selected from SEQ ID NOs: 14, 16, 18, 20.

As described hereinabove, these exemplary sequences for the heavy chain and light chain variable region, respectively, are preferred variable region sequences.

According to another facet of the said additional aspect of the present invention, the antibody of the said additional aspect of the present invention is obtained using the expression vectors pANTVhG4 and pANTVκ.

As a non-limiting example, the antibody of the said additional aspect of the present invention can be obtained using the expression vectors pANTVhG4 and pANTVK as described in Example 2. Besides, any other suitable method(s) well known to a person skilled may be employed, in which modified antibodies are constructed on basis of particular antibody sequences such as the ones contained in the expression vectors pANTVhG4 and pANTVκ.

In another facet, the said additional aspect of the present invention relates to a method of preparing the anti human CD4-antibody of the said additional aspect of the present invention comprising the following steps:

(i) providing the amino acid sequence of the antibody derivable from the hybridoma cell line ECACC 88050502 or part thereof;
(ii) identifying one or more T cell epitopes within the amino acid sequence of the antibody or part thereof by any method including determination of the binding of the peptides to MHC molecules using in vitro or in silico techniques or biological assays;
(iii) designing new sequence variants with one or more amino acids within the identified T cell epitopes modified in such a way to substantially reduce or eliminate binding of the peptides to MHC molecules measured by in vitro or in silico techniques or biological assays; and
(iv) constructing such sequence variants by recombinant DNA techniques and testing said sequence variants in order to identify one or more sequence variants having the properties of the anti human CD4-antibody of the said additional aspect of the present invention.

The identification of T cell epitopes according to step (ii) can be carried out according to methods described previously in the art. Suitable methods are e.g. disclosed in WO 98/59244; WO 00/34317; U.S. Application 20030153043, all incorporated herein by reference. In the method described above, sequence variants are preferably created in such a way to avoid creation of new T cell epitopes by the sequence variations unless such new T cell epitopes are, in turn, modified in such a way to substantially reduce or eliminate binding of peptides to MHC class II molecules. In practice, when conducting alterations to the protein sequence, it is preferably avoided that the contemplated changes introduce new immunogenic epitopes by re-testing the contemplated sequence for the presence of epitopes and or of MHC class II ligands by any suitable means.

In various embodiments, the modified antibodies of the said additional aspect of the present invention are generated by expression of different combinations of the VH and VL genes specified in said additional aspect of the invention. All such combinations of heavy and light chain are encompassed by the said additional aspect of the present invention.

Generally, constitution of the complete antibody molecule may be achieved by recombinant DNA techniques and methods for purifying and manipulating antibody molecules well known in the art. Necessary techniques are explained fully in standard literature, which is well-known to the skilled person.

The preferred molecules of this said additional aspect of the present invention can be prepared in any of several ways but is most preferably conducted exploiting routine recombinant methods. It is a relatively facile procedure to use the protein sequences and information provided in said additional aspect of the invention to deduce a polynucleotide (DNA) encoding any of the preferred antibody V-regions. This can be achieved for example using computer software tools such as the DNAstar software suite [DNAstar Inc, Madison, Wis., USA] or similar. Any such DNA sequence with the capability of encoding the preferred polypeptides of the present or significant homologues thereof, should be considered as embodiments of this said additional aspect of the present invention.

As a general scheme, any of the VH or VL chain genes can be made using gene synthesis and cloned into a suitable expression vector. In turn the expression vector is introduced into a host cell and cells selected and cultured. The antibody molecules are readily purified from the culture medium and formulated into a preparation suitable for therapeutic administration.

By way of a non-limiting example, one such scheme involves a gene synthesis process using panels of synthetic oligonucleotides. The genes are assembled using a ligase chain reaction (LCR) wherein the oligonucleotides featuring complementary ends are allowed to anneal followed by amplification and fill-in using a polymerase chain reaction (PCR). The PCR is driven by addition of an increased concentration of the flanking oligonucleotides to act as primers. The PCR products are assembled into full-length antibody genes by further PCR from vectors containing 5' and 3' immunoglobulin gene flanking regions and sub-cloning into expression vectors for expression of whole antibody. The assembled VH and VL genes can serve as templates for mutagenesis and construction of multiple variant antibody sequences such as any of those disclosed in said additional aspect of the invention. It is particularly convenient to use the strategy of "overlap extension PCR" as described by (Higuchi et al. (1998)), although other methodologies and systems could be readily applied.

Full-length immunoglobulin genes containing the variable region cassettes are most conveniently assembled using overlapping PCR and sub-cloned into expression vectors containing the desired immunoglobulin constant region domains. The expression vectors may be introduced into a mammalian or other host cell for example using electroporation techniques. The NS0 cell line is a non-immunoglobulin producing mouse myeloma, obtained from the European Collection of Animal Cell Cultures (ECACC) and is particularly suitable example host cell line for this procedure. Cell lines secreting antibody are expanded and antibody can be readily purified for example by use of protein A affinity chromatography (Harlow E & Lane D (2006)). The concentration of the purified antibody can be determined using an enzyme linked immunosorbent assay (ELISA) detecting the human kappa constant region of the antibodies of interest.

In as far as the said additional aspect of the present invention relates to modified anti-CD4 antibodies, compositions containing such modified antibodies or fragments of modified antibodies and related compositions are also considered to be within the scope of the invention.

Therefore, the said additional aspect of the present invention further relates to a pharmaceutical composition comprising the anti human CD4-antibody of the said additional aspect of the present invention and a pharmaceutically acceptable carrier.

The therapeutic compositions of the anti human CD4-antibody of the said additional aspect of the present invention may be used in conjunction with a pharmaceutically acceptable excipient. The pharmaceutical compositions according to the said additional aspect of the present invention are prepared conventionally, comprising substances that are customarily used in pharmaceuticals, including excipients, carriers, adjuvants, and buffers. The compositions can be administered, e.g., parenterally, enterally, intramuscularly, subcutaneously, intravenously, or other routes useful to achieve an effect. Conventional excipients include pharmaceutically acceptable organic or inorganic carrier substances suitable for parenteral, enteral, and other routes of administration that do not deleteriously react with the agents. For parenteral application, particularly suitable are injectable sterile solutions, preferably oil or aqueous solutions, as well as suspensions, emulsions or implants, including suppositories. Ampoules are convenient unit dosages. The pharmaceutical preparations can be sterilized and, if desired, mixed with stabilizers, wetting agents, emulsifiers, salts for influencing osmotic pressure, buffers, or other substances that do not react deleteriously with the active compounds.

The modified antibodies disclosed in said additional aspect of the invention are useful in a number of important diseases in man including especially autoimmune conditions including, but not limited to, multiple sclerosis, rheumatoid arthritis, systemic vasculitis, uveitis, inflammatory bowel disease and scleroderma and also for use in transplantations. Hence, the antibodies of the said additional aspect of the present invention can be used in therapeutic treatment. Non-limiting examples encompass a method of treating autoimmune conditions in a patient comprising administering an effective amount of a modified antibody according to the said additional aspect of the present invention. In various embodiments the autoimmune condition is multiple sclerosis, rheumatoid arthritis, systemic vasculitis, uveitis, inflammatory bowel disease or scleroderma. Another example is a method of immunosuppressing a patient prior to or subsequent to transplantation of an organ comprising administering to said patient an effective amount of an antibody according to the said additional aspect of the present invention. In one embodiment, the organ for transplantation is a renal transplant. The said additional aspect of the present invention also relates to methods for therapeutic treatment of humans using the modified antibody compositions. For administration to an individual, any of the modified antibody compositions would preferably be produced to be at least 80% pure and free of pyrogens and other contaminants.

Accordingly, in one further facet, the said additional aspect of the present invention relates to a method of therapeutic treatment comprising administering the antibody to a subject, preferably to a patient. Preferably, the method is for treating an autoimmune condition, particularly an autoimmune condition selected from multiple sclerosis, rheumatoid arthritis, systemic vasculitis, uveitis, inflammatory bowel disease and scleroderma. According to another preferred embodiment, the method is for immunosuppressing a patient prior to or subsequent to transplantation of an organ, particularly a kidney. Preferably, the subject is a human. Preferably, an effective amount of the antibody is administered.

In a related facet, the said additional aspect of the present invention relates to the use of the anti human CD4-antibody of the said additional aspect of the present invention for the manufacture of a medicament for therapeutically treating a subject. Preferably, the medicament is for treating an autoimmune condition, particularly an autoimmune condition selected from multiple sclerosis, rheumatoid arthritis, systemic vasculitis, uveitis, inflammatory bowel disease and scleroderma. According to another preferred embodiment, the medicament is for immunosuppressing a patient prior to or subsequent to transplantation of an organ, particularly a kidney. Preferably, the subject is a human.

In another related facet, the said additional aspect of the present invention relates to the antibody of the said additional aspect of the present invention for use in a method of therapeutic treatment. Preferably, the method is for treating an autoimmune condition, particularly an autoimmune condition selected from multiple sclerosis, rheumatoid arthritis, systemic vasculitis, uveitis, inflammatory bowel disease and scleroderma. According to another preferred embodiment, the method is for immunosuppressing a patient prior to or subsequent to transplantation of an organ, particularly a kidney. Preferably, the subject is a human.

In the methods of treatments and medical uses of the said additional aspect of the present invention, the actual dosage of the anti-CD4 antibodies of the said additional aspect of the present invention employed will depend on a variety of factors including the type and severity of disorder being treated, and other treatment modality or modalities selected. Guidance for dosage regimens is obtained from dosing of humanized anti-CD4 known in the art.

In a still other facet, the said additional aspect of the present invention relates to a nucleic acid encoding a heavy chain and/or a light chain immunoglobulin variable domain of the anti human CD4-antibody of the said additional aspect of the present invention. Preferably, the nucleic acid comprises a sequence selected from the group consisting of SEQ ID NOs: 3, 5, 7, 9, 13, 15, 17, and 19.

Also part of the said additional aspect of the present invention are nucleic acids nucleic acid encoding a heavy chain and/or a light chain immunoglobulin variable domain of the anti human CD4-antibody of the said additional aspect of the present invention, which differ from SEQ ID NOs: 3, 5, 7, 9, 13, 15, 17, and 19 due to the degeneracy of the genetic code.

Degeneracy in relation to polynucleotides refers to the fact well recognized in the art that in the genetic code many amino acids are specified by more than one codon. The degeneracy of the code accounts for 20 different amino acids encoded by 64 possible triplet sequences of the four different bases.

In another facet, the said additional aspect of the present invention relates to a vector comprising a nucleic acid as described above. Preferably, the nucleic acid is operably linked to an expression control sequence.

In some embodiments, the expression vector comprises a nucleic acid sequence encoding a V-region heavy or light chain comprising a modified substituted variant of SEQ ID NO: 2 or SEQ ID NO: 12 with a reduced number of T cell epitopes, operably linked to an expression control sequence. In various embodiments, the expression vector comprises or is derived from the pANTVhG4 vector (for VH) and the pANTVK vector for VL as depicted in FIG. 11.

In another facet, the said additional aspect of the present invention relates to a host cell comprising a nucleic acid as described above and/or at least one vector as described above. Preferably, the host cell comprises one or more vectors which each comprise a nucleic acid as described above. Preferably the host cell comprises two vectors which each comprise a nucleic acid as described above.

The said additional aspect of the present invention further relates to a method of preparing the anti human CD4-antibody of the said additional aspect of the present invention comprising culturing the host cell described above under conditions permitting expression under the control of suitable expression control sequence(s), and purifying said antibody from the medium of the cell.

In the following items 1 to 33 certain embodiments of the said additional aspect of the present invention are described:

1. An anti human CD4-antibody comprising a heavy chain immunoglobulin variable domain (VH) and a light chain immunoglobulin variable domain (VL), wherein at least one T cell epitope located outside the CDRs of said immunoglobulin variable domains is removed from said immunoglobulin variable domains.
2. The antibody of item 1, wherein the antibody is a monoclonal antibody.
3. The antibody of item 2, wherein the antibody is derived from the monoclonal antibody produced by hybridoma cell line ECACC 88050502.
4. The antibody of any one of items 1 to 3, wherein the antibody has the CDRs of the antibody produced by the hybridoma cell line ECACC 88050502, or wherein the antibody has the CDRs of SEQ ID NO: 2 and SEQ ID NO: 12.
5. The antibody of any one of items 1 to 4, wherein, with the exception of the differences due to the removal of one or more T cell epitopes from said immunoglobulin variable domains,
   the heavy chain immunoglobulin variable domain is identical to the heavy chain immunoglobulin variable domain of the antibody produced by the hybridoma cell line ECACC 88050502, or comprises a sequence identical to SEQ ID NO: 2; and
   the light chain immunoglobulin variable domain is identical to the light chain immunoglobulin variable domain of the antibody produced by the hybridoma cell line ECACC 88050502, or comprises a sequence identical to SEQ ID NO: 12.
6. The antibody of any one of items 1 to 5, wherein the at least one T cell epitope is selected from the group consisting of
   the T cell epitopes of the heavy chain immunoglobulin variable domain at position 4 to 12 of SEQ ID NO: 2 (EH1), position 10 to 18 of SEQ ID NO: 2 (EH2), position 11 to 19 of SEQ ID NO: 2 (EH3), position 20 to 28 of SEQ ID NO: 2 (EH4), position 37 to 45 of SEQ ID NO: 2 (EH5), position 70 to 78 of SEQ ID NO: 2 (EH6), position 73 to 81 of SEQ ID NO: 2 (EH7), position 83 to 91 of SEQ ID NO: 2 (EH8), position 107 to 115 of SEQ ID NO: 2 (EH9), position 110 to 118 of SEQ ID NO: 2 (EH10), and
   the T cell epitopes of the light chain immunoglobulin variable domain at position 2 to 10 of SEQ ID NO: 12 (EL1), position 3 to 11 of SEQ ID NO: 12 (EL2), position 10 to 18 of SEQ ID NO: 12 (EL3), position 11 to 19 of SEQ ID NO: 12 (EL4), position 45 to 53 of SEQ ID NO: 12 (EL5), position 53 to 61 of SEQ ID NO: 12 (EL6), position 59 to 67 of SEQ ID NO: 12 (EL7), position 61 to 69 of SEQ ID NO: 12 (EL8), position 62 to 70 of SEQ ID NO: 12 (EL9), position 70 to 78 of SEQ ID NO: 12 (EL10), and position 97 to 105 of SEQ ID NO: 12 (EL11).
7. The antibody of any one of items 1 to 6, wherein for removing said at least one T cell epitope at least one amino acid within said at least one T cell epitope is substituted by another amino acid.
8. The antibody of item 7, wherein the substitution is selected from the group consisting of
   T9S, V10E, A12K, Q19K, S28T, K38R, R40A, L70I, A72R, V73D, S91T, T115L, L116V in SEQ ID NO: 2, and I10T, M11L, L46A, V59S, I62S, S69D, R76S, L105I in SEQ ID NO: 12.
9. The antibody of any one of items 6 to 8,
   wherein 0, 1, 2, or 3 substitutions are within each of EH1 and EH6;
   wherein 0, 1 or 2 substitutions are within each of EH2, EH5, and EH10;
   wherein 0 or 1 substitutions are within each of EH3, EH4, EH7, EH8, and EH9;
   wherein 0, 1 or 2 substitutions are within each of EL2, EL3, EL7, EL8, and EL9; and
   wherein 0 or 1 substitutions are within each of EL1, EL4, EL5, EL6, EL10, and EL11, with the proviso that at least one substitution is present.
10. The antibody of any one of items 1 to 9, wherein 6, 8, or 10 T cell epitopes are removed from the heavy chain immunoglobulin variable domain, and/or
    wherein 5, 9, 10, or 11 T cell epitopes are removed from the light chain immunoglobulin variable domain.
11. The antibody of any one of items 1 to 10, wherein the heavy chain immunoglobulin variable domain comprises a sequence selected from the group consisting of SEQ ID NOs: 4, 6, 8, and 10; and/or wherein the light chain immunoglobulin variable domain comprises a sequence selected from the group consisting of SEQ ID NOs: 14, 16, 18, and 20.

12. The antibody of item 10 or 11, wherein the heavy chain immunoglobulin variable domain comprises a sequence identical to SEQ ID NO: 4 and the light chain immunoglobulin variable domain comprises a sequence identical to SEQ ID NO: 14;

the heavy chain immunoglobulin variable domain comprises a sequence identical to SEQ ID NO: 4 and the light chain immunoglobulin variable domain comprises a sequence identical to SEQ ID NO: 20;

the heavy chain immunoglobulin variable domain comprises a sequence identical to SEQ ID NO: 6 and the light chain immunoglobulin variable domain comprises a sequence identical to SEQ ID NO: 14;

the heavy chain immunoglobulin variable domain comprises a sequence identical to SEQ ID NO: 6 and the light chain immunoglobulin variable domain comprises a sequence identical to SEQ ID NO: 16;

the heavy chain immunoglobulin variable domain comprises a sequence identical to SEQ ID NO: 6 and the light chain immunoglobulin variable domain comprises a sequence identical to SEQ ID NO: 20;

the heavy chain immunoglobulin variable domain comprises a sequence identical to SEQ ID NO: 8 and the light chain immunoglobulin variable domain comprises a sequence identical to SEQ ID NO: 16;

the heavy chain immunoglobulin variable domain comprises a sequence identical to SEQ ID NO: 8 and the light chain immunoglobulin variable domain comprises a sequence identical to SEQ ID NO: 20;

the heavy chain immunoglobulin variable domain comprises a sequence identical to SEQ ID NO: 10 and the light chain immunoglobulin variable domain comprises a sequence identical to SEQ ID NO: 14;

the heavy chain immunoglobulin variable domain comprises a sequence identical to SEQ ID NO: 10 and the light chain immunoglobulin variable domain comprises a sequence identical to SEQ ID NO: 16; or the heavy chain immunoglobulin variable domain comprises a sequence identical to SEQ ID NO: 10 and the light chain immunoglobulin variable domain comprises a sequence identical to SEQ ID NO: 20.

13. The antibody of item 12, wherein the heavy chain immunoglobulin variable domain comprises a sequence identical to SEQ ID NO: 4 and the light chain immunoglobulin variable domain comprises a sequence identical to SEQ ID NO: 14;

the heavy chain immunoglobulin variable domain comprises a sequence identical to SEQ ID NO: 6 and the light chain immunoglobulin variable domain comprises a sequence identical to SEQ ID NO: 16;

the heavy chain immunoglobulin variable domain comprises a sequence identical to SEQ ID NO: 10 and the light chain immunoglobulin variable domain comprises a sequence identical to SEQ ID NO: 16; or the heavy chain immunoglobulin variable domain comprises a sequence identical to SEQ ID NO: 10 and the light chain immunoglobulin variable domain comprises a sequence identical to SEQ ID NO: 20.

14. The antibody of any one of items 1 to 13, wherein the binding affinity of the antibody to CD4 is within one order of magnitude higher or lower than the binding affinity of the antibody produced by the hybridoma cell line ECACC 88050502.

15. The antibody of item 14, wherein the binding affinity of the antibody to CD4 is within twofold higher or lower than the binding affinity of the antibody produced by the hybridoma cell line ECACC 88050502.

16. The antibody of item 14 or 15, wherein the antibody has a higher binding affinity to CD4 than the antibody produced by the hybridoma cell line ECACC 88050502.

17. The antibody of any one of items 1 to 16,
   (a) wherein the antibody has a reduced ability to bind to MHC class H molecules;
   (b) wherein the antibody induces a weaker immune response in a subject;
   (c) wherein the protein is a full-length antibody;
   (d) wherein the antibody is a chimeric antibody; and/or
   (e) wherein the substitution(s) is/are within the most immunogenic regions of the parent molecule.

18. The antibody of any one of items 1 to 17, wherein the heavy chain variable region is linked to a human IgG4 constant region domain, and wherein the light chain variable region is linked to a human kappa constant region domain.

19. The antibody of item 18, wherein the antibody is obtained using the expression vectors pANTVhG4 and pANTVκ.

20. A method of preparing an antibody of any one of items 1 to 19 comprising the following steps
(i) providing the amino acid sequence of the antibody derivable from the hybridoma cell line ECACC 88050502 or part thereof;
(ii) identifying one or more T cell epitopes within the amino acid sequence of the antibody or part thereof by any method including determination of the binding of the peptides to MHC molecules using in vitro or in silico techniques or biological assays;
(iii) designing new sequence variants with one or more amino acids within the identified T cell epitopes modified in such a way to substantially reduce or eliminate binding of the peptides to MHC molecules measured by in vitro or in silico techniques or biological assays; and
(iv) constructing such sequence variants by recombinant DNA techniques and testing said sequence variants in order to identify one or more sequence variants having the properties of an antibody of any one of items 1 to 20.

21. A pharmaceutical composition comprising an antibody of any one of items 1 to 19 and a pharmaceutically acceptable carrier.

22. Use of an antibody of any one of items 1 to 19 for the manufacture of a medicament for therapeutically treating a subject.

23. The use of item 22, wherein the medicament is for treating an autoimmune condition, particularly an autoimmune condition selected from multiple sclerosis, rheumatoid arthritis, systemic vasiculitis, uveitis, inflammatory bowel disease and scleroderma; or wherein the medicament is for immunosuppressing a patient prior to or subsequent to transplantation of an organ, particularly a kidney.

24. The antibody of any one of items 1 to 19 for use in a method of therapeutic treatment.

25. The antibody of item 24, wherein the method is for treating an autoimmune condition, particularly an autoimmune condition selected from multiple sclerosis, rheumatoid arthritis, systemic vasiculitis, uveitis, inflammatory bowel disease and scleroderma; or wherein the method is for immunosuppressing a patient prior to or subsequent to transplantation of an organ, particularly a kidney.

26. The use or antibody of any one of items 22 to 25, wherein said subject is a human.

27. A nucleic acid encoding a heavy chain and/or a light chain immunoglobulin variable domain of an antibody of any one of items 1 to 19.

28. The nucleic acid of item 27, comprising a sequence selected from the group consisting of SEQ ID NOs 3, 5, 7, 9, 13, 15, 17, and 19.

29. A vector comprising a nucleic acid of item 27 or 28.

30. The vector of item 29, wherein the nucleic acid is operably linked to an expression control sequence.

31. The antibody of any one of these items, wherein the antibody is
   i) antibody 16H5.chimIgG4,
   ii) an antibody obtainable from a cell line CD4.16H5.chimIgG4 deposited with the DSMZ on Dec. 2, 2011.

32. A host cell comprising a nucleic acid of item 27 or 28 and/or at least one vector of any one of items 29 to 31.

33. A method of preparing an antibody of any one of items 1 to 19 comprising culturing the host cell of item 32 under conditions permitting expression under the control of suitable expression control sequence(s), and purifying said antibody from the medium of the cell.

The present invention further relates to alternative embodiments of embodiments disclosed herein, where the term "ECACC 88050502" is replaced by "MAX.16H5/30F16H5". Likewise, the present invention further relates to embodiments, where the term "cell line ECACC 88050502" as used herein, or an equivalent term, is replaced by the term "cell line MAX.16H5/30F16H5" or an equivalent term.

The present invention further relates to alternative embodiments of embodiments disclosed herein, where the term "ECACC 88050502" is replaced by "CD4.16H5.chimIgG4". Likewise, the present invention further relates to embodiments, where the term "cell line ECACC 88050502" as used herein, or an equivalent term, is replaced by the term "cell line CD4.16H5.chimIgG4" or an equivalent term.

In the following, the present invention is illustrated by figures and examples which are not intended to limit the scope of the present invention.

EXAMPLES

Example 1

Animals

Donor C57B1/6 CD4k/o mice, C57B1/6 wild-type mice and recipient Balb/c wild-type mice were bred at the Animal Facility at the University of Leipzig. The mice strain was maintained under standardized conditions. The C57B1/6 CD4k/o mice have a stable C57B1/6 background, in which the murine CD4 molecule is knocked out and express a human CD4. The CD4 transgene includes its own promoter ligated to a murine CD4 enhancer element thus leading to T cell subset-specific expression. CD8+ cells are not affected in TTG mice. Furthermore, these mice express the HLA-DR3 molecule in addition to the murine MHC II complex. The TTG mice have complete functional murine immune system which is modified with regard to CD4 and HLA-DR. The mice were fed ad libitum. As donors, C57B1/6 and Balb/c mice were purchased from Charles River (Sulzfeld, Germany; http://jaxmice.jax.org).

All mice were housed, treated or handled in accordance with the guidelines of the University of Leipzig Animal Care Committee and the Regional Board of Animal Care for Leipzig (animal experiment registration number 28/08).

Statistic Analysis

All data are presented as means±SD. Statistic analysis and graphic presentation were made using SigmaPlot 10.0/SigmaStat 3.5 software (SYSTAT, Erkrath, Germany).

Irradiation Protocol

For irradiation of mice the X-Ray apparatus (D3225, Orthovoltage, Gulmay Medical, Camberley, UK) was adjusted for animal irradiation. Five animals were irradiated in parallel in a plexiglass container (divided in five spaces per 0.5 cm×64.0 cm), depending on their weight. The average radiation dose was 8.5 Gy.

Preparation of Bone Marrow Cells and Splenocytes

Bone marrow cells (BMCs) were freshly obtained from tibiae and femora from C57B1/6 CD4k/o mice or C57B1/6 wild-type mice under sterile conditions. Therefore, the musculature and tendons carefully prepared from the bone and distal and proximal ends were removed. With a thin needle (0.4×19 mm), bone marrow cells were rinsed with sterile PBS and collected in 50 ml tubes. A single cell suspension was achieved by careful resuspension through a needle. Following, cells were washed once in PBS (1×) at 300×g for 10 min and resuspended again in PBS (1×) to determine cell counts using a counting chamber and staining with Tuerk staining solution. After this, bone marrow cells were washed once again in PBS (1×) at 300×g for 10 min and the cell pellet was resuspended in Dulbecco's modified Eagle's minimal essential medium (DMEM; Perbio, Bonn, Germany) without FCS. For the generation of a single cell splenocyte suspension from C57B1/6 CD4k/o mice or C57B1/6 wild-type mice, the spleen were removed immediately under sterile conditions after dead of mice, pressed through a cell strainer (100 µm) and collected in a 50 ml tube in PBS (1×). The single cell suspension was washed twice in PBS (1×) at 300×g for 10 min. Subsequently, the erythrocytes were lysed in lysis buffer containing 0.155 mol $NH_4Cl$, 0.01 mol $KHCO_3$ and 0.01 mol EDTA-Na (pH 7.3) in sterile PBS. Cells were washed again, resuspended in DMEM culture medium without FCS and the cell number was determined. Bone marrow cells and splenocytes were adjusted to the desired cell number before antibody incubation.

As will be readily understood by the skilled person, the use of splenocytes in the present Examples occurs for operational reasons—an additional application of splenocytes is actually not required according to the invention, particularly as far as human subjects are concerned.

Antibody Incubation

For the antibody incubation the needed amount of Max16H5 antibody was dissolved just before use to a final concentration of 1 mg/ml in DMEM (without FCS). Following, $1.4×10^8$ of bone marrow cells and $1.4×10^8$ of splenocytes from C57B1/6 CD4k/o or C57B1/6 wild-type mice were incubated with 800 µg Max16H5 in 15 ml DMEM without FCS for 1 h at room temperature in the dark. As control, bone marrow cells and splenocytes of C57B1/6 CD4k/o mice or C57B1/6 wild-type mice without antibody treatment were also incubated in DMEM without FCS under the same conditions. After 1 h of incubation cells were centrifuged at 300×g for 10 min to pellet them and washed once in PBS (1×) at 300×g for 10 min to remove unbound antibodies.

Cell Transplantation

For co-transplantation experiments $2\times10^7$ bone marrow cells of CD4k/o mice treated with Max16H5 were added to $2\times10^7$ splenocytes of CD4k/o mice treated with Max16H5. The cell concentration was adjusted in a final volume of 150 µl sterile 0.9% NaCl. The same was done for bone marrow cells and splenocytes of C57Bl/6 wild-type mice also treated with Max16H5. As a control, $2\times10^7$ untreated bone marrow cells of CD4k/o mice were added to $2\times10^7$ untreated splenocytes of CD4k/o mice or $2\times10^7$ bone marrow cells of C57B1/6 wild-type mice were added to $2\times10^7$ splenocytes of C57B1/6 wild-type mice. Following, the grafts were allogeneic transplanted by intravenous injection into the lateral tail vein of lethally irradiated recipient Balb/c wild-type mice. Survival, GvHD symptoms according Cooke et. al, 1996, and weights were assessed every day after transplantation.

Flow Cytometry

Before and after transplantation, recipient Balb/c wild-type mice were analyzed by flow cytometry.

Characterization of Splenocytes and Bone Marrow Cells of Donor CD4k/o Mice.

For cytometric analysis, cells were incubated with 2.5 µl of conjugated monoclonal antibodies (murine CD3-FITC, human CD4-APC [both Beckman Coulter, Krefeld, Germany]; murine CD8-PerCP, MHC-I (H-2D[b])-PE, murine CD4-PECy7, murine CD19-APCCy7 [BD Biosciences, Heidelberg, Germany]). A 20 minutes incubation was followed by two washing steps in PBS/1% FBS (1250 rpm, 5 minutes, room temperature [RT]). Finally the pellet was resuspended with 200 µl of PBS. Additionally, the viability of splenocytes and bone marrow cells was tested before transplantation by staining with 7-Amino-Actinomycin D (7AAD). $1\times10^6$ cells were incubated with 5 (0.25 µg/test) of 7AAD in 300 µl PBS for 30 min at room temperature and immediately measured. Data was acquired on a BD FACSCantoII™ Flow Cytometer and analysed using the BD FACSDIVA™ software (both BD Biosciences, Heidelberg, Germany).

Flow Cytometry and Hematology of Recipient Balb/c Wild-Type Mice.

Before and after transplantation procedure, recipient mice were analyzed by flow cytometry. At particular time points, blood (150 µl) was taken from the retro orbital vein of each mouse under ether anaesthesia. Blood was collected through heparinized capillaries (Greiner Biochemica, Flacht, Germany). Hemoglobin concentration was determined using an Animal Blood Counter (SCIL, Viernheim, Germany), which had been calibrated for mouse blood within 2 hours after blood taking. For cytometric analysis 100 µl of blood cells were incubated with 2.5 µl of conjugated monoclonal antibodies according to samples (murine CD4-PECy7, MHC-I (H-2D[b])-PE, MHC-I (H-2K[d])-FITC, murine CD8-PerCP, murine CD19-APCCy7 [BD Biosciences, Heidelberg, Germany]; murine CD3-FITC, human CD4-APC [Beckman Coulter, Krefeld, Germany]; human HLA-DR3-FITC [Immunotools, Friesoythe, Germany]. 20 minutes incubation was followed by erythrocyte lysing according to manufacturers instructions (BD FACS Lysing Solution [BD Biosciences, Heidelberg, Germany]). By adding of PBS/1% FBS samples were washed twice (1250 rpm, 5 minutes, room temperature [RT]). Finally, the pellet was resuspended with 200 µl of PBS. For cytometric analysis of murine FoxP3 for detection of regulatory T cells the murine $T_{reg}$ Detection Kit (Miltenyi Biotec GmbH, Bergisch Gladbach, Germany) was used. $1\times10^6$ cells were resuspended in 90 µl MACS Buffer (0.5% FCS, 2 mM EDTA in PBS, [Miltenyi Biotec, Bergisch Gladbach, Germany]) and cell surface markers were stained with 10 µl CD4-FITC and CD25-PE antibodies (Miltenyi Biotec, Bergisch Gladbach, Germany). After incubation in the dark for 10 min at 4° C. cells were washed with 2 ml MACS buffer and centrifuged at 300×g for 5 min at 4° C. After removing of the supernatant $1\times10^6$ cells were permeabilized by incubation for 30 min at 4° C. in a 1 ml of a freshly prepared fixation/permeabilization solution (containing formaldehyde). Cells were washed in 2 ml cold MACS buffer by centrifugation 300×g for 5 min at 4° C. For intracellular FoxP3 staining a permabilzation step was followed after removing of the supernatant. $1\times10^6$ cells were washed with 2 ml of a cold permeabilization buffer and centrifuged at 300×g for 5 min at 4° C. The cell pellet was resuspended in 80 µl of cold permeabilization buffer and incubated for 5 min at 4° C. Following, 10 µl of anti-FoxP3-APC (Miltenyi Biotec, Bergisch Gladbach, Germany) antibody was added, carefully mixed and incubated for 30 min at 4° C. Cells were washed with 2 ml of a cold permeabilization buffer and centrifuged at 300×g for 5 min at 4° C., supernatant was removed and cells were resuspended in 100 µl MACS buffer. Data were acquired on a BD FACSCantoII™ Flow Cytometer and analysed using the BD FACSDIVA™ software (both BD Biosciences, Heidelberg, Germany).

Immunhistology

Organs of mice were put in a stainless steel beaker (containing 2-methylbutane; Carl Roth, Karlsruhe, Germany), submerged in liquid nitrogen for 15 min and stored at −80° C. until ready for sectioning. Sectioning was done using a Cryostat (Leica Biosystems, Nussloch, Germany); objects were transferred onto a superfrost slide (Thermo Scientific, Braunschweig, Germany) and stored immediately at −80° C. until immunohistological analysis. The object slides were incubated with 0.3% w/v $H_2O_2$, dissolved in PBS for 10 min in a wet chamber, and then washed three times with PBS. Organs were treated with 10% w/v FBS in PBS for 60 min at RT, shortly washed with PBS, incubated with avidin solution (Dako North America, Carpinteria, USA) for 10 min and washed with PBS. The preparations were incubated with biotin solution (Dako North America) for 10 min, washed with PBS, and incubated with the primary antibody anti human CD4 antibody (United States Biological, Massachusetts, USA) or isotype control (Rat IgG1, κ, BD Biosciences, San Diego, USA), diluted 1:100, for 1 h at RT. Next, slides were covered with a secondary antibody (Biotin-conjugated Goat Anti-Rat $IgG_1$, BD Biosciences, San Diego, USA), diluted 1:100, for 30 min at RT and washed with PBS. The object slides were covered with Streptavidin-Horseradish Peroxidase (BD Biosciences, San Diego, USA) for 30 min, washed with PBS for three times (2 min for each washing step) and incubated with DAB dilution (BD Biosciences, San Diego, USA) for 5 min until an obvious intensity of color was achieved and then washed three times with ddH2O. The samples were covered with Mayer's hemalaun solution (Merck, Darmstadt, Germany) for 1 min and then washed with tap water for 10 min to visualize blue staining. The object slides passed through an ascending alcohol series (40-100% w/v), were incubated with xylene (Carl Roth) for 5 min and finally covered with Entellan® (Merck). Slides were analyzed under microscope (Zeiss, Axio, Imager A1, objective lenses 920 EX Plan-Neofluar, Axiocam MRc5 Zeiss, AxioVision Release 4.6.3; Gottingen, Germany).

Histology

Liver, bones and gut of all transgenic mice were analyzed histologically. Organs were prepared immediately after death and transferred into formalin (4% w/v; Merck) for hematoxylin-eosin (HE) and kaoline-aniline-orange G (KAO) staining. The formalin boxes were kept in the dark to prevent formalin precipitation. Bones were incubated in Osteosoft® for at least 7 days at room temperature. All samples were flushed with tap water for 2 h and then submerged in alcohol dilutions from 70 to 100% w/v for 9 h. The final incubation was with isopropanol (JT Baker, Deventer, The Netherlands) for 1 h and overnight with methylbenzoate (Riedel de-Häen, Seelze, Germany). After that, the organs were embedded in paraffin for 3 days and sliced (6 lm). The slides were incubated twice with xylene for 5 min at RT, passed through a descending alcohol series (100-50% w/v), and finally transferred into ddH2O at RT. Object slides were placed in Mayer's hemalaun solution for 5 min and washed with tap water for 10 min to reach a blue staining. After incubation with 1% w/v eosin Y, the slides passed through an ascending (70-100% w/v) alcohol series and were finally covered with Entellan® (Merck). The object slides were analyzed under the microscope (Nikon, Eclipse TE2000-E 920, objective lenses Plan Fluor 920/0.45 Ph1 DM ∞/0-2 WD 7.4 Histo, Software Nikon, LuciaG 5.00; Düsseldorf, Germany). Bones were stained with KAO as described according to Halmi-Konecny.

Example 2

Recombinant DNA techniques were performed using methods well known in the art and, as appropriate, supplier instructions for use of enzymes used in these methods. Sources of general methods included standard literature such as well-known books edited by Sambrook and Russel and by Ausubel. Detailed laboratory methods are also described below. In silico methods such as those described in WO9859244 were used to analyze the variable heavy and light chain sequences of mouse anti-CD4 for peptides predicted to bind to MHC Class II molecules (these were considered as T cell epitopes).

Example 2a: Chimeric Anti-CD4 Antibody mRNA was extracted from the mouse anti-CD4 hybridoma cells using a Poly A Tract System 1000 mRNA extraction kit: (Promega Corp. Madison Wis.) according to manufacturer's instructions. mRNA was reverse transcribed as follows: For the kappa light chain, 5.0 microliter of mRNA was mixed with 1.0 microliter of 20 pmol/microliter MuIgκVL-3' primer OL040 (Table 2) and 5.5 microliter nuclease free water (Promega Corp. Madison Wis.). For the lambda light chain, 5.0 microliter of mRNA was mixed with 1.0 microliter of 20 pmol/microliter MuIgκVL-3' primer OL042 (Table 2) and 5.5 microliter nuclease free water (Promega Corp. Madison Wis.). For the gamma heavy chain, 5 microliter of mRNA was mixed with 1.0 microliter of 20 pmol/microliter MuIgVH-3' primer OL023 (Table 1) and 5.5 microliter nuclease free water (Promega Corp. Madison Wis.). All three reaction mixes were placed in the pre-heated block of the thermal cycler set at 70° C. for 5 minutes. These were chilled on ice for 5 minutes before adding to each 4.0 microliter ImPromII 5x reaction buffer (Promega Corp. Madison Wis.), 0.5 microliter RNasin ribonuclease inhibitor (Promega Corp. Madison Wis.), 2.0 microliter 25 mM MgCl2 (Promega Corp. Madison Wis.), 1.0 microliter 10 mM dNTP mix (Invitrogen, Paisley UK) and 1.0 microliter Improm II reverse transcriptase (Promega Corp. Madison Wis.). The reaction mixes were incubated at room temperature for 5 minutes before being transferred to a pre-heated PCR block set at 42° C. for 1 hour. After this time the reverse transcriptase was heat inactivated by incubating at 70° C. in a PCR block for fifteen minutes.

Heavy and light chain sequences were amplified from cDNA as follows: A PCR master mix was prepared by adding 37.5 microliter 10x Hi-Fi Expand PCR buffer: (Roche, Mannheim Germany), 7.5 microliter 10 mM dNTP mix (Invitrogen, Paisley UK) and 3.75 microliter Hi-Fi Expand DNA polymerase (Roche, Mannheim Germany) to 273.75 microliter nuclease free water. This master mix was dispensed in 21.5 microliter aliquots into 15 thin walled PCR reaction tubes on ice. Into six of these tubes was added 2.5 microliter of MuIgVH-3' reverse transcription reaction mix and 1.0 microliter of heavy chain 5' primer pools HA to HF (see Table 1 for primer sequences and primer pool constituents). To another seven tubes was added 2.5 microliter of MuIgκVL-3' reverse transcription reaction and 1.0 microliter of light chain 5' primer pools LA to LG (Table 2). Into the final tube was added 2.5 microliter of MuIgκVL-3' reverse transcription reaction and 1.0 microliter of lambda light chain primer MuIgλVL5'-LI. Reactions were placed in the block of the thermal cycler and heated to 95° C. for 2 minutes. The PCR reaction was performed for 40 cycles of 94° C. for 30 seconds, 55° C. for 1 minute and 72° C. for 30 seconds. Finally the PCR products were heated at 72° C. for 5 minutes, and then held at 4° C.

TABLE 1

| Code | Sequence | Length | Name-Pool |
|---|---|---|---|
| OL007 | ATGRASTTSKGGYTMARCTKGRTTT | 25 | MuIgV$_H$5'-HA |
| OL008 | ATGRAATGSASCTGGGTYWTYCTCTT | 26 | MuIgV$_H$5'-HB |
| OL009 | ATGGACTCCAGGCTCAATTTAGTTTTCCT | 29 | MuIgV$_H$5'-HC |
| OL010 | ATGGCTGTCYTRGBGCTGYTCYTCTG | 26 | MuIgV$_H$5'-HC |
| OL011 | ATGGVTTGGSTGTGGAMCTTGCYATTCCT | 29 | MuIgV$_H$5'-HC |
| OL012 | ATGAAATGCAGCTGGRTYATSTTCTT | 26 | MuIgV$_H$5'-HD |
| OL013 | ATGGRCAGRCTTACWTYYTCATTCCT | 26 | MuIgV$_H$5'-HD |
| OL014 | ATGATGGTGTTAAGTCTTCTGTACCT | 26 | MuIgV$_H$5'-HD |
| OL015 | ATGGGATGGAGCTRTATCATSYTCTT | 26 | MuIgV$_H$5'-HE |
| OL016 | ATGAAGWTGTGGBTRAACTGGRT | 23 | MuIgV$_H$5'-HE |
| OL017 | ATGGRATGGASCKKIRTCTTTMTCT | 25 | MuIgV$_H$5'-HE |
| OL018 | ATGAACTTYGGGYTSAGMTTGRTTT | 25 | MuIgV$_H$5'-HF |
| OL019 | ATGTACTTGGGACTGAGCTGTGTAT | 25 | MuIgV$_H$5'-HF |
| OL020 | ATGAGAGTGCTGATTCTTTTGTG | 23 | MuIgV$_H$5'-HF |
| OL021 | ATGGATTTTGGGCTGATTTTTTTATTG | 28 | MuIgV$_H$5'-HF |
| OL023 | CCAGGGRCCARKGGATARACIGRTGG | 26 | MuIgV$_H$3'-2 |

(SEQ ID NOs: 70-85)

TABLE 2

| Code | Sequence | Length | Name-Pool |
|------|----------|--------|-----------|
| OL024 | ATGRAGWCACAKWCYCAGGTCTTT | 24 | MuIgkV$_L$5'-LA |
| OL025 | ATGGAGACAGACACACTCCTGTCTA | 25 | MuIgkV$_L$5'-LB |
| OL026 | ATGGAGWCAGACACACTSCTGYTATGGGT | 29 | MuIgkV$_L$5'-LC |
| OL027 | ATGAGGRCCCCTGCTCAGWTTYTTGGIWTCTT | 32 | MuIgkV$_L$5'-LD |
| OL028 | ATGGGCWTCAAGATGRAGTCACAKWYYCWGG | 31 | MuIgkV$_L$5'-LD |
| OL029 | ATGAGTGTGCYCACTCAGGTCCTGGSGTT | 29 | MuIgkV$_L$5'-LE |
| OL030 | ATGTGGGAYCGKTTTYAMMCTTTTCAATTG | 31 | MuIgkV$_L$5'-LE |
| OL031 | ATGGAAGCCCCAGCTCAGCTTCTCTTCC | 28 | MuIgkV$_L$5'-LE |
| OL032 | ATGAGIMMKTCIMTTCAITTCYTGGG | 26 | MuIgkV$_L$5'-LF |
| OL033 | ATGAKGTHCYCIGCTCAGYTYCTIRG | 26 | MuIgkV$_L$5'-LF |
| OL034 | ATGGTRTCCWCASCTCAGTTCCTTG | 25 | MuIgkV$_L$5'-LF |
| OL035 | ATGTATATATGTTTGTTGTCTATTTCT | 27 | MuIgkV$_L$5'-LF |
| OL036 | ATGAAGTTGCCTGTTAGGCTGTTGGTGCT | 29 | MuIgkV$_L$5'-LG |
| OL037 | ATGGATTTWCARGTGCAGATTWTCAGCTT | 29 | MuIgkV$_L$5'-LG |
| OL038 | ATGGTYCTYATVTCCTTGCTGTTCTGG | 27 | MuIgkV$_L$5'-LG |
| OL039 | ATGGTYCTYATVTTRCTGCTGCTATGG | 27 | MuIgkV$_L$5'-LG |
| OL040 | ACTGGATGGTGGGAAGATGGA | 21 | MuIgkV$_L$3'-1 |
| OL041 | ATGGCCTGGAYTYCWCTYWTMYTCT | 25 | MuIgλV$_L$5'-LI |
| OL042 | AGCTCYTCWGWGGAIGGYGGRAA | 23 | MuIgλV$_L$3'-1 |

(SEQ ID NOs: 86-104)

Amplification products were cloned into pGEM-T easy vector using the pGEM-T easy Vector System I (Promega Corp. Madison Wis.) kit and sequenced. The resultant mouse VH and VL sequences are shown as SEQ ID NOs: 1 and 2 (FIG. 12) and SEQ ID NOs: 11 and 12 (FIG. 13).

For generation of a chimeric antibody, VH region genes were amplified by PCR using the primers OL330 and OL331 (Table 3); these were designed to engineer in a 5' MluI and a 3' HindIII restriction enzyme site using plasmid DNA from one of the cDNA clones as template. Into a 0.5 ml PCR tube was added 5 microliter 10× Hi-Fi Expand PCR buffer: (Roche, Mannheim Germany), 1.0 microliter 10 mM dNTP mix (Invitrogen, Paisley UK), 0.5 microliter of Primer OL330, 0.5 microliter of primer OL331, 1.0 microliter template DNA and 0.5 microliter Hi-Fi Expand DNA polymerase (Roche, Mannheim Germany) to 41.5 microliter nuclease free water.

TABLE 3

| Code | Sequence | Length |
|------|----------|--------|
| OL 330 | GATCACGCGTGTCCACTCCGAAGTGCAGCTGGTGGAGTC | 39 |
| OL 331 | GTACAAGCTTACCTGAGGAGACGGTGACTGAGG | 33 |

(SEQ ID NOs: 105-106)

VL regions were amplified in a similar method using the oligonucleotides OL332 and OL333 (Table 4) to engineer in BssHII and BamHI restriction enzyme sites. Reactions were placed in the block of the thermal cycler and heated to 95° C. for 2 minutes. The polymerase chain reaction (PCR) reaction was performed for 30 cycles of 94° C. for 30 seconds, 55° C. for 1 minute and 72° C. for 30 seconds. Finally the PCR products were heated at 72° C. for 5 minutes, and then held at 4° C. VH and VL region PCR products were then cloned into the vectors pANTVhG4 and pANTVκ respectively (FIG. 11) at the MluI/HinDIII and BssHII/BamHI sites respectively. Both pANTVhG4 and pANTVκ are pAT153-based plasmids containing a human Ig expression cassette. The heavy chain cassette in pANTVhG4 consists of a human genomic IgG4 constant region gene driven by hCMVie promoter, with a downstream human IgG polyA region. pANTVhG4 also contains a hamster dhfr gene driven by the SV40 promoter with a downstream SV40 polyA region.

The light chain cassette of pANTVκ is comprised of the genomic human kappa constant region driven by hCMVie promoter with downstream light chain polyA region. Cloning sites between a human Ig leader sequence and the constant regions allow the insertion of the variable region genes.

TABLE 4

| Code | Sequence | Length |
|------|----------|--------|
| OL 332 | CATGGCGCGCGATGTGACATCCAGATGACTCAGTC | 35 |
| OL 333 | TGCGGGATCCAACTGAGGAAGCAAAGTTTAAATTCTACTCACGTCTCAGCTCCAGCTTGGTCC | 63 |

(SEQ ID NOs: 107-108)

NS0 cells (ECACC 85110503, Porton, UK) were co-transfected with these two plasmids via electroporation and selected in DMEM (Invitrogen, Paisley UK)+5% FBS (Ultra low IgG Cat No. 16250-078 Invitrogen, Paisley UK)+Penicillin/Streptomycin (Invitrogen, Paisley UK)+100 nM Methotrexate (Sigma, Poole UK). Methotrexate resistant colonies were isolated and antibody was purified by Protein A affinity chromatography using a 1 ml HiTrap MabSelect Sure column (GE Healthcare, Amersham UK) following the manufacturers recommended conditions.

NS0 supernatants were quantified for antibody expression in IgG Fc/Kappa ELISA using purified human IgG1/Kappa (Sigma, Poole UK) as standards. Immunosorb 96 well plates (Nalgene Hereford, UK) were coated with mouse anti-human IgG Fc-specific antibody (16260 Sigma, Poole UK) diluted at 1:1500 in 1×PBS (pH 7.4) at 37° C. for 1 hour. Plates were washed three times in PBS+0.05% Tween 20 before adding samples and standards, diluted in 2% BSA/PBS. Plates were incubated at RT for 1 hour before washing three times in PBS/Tween and adding 100 μl/well of detecting antibody goat anti-human kappa light chain peroxidase conjugate (A7164 Sigma, Poole UK) diluted 1:1000 in 2% BSA/PBS. Plates were incubated at RT for 1 hour before washing five times with PBS/tween and bound antibody detected using OPD substrate (Sigma, Poole UK). The assay was developed in the dark for 5 minutes before being stopped by the addition of 3M HCl. The assay plate was then read in a MRX TCII plate reader (Dynex Technologies, Worthing, UK) at 490 nm.

The chimeric antibody was tested in an ELISA-based competition assay using mouse anti-CD4 antibody, biotinylated using a B-Tag micro biotinylation kit (Sigma, Poole UK). A dilution series of chimeric IgG4 or control mouse antibody from 10 µg/ml to 0.009 µg/ml was premixed with a constant concentration of biotinylated anti-CD4 (0.2 µg/ml) before incubating 100 µl/well for 1 hour at room temperature in a Nunc MaxiSorp 96 well flat bottom microtitre plate (Fisher, Loughborough, UK) pre-coated with 50 µl/well of 1 µg/ml CD4. The binding of the biotinylated mAb was determined by incubating for 1 h at room temperature with 100 µl/well of a 1/500 dilution of streptavidin-HRP (Sigma), followed by detection with 100 µl/well OPD substrate (Sigma). After stopping the reaction with 50 µl/well 3M HCl, absorbance at 490 nm was measured using a Dynex Technologies (Worthing, UK) MRX TC II plate reader.

Figure 14:
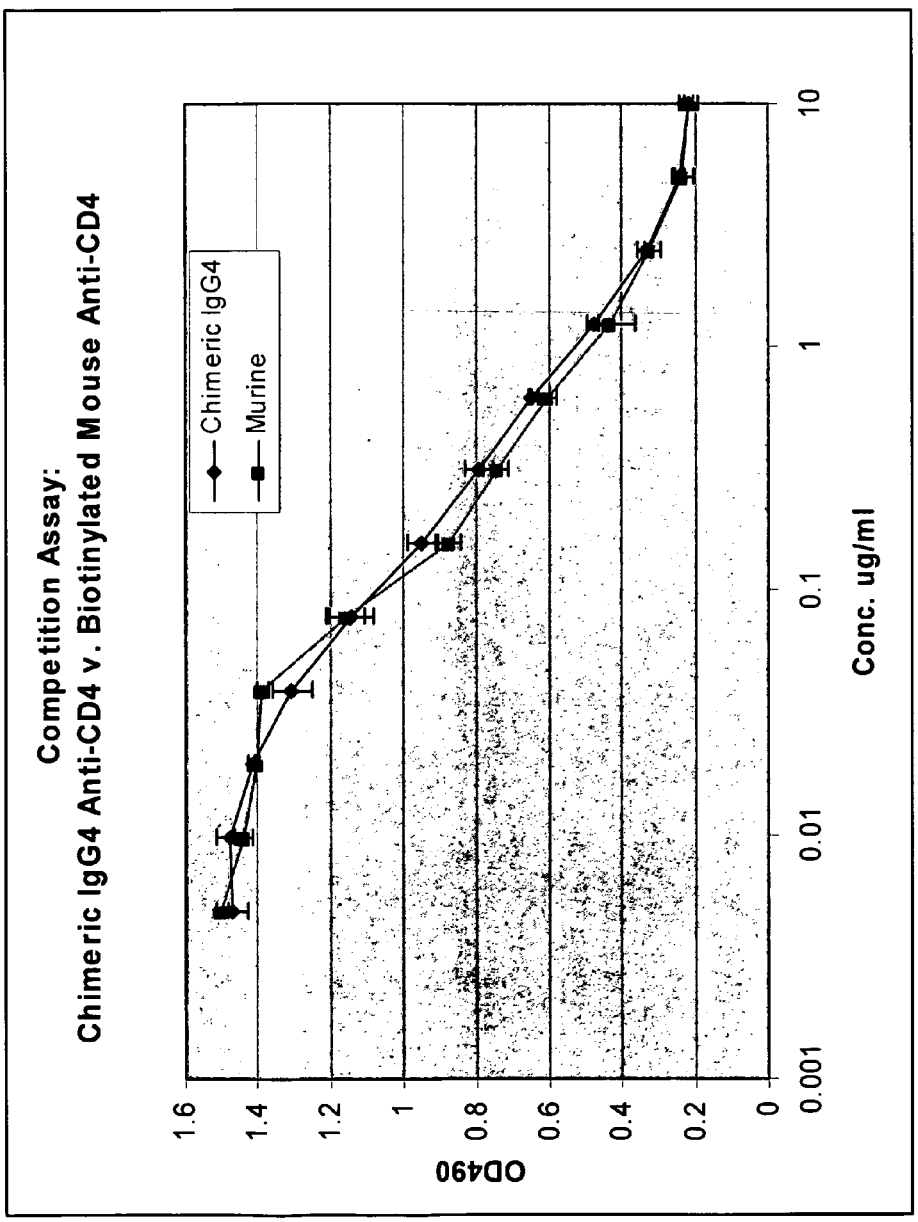
FIG. 14 depicts the relative binding of chimeric anti human CD4-antibody compared to the parental mouse anti-CD4 antibody.

The results obtained (FIG. 14) show that the chimeric IgG4 and mouse anti-CD4 antibodies have very similar binding profiles, with IC50 values of 0.25 µg/ml and 0.18 µg/ml respectively. Therefore the correct variable region sequences have been identified and cloned.

Example 2b: Design of Modified Anti-CD4 Antibodies

Sequential 9mer peptides spanning the entire length of the variable regions were tested in silico for binding against a panel of 34 MHC class II alleles. The scores for each individual allele were normalized to a scale of 0 to 1 and extensive validation with panels of known MHC class II binding peptides has demonstrated that a cut-off value of 0.55 effectively discriminates between predicted binding and non-binding peptides. In detail, potential MHC class II binding sequences within the variable domains were identified using the software iTope™. The iTope™ software predicts favorable interactions between amino acid side chains of a peptide and specific binding pockets within the binding grooves of 34 human MHC class II alleles. The location of key binding residues is achieved by the in silico generation of 9mer peptides that overlap by one amino acid spanning the test protein sequence. Each 9mer was scored based on the potential 'fit' and interactions of amino acid side chains with the binding groove of the MHC class II molecules. The peptide scores calculated by the software lie between 0 and 1. Peptides that produced a high mean binding score (>0.55 in the iTope™ scoring function) were highlighted and, if >50% of the MHC class II binding peptides, i.e. 17 out of 34 alleles had a high binding affinity (score >0.6), such peptides were defined as "promiscuous high affinity" MHC class II binding peptides which are considered a high risk for containing $CD4^+$ T cell epitopes. Moderate affinity MHC class II binding peptides bind a high number of alleles with high affinity but less than 17. High and moderate affinity binders were then analyzed using the iTope™ software for changes that could be made to the sequence that would reduce or remove binding to the MHC class II alleles. In making amino-acid selections, the range of amino-acids naturally found in human antibodies at any given position was considered. Alternatively, publicly available softwares could be used, for example:

ProPred (www.imtech.res.in/raghava/propred/),
Rankpep (bio.dfci.harvard.edu/RANKPEP/) or
NetMHCII (www.cbs.dtu.dk/services/NetMHCII/)

Ten MHC class II binding peptides were identified in the mouse heavy chain variable region (Table 5) and eleven identified in the mouse light chain variable region (Table 6). Tables 5 and 6 list the identified MHC class II binding sequences and the series of sequence variants that were used in the sequences of FIG. 12 and FIG. 13 in order to reduce MHC class II binding. Where MHC class II binding sequences were identified, amino acids in the peptide at key MHC class II binding positions were replaced with alternative amino acids in order to reduce or eliminate MHC class II binding. In some instances, more than one mutation was required to remove binding completely and, in other instance, MHC class II binding could not be completely removed although the numbers of alleles involved were small and the binding scores were close to the cut-off value.

TABLE 5

| Mouse | | VH4 | | VH3 | | VH2 | | VH1 | |
|---|---|---|---|---|---|---|---|---|---|
| Sequence | * | Sequence | * | Sequence | * | Sequence | * | Sequence | * |
| LQQSGTVLA | 26 | LQQSGTELK | 13 | LQQSGSELK | 0 | LQQSGSELK | 0 | LQQSGSELK | 0 |
| VLARPGASV | 29 | ELKRPGASV | 0 | ELKRPGASV | 0 | ELKRPGASV | 0 | ELKRPGASV | 0 |
| LARPGASVQ | 20 | LKRPGASVK | 2 | LKRPGASVK | 2 | LKRPGASVK | 2 | LKRPGASVK | 2 |
| MSCKASGYS | 18 | MSCKASGYT | 7 | MSCKASGYT | 7 | VSCKASGYT | 0 | VSCKASGYT | 0 |
| VKQRPGQGL | 24 | VKQAPGQGL | 1 | VKQAPGQGL | 1 | VKQAPGQGL | 1 | VRQAPGQGL | 1 |
| LTAVTSAST | 17 | LTAVTSAST | 17 | LTAVTSAST | 17 | LTADTSAST | 4 | ITRDTSAST | 0 |
| VTSASTAYM | 31 | VTSASTAYM | 31 | VTSASTAYM | 31 | DTSASTAYM | 0 | DTSASTAYM | 0 |
| LSSLTNEDS | 20 | LSSLTNEDS | 20 | LSSLTNEDT | 2 | LSSLTNEDT | 2 | LSSLTNEDT | 2 |

TABLE 5-continued

| Mouse | | VH4 | | VH3 | | VH2 | | VH1 | |
|---|---|---|---|---|---|---|---|---|---|
| Sequence | * | Sequence | * | Sequence | * | Sequence | * | Sequence | * |
| LDYWGQGTT | 21 | LDYWGQGTT | 21 | LDYWGQGTL | 0 | LDYWGQGTL | 0 | LDYWGQGTL | 0 |
| WGQGTTLTV | 27 | WGQGTTVTV | 0 | WGQGTLVTV | 0 | WGQGTLVTV | 0 | WGQGTLVTV | 0 |
| SEQ ID NOs: 21-30 | | | | SEQ ID NOs: 42-55, 138 | | | | | |

(*) Number of alleles bound

TABLE 6

| Mouse | | VK4 | | VK3 | | VK2 | | VK1 | |
|---|---|---|---|---|---|---|---|---|---|
| Sequence | * | Sequence | * | Sequence | * | Sequence | * | Sequence | * |
| IVLTQSPAI | 27 | IVLTQSPAI | 27 | IVLTQSPAT | 3 | IVLTQSPAT | 0 | IVLTQSPAT | 3 |
| VLTQSPAIM | 11 | VLTQSPAIM | 11 | VLTQSPATL | 0 | VLTQSPATL | 0 | VLTQSPATL | 0 |
| IMSASPGEK | 10 | IMSASPGEK | 10 | TLSASPGEK | 0 | TLSASPGEK | 0 | TLSASPGEK | 0 |
| MSASPGEKV | 24 | MSASPGEKV | 24 | LSASPGEKV | 2 | LSASPGEKV | 2 | LSASPGEKV | 2 |
| LLIYDTSNL | 6 | LLIYDTSNL | 6 | LLIYDTSNL | 6 | LLIYDTSNL | 6 | ALIYDTSNL | 0 |
| LASGVPVRF | 19 | LASGVPSRF | 2 | LASGVPSRF | 2 | LASGVPSRF | 2 | LASGVPSRF | 2 |
| VRFIGSGSG | 29 | SRFIGSGSG | 0 | SRFIGSGSG | 0 | SRFSGSGSG | 0 | SRFSGSGSG | 0 |
| FIGSGSGTS | 14 | FIGSGSGTD | 0 | FIGSGSGTD | 0 | FSGSGSGTD | 0 | FSGSGSGTD | 0 |
| IGSGSGTSY | 22 | IGSGSGTDY | 22 | IGSGSGTDY | 22 | SGSGSGTDY | 0 | SGSGSGTDY | 0 |
| YSLTISRME | 17 | YSLTISSME | 0 | YSLTISSME | 0 | YSLTISSME | 0 | YSLTISSME | 0 |
| FGAGTKLEL | 16 | FGAGTKLEI | 0 | FGAGTKLEI | 0 | FGAGTKLEI | 0 | FGAGTKLEI | 0 |
| SEQ ID NOs: 31-41 | | | | SEQ ID NOs: 56-69 | | | | | |

(*) Number of alleles bound

Example 2c: Generation of Modified Anti-CD4 Antibodies

Initial modified antibody VH and VK region genes were generated by overlap PCR mutagenesis of the parental mouse anti-CD4 variable regions from example 2a (SEQ ID NO: 1 (FIG. 12) and SEQ ID NO: 11 (FIG. 13)). (FIG. 12 and FIG. 13) using methods known in the art. Further variants were constructed by overlap PCR mutagenesis from SEQ ID NO: 3 (FIG. 12) and SEQ ID NO: 13 (FIG. 13). The assembled variants were then cloned directly into the expression vectors of FIG. 11. All clones were verified by DNA sequencing. In detail, PCR mutagenesis was performed as follows: Primer pairs were designed that spanned the region of the template nucleotide sequence that was to be altered, on both sense and anti-sense DNA strands. The primers contained the sequence that was to be introduced/altered, flanked by sequences that were identical to the template sequence and served to anchor the primers in the correct location. 5' and 3' end primers were also required that contained restriction sites suitable for cloning the mutated PCR product into the expression vectors (i.e. MluI and HinDIII for the VH gene and BssHII and BamHI for the VK gene). Tables 3, 4 and 7 list all the primers used for the construction of the de-immunized variants. For overlap PCR, small fragments of the gene are PCR amplified individually that overlap neighboring fragments at their ends, and mutations are introduced by the primers at the regions of overlap. The short PCR fragments are then purified and assembled together in a single PCR reaction using 5' and 3' end primers. To create the variant 4 genes, the murine variable regions were used as template and for all subsequent variants, the variant 4 genes were used as template for the PCR reactions: For VH variant 4, two individual PCRs were performed using OL335+OL337 and OL336+OL338, and the fragments joined using OL334+OL338. For VH variant 3, two individual PCRs were performed using OL339+OL341 and OL340+OL342, and the fragments joined using OL339+OL342. For VH variant 2, three individual PCRs were performed using OL330+OL344, OL343+OL346 and OL354+OL342, and the fragments joined using OL330+OL342. For VH variant 1, three individual PCRs were performed using OL339+OL348, OL347+OL350 and OL349+OL342, and the fragments joined using OL339+OL342. For VK variant 4, four individual PCRs were performed using OL332+OL352, OL351+OL354, OL353+OL356, and OL355+OL357 and the fragments joined using OL332+OL357. For VK variant 3, one PCR was performed using OL358+OL357. For VK variant 2, two individual PCRs were performed using OL358+OL360 and OL359+OL357, and the fragments joined using OL358+OL357. For VK variant 1, two individual PCRs were performed using OL358+OL362 and OL361+OL357, and the fragments joined using OL358+OL357. The PCR conditions used were as described in Example 2a for the amplification of the chimeric variable region genes. The PCR fragments generated were digested with either MluI and HinDIII for the VH genes or BssHII and BamHI for the VK genes and cloned into the appropriate expression vectors.

TABLE 7

| Code | Sequence | Length |
| --- | --- | --- |
| OL334 | GTTGCTACGCGTGTCCACTCCGAGGTTCAGCTCC AGCAGTCTGGGACTGaGCTGaaAAGGCCTGG | 65 |
| OL335 | ACTGaGCTGaaAAGGCCTGGGGCTTCCGTGaAGA TGTCCTGCAAGGCTTCTGGCTACAcCTTTGC | 65 |
| OL336 | ACAGGGTCTACAATGGATTGG | 21 |
| OL337 | CCAATCCATTGTAGACCCTGTCCAGGggcCTGTT TTA | 37 |
| OL338 | CCCAGAAAGCTTACCTGAGGAGACTGTGAcAG TGGTGCC | 39 |
| OL339 | GTTGCTACGCGTGTCCACTCCGAGGTTCAGCTCCA GCAGTCTGGGtCTGAGCTGAAAAGG | 60 |
| OL340 | CAAATGAGGACaCcGCGGTCTATT | 24 |
| OL341 | AATAGACCGCgGtGTCCTCATTTG | 24 |
| OL342 | CCCAGAAAGCTTACCTGAGGAGACTGTGAC AagGGTGCC | 39 |
| OL343 | CTTCCGTGAAGgTGTCCTGCAAGGC | 25 |
| OL344 | GCCTTGCAGGACAcCTTCACGGAAG | 25 |
| OL345 | AACTGACTGCAGaCACATCCGCCAG | 25 |
| OL346 | CTGGCGGATGTGtCTGCAGTCAGTT | 25 |
| OL347 | TGCACTGGGTAAgACAGGCCCCTGG | 25 |
| OL348 | CCAGGGGCCTGTcTTACCCAGTGCA | 25 |
| OL349 | GTTCAAGGACAAGGCCAAAaTcACTagAGA CACATCCGCCAGCACT | 46 |
| OL350 | AGTGCTGGCGGATGTGTCTctAGTgAtTTT GGCCTTGTCCTTGAAC | 46 |
| OL351 | CTCCAGGGGAGAAGGcCGCCATGACC | 26 |
| OL352 | GGTCATGGCGgCCTTCTCCCCTGGAG | 26 |
| OL353 | TCCTGATTTATGACACATCCAACCTGGCTTCT GGAGTCCCTtcTCGCTTCA | 51 |
| OL354 | GTTGGATGTGTCATAAATCAGGA | 23 |
| OL355 | TCTGGGACCgaTTACTCTCTCACAATCAG CaGcATGGAGGCTG | 43 |
| OL356 | CAGCCTCCATgCtGCTGATTGTGAGAGAGT AAtcGGTCCCAGA | 43 |
| OL357 | ATTGCGGGATCCAACTGAGGAAGCAAAGTTTAAA TTCTACTCACGTTTgAtCTCCAGCTTG | 61 |
| OL358 | CCCAGGCGCGCGATGTCAAATTGTTCTCACCCAG TCTCCAGCAAcCCTGTCTGCA | 55 |
| OL359 | TTCTCGCTTCAgcGGCAGTGGG | 22 |
| OL360 | CCCACTGCCgcTGAAGCGAGAA | 22 |

TABLE 7-continued

| Code | Sequence | Length |
| --- | --- | --- |
| OL361 | CTCCCCCAGAgcCCTGATTTAT | 22 |
| OL362 | ATAAATCAGGgcTCTGGGGGAG | 22 |

(SEQ ID NOs: 109-137)

Figure 15:
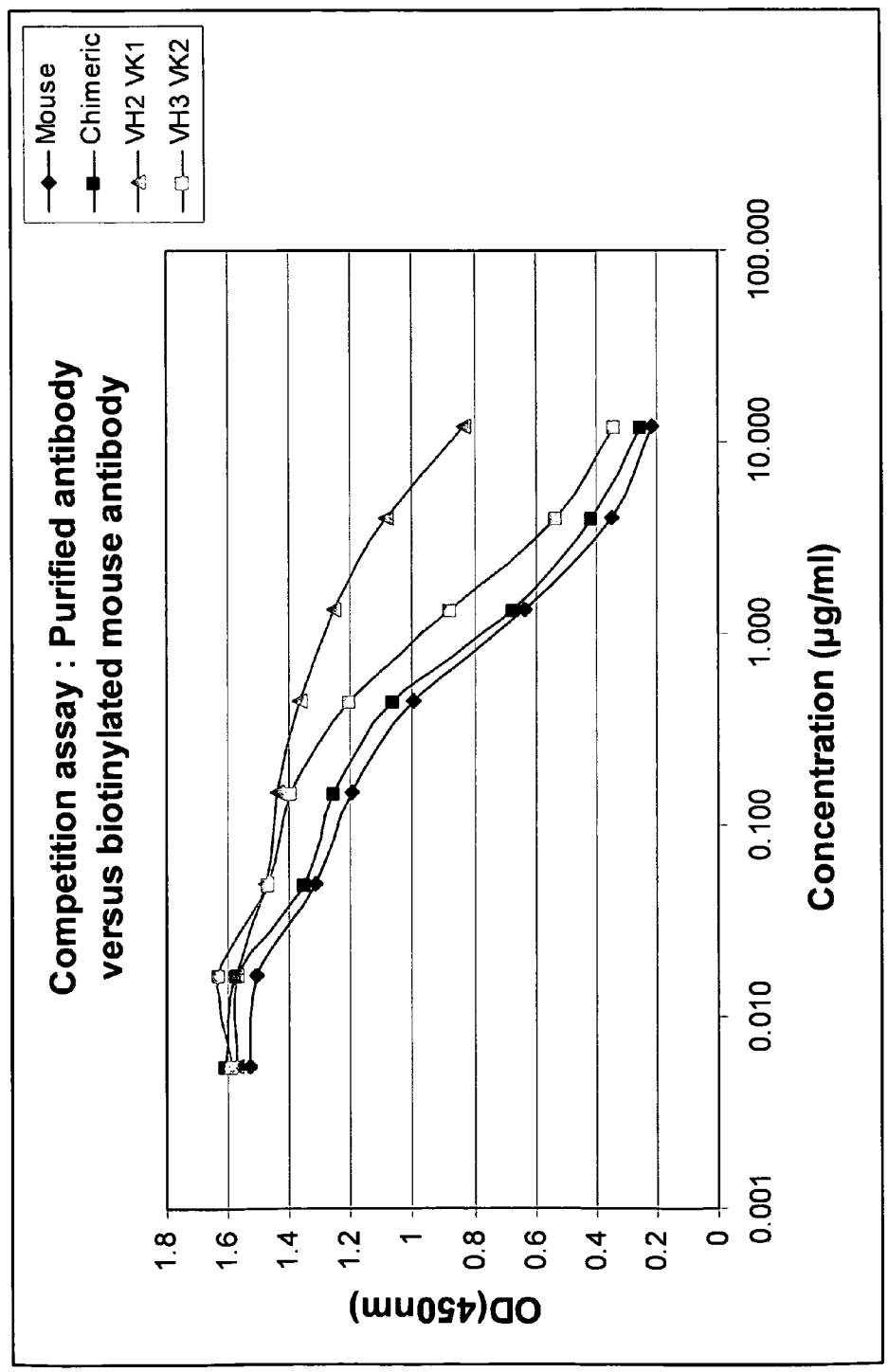
FIG. 15 depicts the relative binding of exemplary modified anti-CD4 antibodies compared to the parental mouse anti-CD4 antibody and chimeric anti-CD4 antibody.
Figure 15:
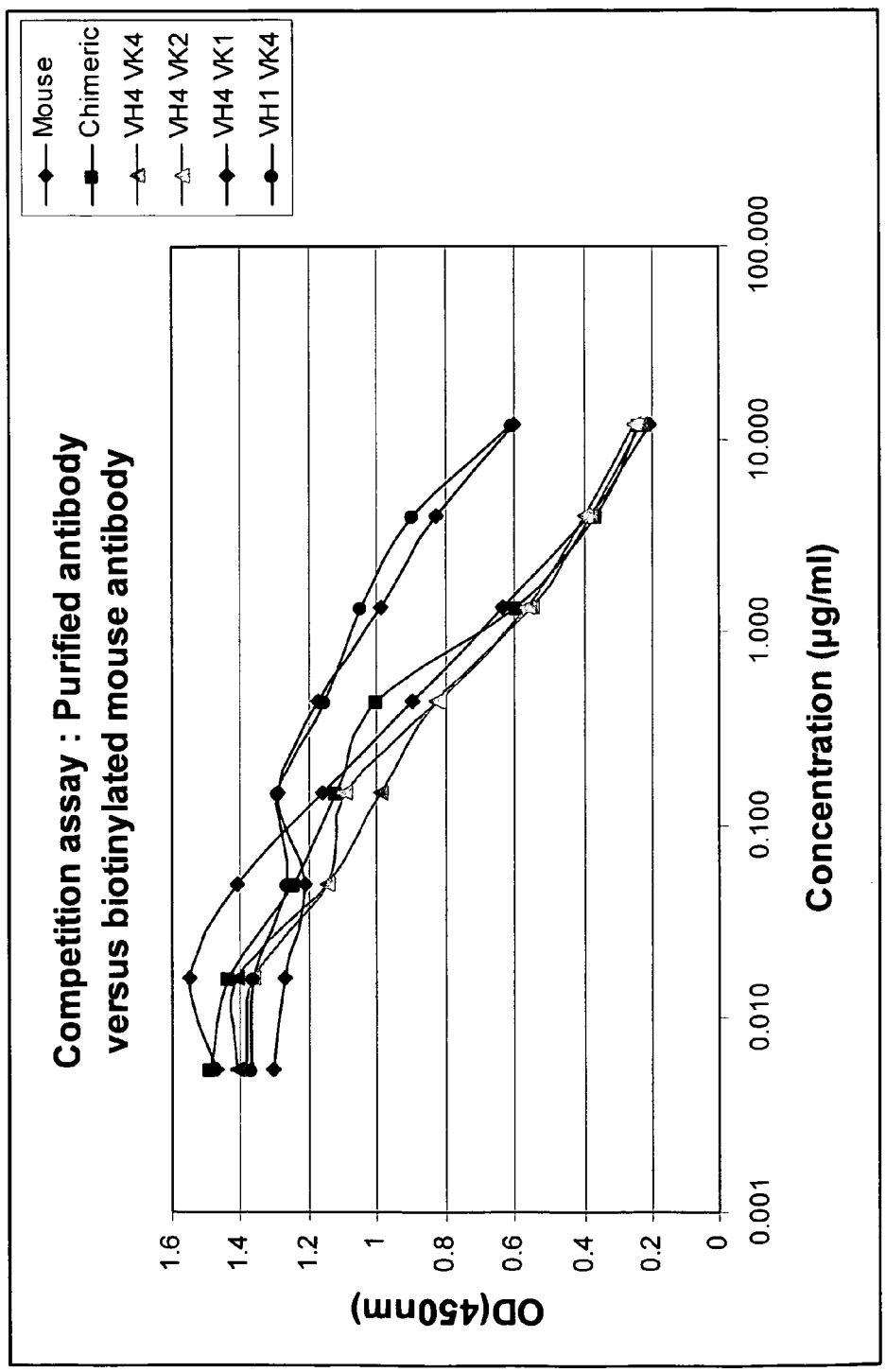
Figure 16:
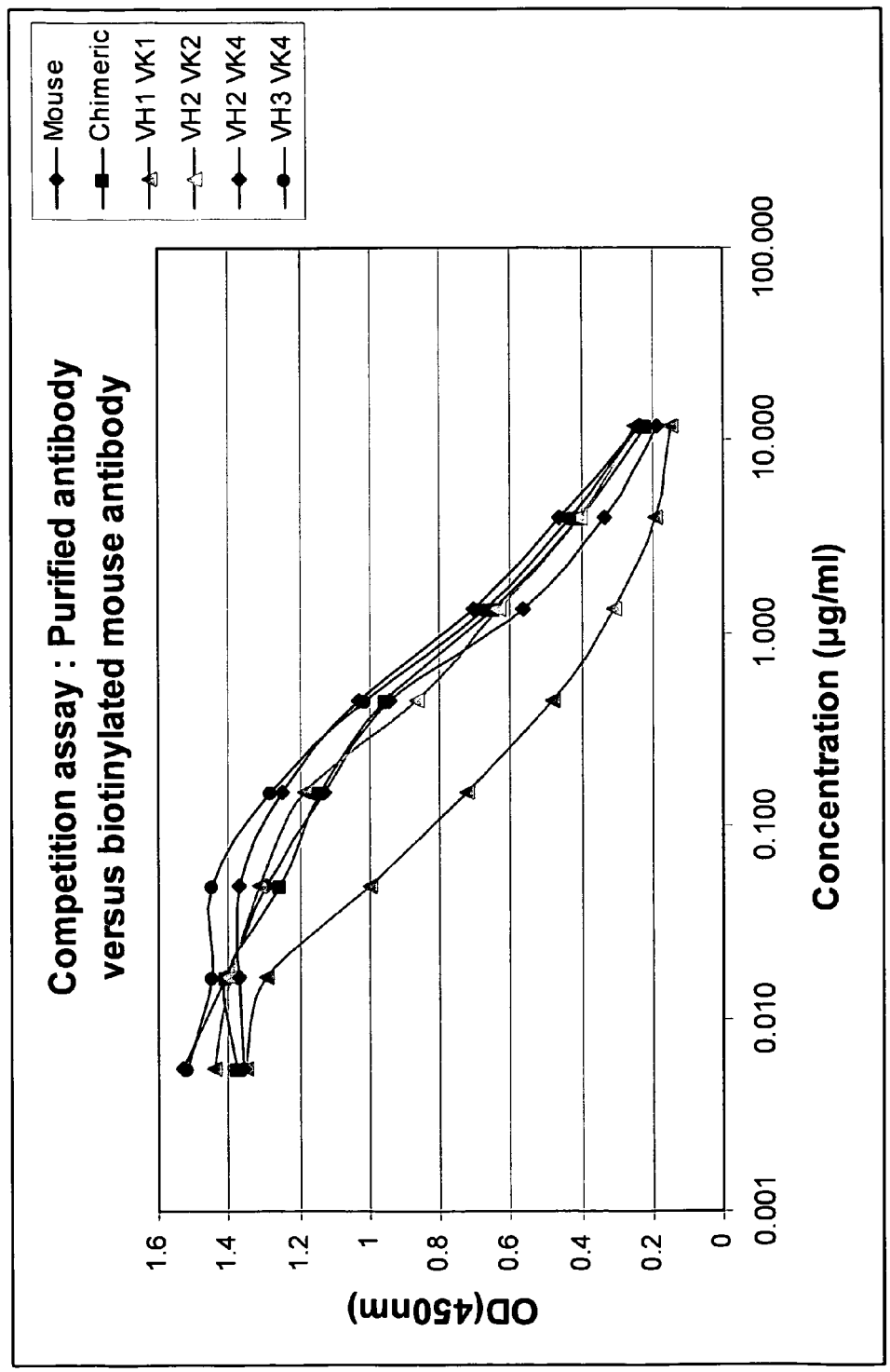
FIG. 16 depicts the relative binding of exemplary modified anti-CD4 antibodies compared to the parental mouse anti-CD4 antibody and chimeric anti-CD4 antibody.

All combinations of variant heavy and light chains (i.e. a total of 16 pairings) were stably transfected into NS0 cells via electroporation. Transfected cells were initially selected using 100 nM methotrexate, expanded into 200 nm methotrexate and tested for IgG expression as in example 2a. No expression was observed with variants possessing the VK3 chain or with variants VH3/VK1 and VH/VK2. The best expressing lines for each variant were expanded and frozen under liquid nitrogen. Anti human CD4-antibody variants from the NS0 stable transfections were purified from cell culture supernatants via protein A affinity chromatography. Supernatants were pH adjusted with 0.1 volumes of 10×PBS pH 7.4 and passed over 1 ml Mab Select Sure Protein A columns (GE Healthcare, Amersham, UK). The columns were washed with 10 volumes of PBS pH 7.4 before elution with 50 mM citrate buffer pH 3.0. 1 ml fractions were collected and immediately neutralized with 0.1 ml of 1M Tris-HCl pH 9.0. Protein containing fractions (as measured by absorbance at 280 nm) were pooled, buffer exchanged into PBS pH 7.4 and the purified antibodies stored at +4° C. The concentrations of the purified antibodies were measured by UV absorbance at 280 nm. The purified antibodies were tested for binding to their target, human CD4 via competition ELISA. Nunc MaxiSorp 96 well flat bottom microtitre plates (Fisher) were coated overnight at 4° C. with 50 µl/well of 1 µg/ml CD4 in PBS pH 7.4. Duplicate titrations of mouse antibody and epitope depleted antibody samples were generated (in the range 0.005 µg/ml to 12 µg/ml) and mixed with a constant concentration (0.2 µg/ml) of biotinylated mouse antibody in PBS pH 7.4/2% BSA. The titrations (final volume 100 µl/well) were added to pre-washed (4× with PBS pH 7.4/0.05% Tween 20) assay plates and incubated at room temperature for 1 hour. Plates were then washed as above and 100 µl/well of a 1/500 dilution of streptavidin HRP (Sigma) in PBS pH 7.4/0.05% Tween 20 was added and incubated for a further 1 hour at room temperature. After further washing, bound biotinylated mouse antibody was detected with 100 µl/well 3,3'-5,5' tetramethylbenzidine substrate (Sigma). After stopping the reaction with 50 µl/well 3M HCl, absorbance was measured at 450 nm on a Dynex Technologies MRX TC II plate reader and the binding curves of the test antibodies were compared to the mouse reference standard and the purified chimeric antibody. The results are shown in FIG. 15 and FIG. 16. Absorbance was plotted against sample concentration and straight lines were fitted through each of the data sets. The equations of the lines were used to calculate the concentration required to inhibit biotinylated mouse antibody binding to CD4 by 50% (IC50). The IC50 values of the test samples were divided by that of the mouse antibody to calculate the fold difference in binding efficiencies. These values are reported in Table 8, which shows that seven of the antibodies (highlighted in underlining) bind at least within two-fold of the mouse reference antibody and four antibodies (VH1/VK1, VH2/VK2, VH4/VK2 and VH4/VK4) show binding that is improved.

TABLE 8

Relative Binding of Anti-CD4 Variants

|     | VK1  | VK2  | VK3 | VK4  |
|-----|------|------|-----|------|
| VH1 | 0.14 | —    | —   | 5.06 |
| VH2 | 8.66 | 0.96 | —   | 1.44 |
| VH3 | —    | 1.77 | —   | 1.44 |
| VH4 | 3.89 | 0.73 | —   | 0.49 |

LIST OF REFERENCES

DE 3919294
EP 1 454 137
US 20030153043
WO 199106667
WO 1998/59244;
WO 2000/34317;
WO 2004/112835
Aschan, J. Allogeneic haematopoietic stem cell transplantation: current status and future outlook. *Br. Med Bull.* 77-78, 23-36 (2006).
Auletta, J. J. & Cooke, K. R. Bone marrow transplantation: new approaches to immunosuppression and management of acute graft-versus-host disease. *Curr. Opin. Pediatr.* 21, 30-38 (2009).
Bacigalupo, A., Frassoni, F. & Van Lint, M. T. Bone marrow or peripheral blood as a source of stem cells for allogeneic transplantation. *Haematologica* 87, 4-8 (2002).
Bates, J. S., Engemann, A. M. & Hammond, J. M. Clinical utility of rituximab in chronic graft-versus-host disease. *Ann. Pharmacother.* 43, 316-321 (2009).
Benekli, M. et al. Muromonab-CD3 (Orthoclone OKT3), methylprednisolone and cyclosporine for acute graft-versus-host disease prophylaxis in allogeneic bone marrow transplantation. *Bone Marrow Transplant.* 38, 365-370 (2006).
Boon et al. (2002) Toxicology, 172:191-203
Bowers, K., Pitcher, C. & Marsh, J. M. CD4: A co-receptor in the immune response and HIV infection. *Int. J. Biochem. Cell Biol.* 29, 871-875 (1997).
Chatenoud, L., Waldmann, H. & Emmrich, F. Tolerance induction in the adult: 'danger' at Le Bischenberg. *Immunol. Today* 16, 121-123 (1995).
Chen, H. R. et al. [CD25 monoclonal antibody for GVHD prophylaxis in non-T-cell depleted haploidentical bone marrow transplantation for treatment of childhood leukemia]. *Zhonghua Er. Ke. Za Zhi.* 42, 294-298 (2004).
Chester, K. A. & Hawkins, R. E. Clinical issues in antibody design. *Trends Biotechnol.* 13, 294-300 (1995).
Coligan et al., Current Protocols in Immunology, John Wiley & Sons 1991-1997
Cooke K R, Kobzik L, Martin T R, Brewer J, Delmonte J, Crawford J M et al. An experimental model of idiopathic pneumonia syndrome after bone marrow transplantation .1. The roles of minor H antigens and endotoxin. *Blood* 88(8):3230-3239 (1996)
Emmrich, F. et al. An anti-CD4 antibody for treatment of chronic inflammatory arthritis. Agents Actions Suppl 32, 165-170 (1991a).
Emmrich, J., Seyfarth, M., Fleig, W. E. & Emmrich, F. Treatment of inflammatory bowel disease with anti-CD4 monoclonal antibody. *Lancet* 338, 570-571 (1991b).
Fehervari, Z., Cooke, A., Brett, S. & Turner). Perturbation of naive TCR transgenic T cell functional responses and upstream activation events by anti-CD4 monoclonal antibodies. *Eur. J. Immunol.* 32, 333-340 (2002).
Harding, S., Lipp, P. & Alexander, D. R. A therapeutic CD4 monoclonal antibody inhibits TCR-zeta chain phosphorylation, zeta-associated protein of 70-kDa Tyr319 phosphorylation, and TCR internalization in primary human T cells. *J. Immunol.* 169, 230-238 (2002).
Harlow E & Lane D (2006) Antibody purification on protein A or protein G columns. Cold Spring Harb. Protoc.; 2006; doi:10.1101/pdb.prot4283
Higuchi et al. 1988, Nucleic Acids Res. 16: 7351
Hosono, M. et al. Human/mouse chimeric antibodies show low reactivity with human anti-murine antibodies (HAMA). *Br. J. Cancer* 65, 197-200 (1992).
Isaacs J. D. (1990) Sem. Immunol. 2: 449-456
Ji, S. Q. et al. Anti-CD25 monoclonal antibody (basiliximab) for prevention of graft-versus-host disease after haploidentical bone marrow transplantation for hematological malignancies. *Bone Marrow Transplant.* 36, 349-354 (2005).
Kabat et al. (1991) Sequences of proteins of immunological interest. 5th Edn. NIH Publication No. 91-3242)
Kameda, H. & Takeuchi, T. [Rheumatoid arthritis]. *Nippon Rinsho* 67, 495-499 (2009).
Kern et al. (1998) Nature Medicine 4:975-978
Kestendjieva, S. et al. Characterization of mesenchymal stem cells isolated from the human umbilical cord. *Cell Biol. Int.* 32, 724-732 (2008).
Knop, S. et al. Treatment of steroid-resistant acute GVHD with OKT3 and high-dose steroids results in better disease control and lower incidence of infectious complications when compared to high-dose steroids alone: a randomized multicenter trial by the EBMT Chronic Leukemia Working Party. *Leukemia* 21, 1830-1833 (2007).
Kohlhaw, K. et al. The monoclonal anti-CD4 antibody RIB5/2 induces donor-specific tolerance in the high-responder liver transplant model in the rat. *Transplant. Proc.* 33, 2371-2373 (2001).
Kwok et al (2001) TRENDS in Immunol. 22:583-588
Laub, R. et al. Anti-human CD4 induces peripheral tolerance in a human CD4+, murine CD4−, HLA-DR+ advanced transgenic mouse model. *J. Immunol.* 169, 2947-2955 (2002).
Laub, R. et al. A multiple transgenic mouse model with a partially humanized activation pathway for helper T cell responses. *J. Immunol. Methods* 246, 37-50 (2000).
Madrenas, J., Schwartz, R. H. & Germain, R. N. Interleukin 2 production, not the pattern of early T-cell antigen receptor-dependent tyrosine phosphorylation, controls anergy induction by both agonists and partial agonists. *Proc. Natl. Acad. Sci. U.S. A* 93, 9736-9741 (1996).
Marshall et al. (1994) J. Immunol. 152:4946-4956
O'Sullivan et al. (1990) J. Immunol. 145: 1799-1808
Reinke, P. et al. Anti-CD4 therapy of acute rejection in long-term renal allograft recipients. *Lancet* 338, 702-703 (1991).
Reinke, P. et al. Anti-CD4 monoclonal antibody therapy of late acute rejection in renal allograft recipients—CD4+ T cells play an essential role in the rejection process. *Transplant. Proc.* 27, 859-862 (1995).
Robadey et al. (1997) J. Immunol 159: 3238-3246
Schroff et al. (1985) Cancer Res. 45: 879-885
Senolt, L., Vencovsky, J., Pavelka, K., Ospelt, C. & Gay, S. Prospective new biological therapies for rheumatoid arthritis. *Autoimmun. Rev.* (2009).
Stern et al. (1994) Nature 368: 215-221
von Bonin, M. et al. Treatment of refractory acute GVHD with third-party MSC expanded in platelet lysate-containing medium. *Bone Marrow Transplant.* 43, 245-251 (2009).

The invention claimed is:

1. An in vitro method of modifying a cell graft containing CD4 positive immune cells comprising the steps of
   a) incubating a cell graft containing CD4 positive immune cells with an anti CD4 antibody recognizing the first domain of CD4, wherein said incubating is carried out for from 1 minute to 1 day to allow the binding of the anti CD4 antibody to from 40% to 100% of the accessible CD4 epitopes of said cell graft, and
   b) removing unbound antibody from said graft by washing said graft to yield a modified cell graft.

2. The method of claim 1, wherein said incubating is carried out for from 1 minute to 8 hours.

3. The method of claim 1, wherein said incubating is carried out with an antibody amount of from 0.1 µg/ml to 10 mg/ml.

4. The method of claim 1, wherein said graft is a cell suspension.

5. The method of claim 4, wherein said graft is selected from the group consisting of a cell suspension comprising bone marrow cells, non adherent bone marrow cells, peripheral blood cells, cord blood cells, cells from Wharton's jelly, and/or placenta-derived cells; a cell suspension comprising lymphocytes, monocytes and/or macrophages.

6. The method of claim 1, wherein said graft comprises stem cells.

7. The method of claim 1, wherein said anti CD4 antibody is selected from the group consisting of: Max16H5, OKT4A, OKTcdr4a, cMT-412, YHB.46, 30F16H5, an antibody obtainable from a cell line deposited with accession number ECACC 88050502, an antibody obtainable from a cell line MAX. 16H5/30F16H5 deposited with the DSMZ on Dec. 2, 2011, 16H5.chimIgG4, an antibody obtainable from a cell line CD4.16H5.chimIgG4 deposited with the DSMZ on Dec. 2, 2011, an antibody comprising the VH and the VK of antibody 16H5.chimIgG4, an antibody comprising a VH and a VK of an antibody obtainable from a cell line CD4.16H5.chimIgG4 deposited with the DSMZ on Dec. 2, 2011, an antibody comprising any combination of a VH disclosed in FIG. 12 and of a VK disclosed in FIG. 13, an antibody comprising VH1 disclosed in FIG. 12 and VK1 disclosed in FIG. 13, an antibody comprising VH2 disclosed in FIG. 12 and VK2 disclosed in FIG. 13, an antibody comprising VH4 disclosed in FIG. 12 and VK2 disclosed in FIG. 13, and an antibody comprising VH4 disclosed in FIG. 12 and VK4 disclosed in FIG. 13.

8. The method of claim 1, wherein said graft is additionally incubated with soluble bioactive molecules, selected from agents promoting one or more selected from the group consisting of immunosuppression, immunotolerance and formation of regulatory T cells.

* * * * *